US011205519B2

(12) United States Patent
Ramazzotti et al.

(10) Patent No.: US 11,205,519 B2
(45) Date of Patent: Dec. 21, 2021

(54) METHODS, COMPUTER-ACCESSIBLE MEDIUM AND SYSTEMS TO MODEL DISEASE PROGRESSION USING BIOMEDICAL DATA FROM MULTIPLE PATIENTS

(71) Applicants: NEW YORK UNIVERSITY, New York, NY (US); UNIVERSITA DEGLI STUDI DI MILANO—BICOCCA, Milan (IT)

(72) Inventors: Daniele Ramazzotti, Muggio (IT); Giulio Caravagna, Viareggio (IT); Loes Olde Loohuis, New York, NY (US); Alex Graudenzi, Modena (IT); Ilya Korsuncky, New York, NY (US); Giancarlo Mauri, Varedo (IT); Marco Antoniotti, Lugano (CH); Bhubaneswar Mishra, Great Neck, NY (US)

(73) Assignees: NEW YORK UNIVERSITY, New York, NY (US); UNIVERSITA DEGLI STUDI DI MILANO—BICOCCA, Milan (IT)

(*) Notice: Subject to any disclaimer, the term of this patent is extended or adjusted under 35 U.S.C. 154(b) by 85 days.

(21) Appl. No.: 16/192,418

(22) Filed: Nov. 15, 2018

(65) Prior Publication Data

US 2019/0326019 A1 Oct. 24, 2019

Related U.S. Application Data

(63) Continuation of application No. 15/032,903, filed as application No. PCT/US2014/062688 on Oct. 28, 2013, now abandoned.

(60) Provisional application No. 61/896,566, filed on Oct. 28, 2013, provisional application No. 62/038,697, filed on Aug. 18, 2014, provisional application No. 62/040,802, filed on Aug. 22, 2014.

(51) Int. Cl.
| | |
|---|---|
| *G01N 33/48* | (2006.01) |
| *G16H 50/50* | (2018.01) |
| *G16B 5/00* | (2019.01) |
| *G16B 5/10* | (2019.01) |
| *G16B 5/20* | (2019.01) |
| *G06N 5/00* | (2006.01) |
| *G06N 7/00* | (2006.01) |
| *G06N 20/00* | (2019.01) |

(52) U.S. Cl.
CPC .............. *G16H 50/50* (2018.01); *G06N 5/00* (2013.01); *G06N 7/005* (2013.01); *G06N 20/00* (2019.01); *G16B 5/00* (2019.02); *G16B 5/10* (2019.02); *G16B 5/20* (2019.02)

(58) Field of Classification Search
None
See application file for complete search history.

(56) References Cited

U.S. PATENT DOCUMENTS

| | | |
|---|---|---|
| 2010/0280809 A1 | 11/2010 | Takahashi et al. |
| 2013/0116999 A1 | 5/2013 | Stein et al. |
| 2013/0218474 A1 | 8/2013 | Longo |
| 2013/0268290 A1 | 10/2013 | Jackson et al. |

OTHER PUBLICATIONS

Geneletti, Sara, et al. "Assessing causal relationships in genomics: From Bradford-Hill criteria to complex gene-environment interactions and directed acyclic graphs." Emerging Themes in Epidemiology 8.1 (2011): 1-18.*
Hainke, Katrin, Jörg Rahnenführer, and Roland Fried. "Disease progression models: A review and comparison." Dortmund University, Technical Report (2011).*
Goeman, Jelle J., and Ulrich Mansmann. "Multiple testing on the directed acyclic graph of gene ontology." Bioinformatics 24.4 (2008): 537-544.*
Strobl, Ralf, Eva Grill, and Ulrich Mansmann. "Graphical modeling of binary data using the LASSO: a simulation study." BMC medical research methodology 12.1 (2012): 1-13.*
Loohuis, Loes Oide, et al. "Inferring causal models of cancer progression with a shrinkage estimator and probability raising." bioRxiv (2013): 000919.*
Tsai, Chu-Lin, and Carlos A. Camargo Jr. "Methodological considerations, such as directed acyclic graphs, for studying "acute on chronic" disease epidemiology: chronic obstructive pulmonary disease example." Journal of clinical epidemiology 62.9 (2009): 982-990.*
Beerenwinkel, Niko et al., "Conjunctive Bayesian Networks," Bernoulli, vol. 13, No. 4, pp. 893-909, 2007.
Beerenwinkel, Niko et al., "Learning Multiple Evolutionary Pathways from Cross-Sectional . . . ," Journal of Computational Biology, vol. 12, No. 6, pp. 584-598, 2005.
Bell, D. et al., "Integrated Genomic Analysis of Ovarian Carcinoma," Nature, vol. 474, No. 7353, pp. 609-615, Dec. 30, 2011.
Desper, Richard et al., "Inferring Tree Models for Oncogenesis from Comparative . . . ," Journal of Computational Biology, vol. 6, No. 1, pp. 37-51, 1999.

(Continued)

*Primary Examiner* — Anna Skibinsky
(74) *Attorney, Agent, or Firm* — Hunton Andrews Kurth LLP

(57) ABSTRACT

An exemplary embodiment of system, method and computer-accessible medium can be provided to reconstruct models based on the probabilistic notion of causation, which can differ fundamentally from that can be based on correlation. A general reconstruction setting can be complicated by the presence of noise in the data, owing to the intrinsic variability of biological processes as well as experimental or measurement errors. To gain immunity to noise in the reconstruction performance, it is possible to use a shrinkage estimator. On synthetic data, the exemplary procedure can outperform currently known procedures and, for some real cancer datasets, there are biologically significant differences revealed by the exemplary reconstructed progressions. The exemplary system, method and computer accessible medium can be efficient even with a relatively low number of samples and its performance quickly converges to its asymptote as the number of samples increases.

14 Claims, 49 Drawing Sheets

(56) References Cited

OTHER PUBLICATIONS

Desper, Richard et al., "Distance-Based Reconstruction of Tree Models for . . . ," Journal of Computational Biology, vol. 7, No. 6, pp. 789-803, 2000.
Edmonds, Jack "Optimum Branchings," Journal of Research, vol. 71B, No. 4, pp. 233-240, Oct.-Dec. 1967.
Efron, B., "Bootstrap Methods: Another Look at the Jackknife," The Annals of Statistics, vol. 7. No. 1, pp. 1-26, 1979.
Efron, Bradley, "The Jacknife, the Bootstrap, and the Other Resampling . . . ," Division of Biostatistics, Stanford University, Technical Report No. 63, pp. 1-40, Dec. 1980.
Efron, Bradley, "Large-Scale Inference: Empirical Bayes Methods for Estimation . . . ," Stanford University, Cambrdige University Press, pp. 1-273, 2013.
Efron, Bradley et al., "Stein's Estimation Rule and Its Competitors . . . ," Journal of the American Statistical Association, vol. 68, No. 341, pp. 117-130, Mar. 1973.
Gerstung, Moritz et al., "Quantifying Cancer Progression with Conjunctive . . . ," Bioinformatics, vol. 25, No. 21, pp. 2809-2815, 2009.
Gerstung, Moritz et al., "The Temporal Order of Genetic and Pathway Alternations . . . ," PloS One, vol. 6, Issue 11, pp. 1-9, Nov. 2011.
Gunawan, B. et al., "An Oncogenetic Tree Model in Gastrointestinal Stromal . . . ," Journal of Pathology, vol. 211, pp. 463-470, 2007.
Hanahan, Douglas et al., "The Hallmarks of Cancer," Cell Press, vol. 100, pp. 57-70, Jan. 7, 2000.
Hanahan, Douglas et al., "Hallmarks of Cancer: The Next Generation," Cell Press, vol. 144, pp. 646-674, Mar. 4, 2011.
Hitchcock, C. et al., "Probabilistic Causation," The Stanford Encyclopedia of Philiosophy, Spring Edition 2012, pp. 1-36, 2012.
Hjelm, Marcus et al., "New Probabilistic Network Models and Algorithms for Oncogenesis," Journal of Computational Biological, vol. 13, No. 4, pp. 853-865, 2006.
Huang, Qiang et al., "Genetic Differences Detected by Comparative Genomic Hybridization . . . ," Genes, Chromosomes & Cancer, vol. 34, pp. 224-233, 2002.
Imielinski, Marcin et al., "Mapping the Hallmarks of Lung Adenocarcinoma with Massively . . . ," Cell, vol. 150, No. 6, pp. 1107-1120, Sep. 14, 2012.
Ionita, Iuliana et al., "Mapping Tumor-Suppressor Genes with Multipoint . . . ," The American Journal of Human Genetics, vol. 79, pp. 13-22, Jul. 2006.
Kainu, Tommi et al., "Somatic Deletions in Hereditary Breast Cancers Implicate . . . ," PNAS, vol. 97, No. 17, pp. 9603-9608, Aug. 15, 2000.
Kleinberg, Samantha "Causality, Probability and Time," Cambridge University Press, pp. 1-8, 2012.
Knutsen, Turid et al., "The Interactive Online SKY/M-FISH & CGH Database . . . ," Genes Chromosomes Cancer, vol. 44, No. 1, pp. 52-64, Sep. 21, 2005.
Longerich, Thomas et al., "Oncogenetic Tree Modeling of Human Hepatocarcinogenesis," International Journal of Cancer, vol. 130, pp. 575-583, 2012.
Luo, Ji et al., "Principles of Cancer Therapy: Oncogene and Non-Oncogene Addiction," Cell, vol. 136, No. 5, pp. 823-837, Mar. 6, 2009.
Pathare, Swapnali et al., "Construction of Oncogenetic Tree Models Reveals Multiple . . . ," International Journal Of Cancer, vol. 124, No. 12, pp. 2864-2871, Jun. 15, 2009.
Radmacher, Michael D. et al., "Graph Models of Oncogenesis with an Application . . . ," Journal Theor. Biol., vol. 212, pp. 535-548, 2001.
Reichenbach, H., "The Direction of Time," University of California Press, pp. 1-292, 1956.
Samuelson, Emma et al., "BAC CGH-Array Identified Specific Small-Scale Genomic . . . ," BMC Cancer, vol. 12, pp. 1-10, 2012.
Suppes, Patrick "A Probabilistic Theory of Causality," North-Holland Publishing Company—Amsterdam, pp. 1-131, 1970.
Tibshirani, Robert "Regression Shrinkage and Selection Via the Lasso," Journal of the Royal Statistical Society, Series B, vol. 58, No. 1, pp. 267-288, 1996.
Vogelstein, Bert et al., "Genetic Alterations During Colorectal-Tumor Development," The New England Journal of Medicine, vol. 319, No. 9, pp. 525-532, Sep. 1, 1988.
Vogelstein, Bert et al., "Cancer Genes and the Pathways They Control," Nature Medicine, vol. 10, No. 8, pp. 789-799, Aug. 2004.
Xue, Wen et al., "A Cluster of Cooperating Tumor-Suppressor Gene Candidates . . . ," PNAS, vol. 109, No. 21, pp. 8212-8217, May 22, 2012.
Zhang, Kaizhong et al., "Simple Fast Algorithms for the Editing Distance Between . . . ," SIAM Journal on Computing, vol. 18, No. 6, pp. 1245-1262, Dec. 1989.
Hume, David, "Enquiry Concerning Human Understanding," First Enquiry, pp. 1-88, Jul. 2004 and Jan. 2008.
Kyburg, Henry E. Jr., "Discussion: Salmon's Paper*," Philisophy of Science, pp. 147-151, 1965.
Reichenbach, H. et al., The Direction of Time, The University of California Press, pp. 65 and 66, 1970.
Cartwright, Nancy, "Causal Laws and Effictive Strategies," Indiana University Press, Nous 13, pp. 419-437, 1979.
Dupre, John, "Discussion: Probabilistic Causality: A Rejoinder to Ellery Eells," Philisophy of Science, Stanford University, vol. 57, pp. 690-698, 1990.
Pearl, Judea, "Models, Reasoning, and inference," Causality, Cambridge Univeristy Press, pp. 1-7, 2000.
Menzies, P., "Counterfactual Therories of Causation," The Stanford Encyclopedia of Philosophy, Spring 2014 Edition, pp. 1-14, 2014.
Lewis, David "Causation," Journal of Philosophy, pp. 556-567, 1973.
Woodward, J., "Causation and Manipulability," The Stanford Encyclopedia of Philiosophy, Winter 2013 Edition, pp. 124, 2013.
Koller, Daphne et al., "Probabilistic Graphical Models: Principles and Techniques," The MIT Press, pp. 1-16, 2009.
Pearl, Judea "Probabilistic Reasoning In Intelligent Systems: Networks of . . . ," The Morgan Kaufmann Series in Represenation and Reasoning, pp. 1-4, 1988.
Verman, TS et al., "Equivalence and Synthesis of Causal Models," Uncertainty in Artifical Intelligence, No. 6, pp. 255-268, 1990 and 1991.
Chickering, David Maxwell "Learning Bayesian Networks is NP-Complete," Com. Sci. Dep., University of California, pp. 121-130, 1996.
Chickering, David Maxwell et al., "Large-Sample Learning of Bayesian . . . ," Journal of Machine Learning Research, vol. 5, pp. 1287-1330, 2004.
Spirtes, Peter et a., "Causation, Prediction, and Serch," Springer-Veriag, pp. 1-551, vol. 81, 2000.
Tsamardinos, Ioannis et al., "Algorithms for Large Scale Markov Blanket Discovery," FLAIRS Conference, pp. 376-381, 2003.
Carvalho, Alexandra M. "Scoring Functions for Learning Bayesian Networks," Ineso-Id Tec. Rep, pp. 1-48, 2009.
Moon, T.K. "The Expectiation-Maximization Algorithm," IEEE Signal Processing Magazine, vol. 13, No. 6, pp. 47-60, Nov. 1996.
Kirkpatrick, Scott "Optimizaition by Simulated Annealing: Quantitative Studies," Journal of Statistical Physics, vol. 34, Nos. 5 and 6, pp. 975-986, 1984.
Loohuis, Loes Olde et al., "Inferring Tree Causal Models of Cancer Progression with . . . ," PLOS One, vol. 9, Issue 10, pp. 1-14, Oct. 2014.
Szabo, Aniko et al., "Estimating an Oncogenetic Tree when False Negatives and Positives . . . ," Mathematical Biosciences, vol. 176, pp. 219-236, 2002.
Mann, H.B. et al., "On a Test of Whether One of Two Random Variables is Stochastically . . . ," Annals of Mathematical Statistics, vol. 18, No. 1, pp. 50-60, Mar. 1947.
Schwarz, Gideon "Estimating the Dimension of a Model," The Annals of Statistics, vol. 6, No. 2, pp. 461-464, 1978.
Heckerman, David et al., "Learning Bayesian Networks: The Combination of Knowledge . . . ," Machine Learning, pp. 1-10, 1995.

(56) References Cited

OTHER PUBLICATIONS

Hamming, R.W. "Error Detecting and Error Correcting Codes," The Bell System Technical Journal, vol. XXIX, No. 2, pp. 1-14, Apr. 1950.

Antoniotti, Marco et al., "Implementation of the TRONCO Package for Translation . . . ," http://www.bioconductor.org, Sep. 25, 2015.

Margaritis, Dimitris "Learning Bayesian Networks Model Structure from Date," Carnegie-Mellon University, Ph.D. Thesis, pp. 1-126, May 2003.

Farahani, Hossein Shahrabi et al., "Learning Oncogenetic Networks by Reducing . . . ," PLOS One, vol. 8, Issue 6, pp. 1-8, Jun. 2013.

Piazza, Rocco et al., "Recurrent SETBP1 Mutations in Atypical Chronic Myeloid . . . ," Nat. Genet., vol. 45, No. 1, pp. 18-24, Jan. 2013.

Imielinsk, Marcin et al., "Mapping the Hallmarks of Lung Adenocarcinoma . . . ," Cell, vol. 150, No. 6, pp. 1107-1120, Sep. 14, 2012.

International Search Report for International Application No. PCT/US2014/062688 dated Jan. 21, 2015.

International Written Opinion for International Application No. PCT/US2014/062688 dated Jan. 21, 2015.

\* cited by examiner

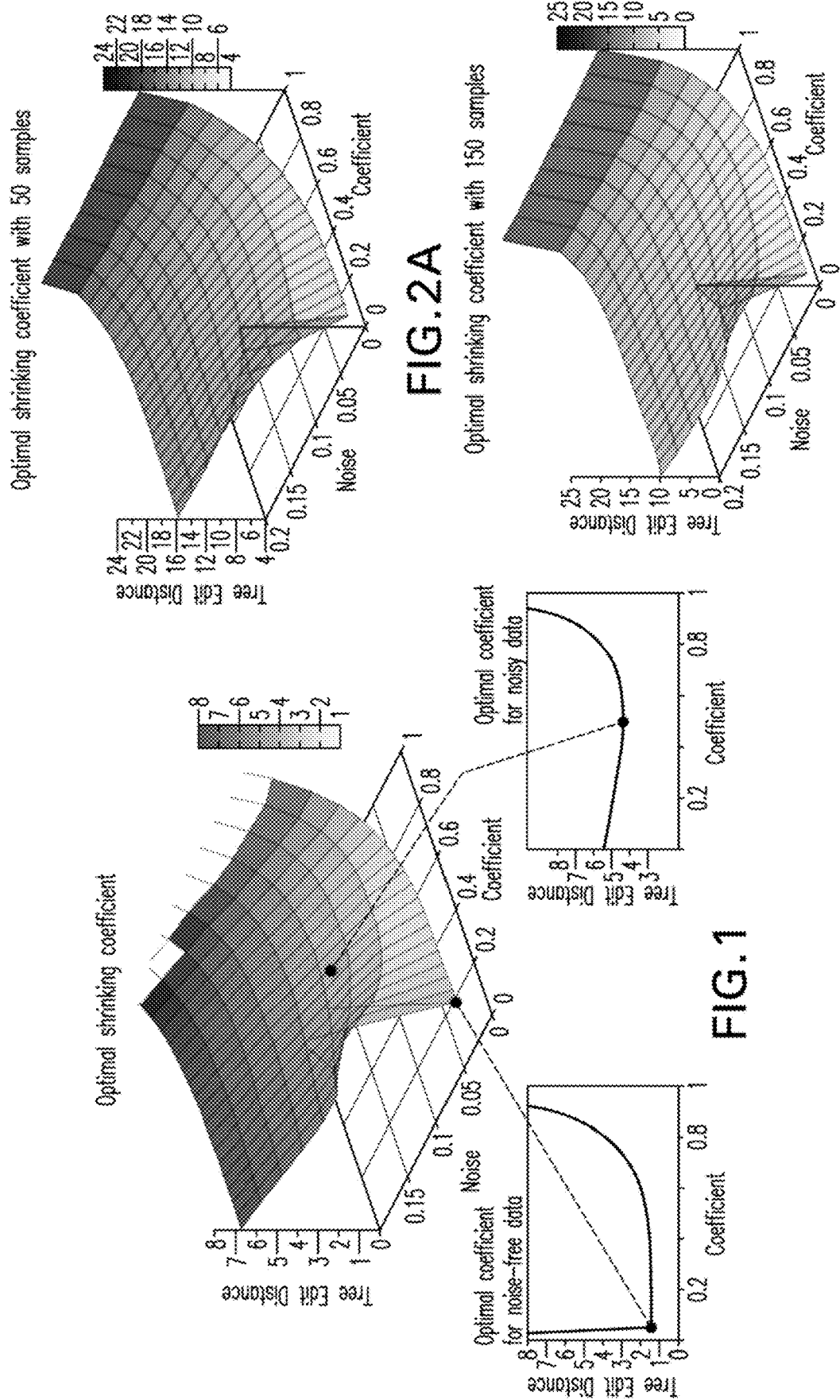

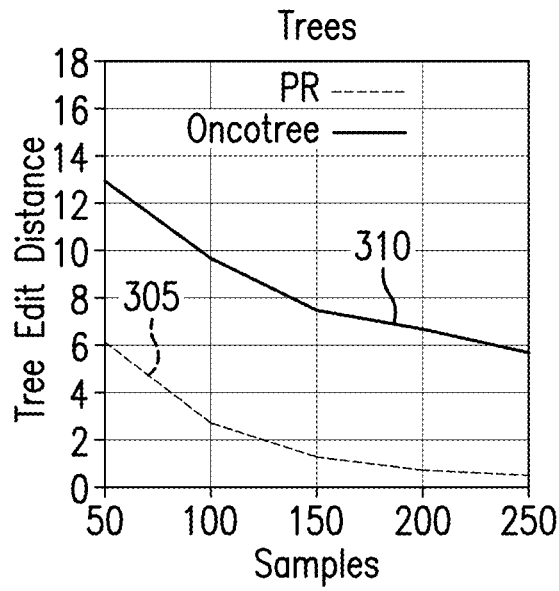
FIG.3A
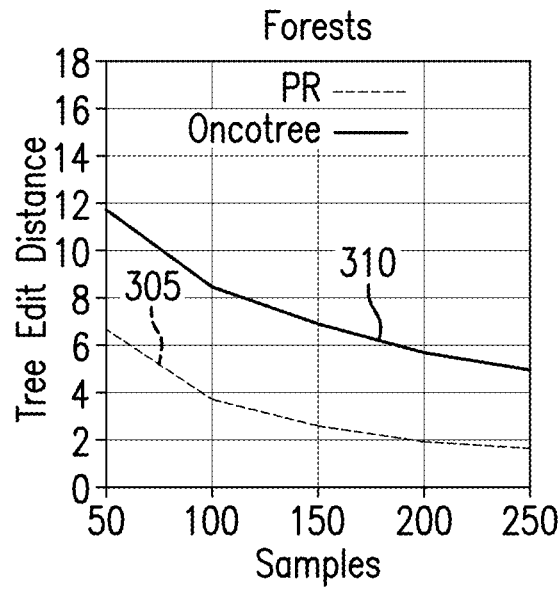
FIG.3B
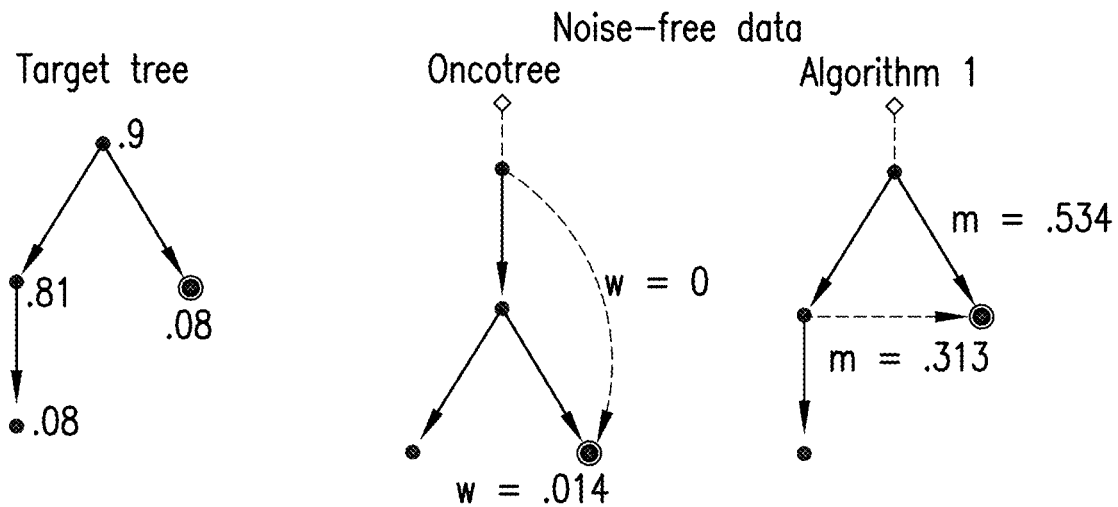
FIG.4A
FIG.4B

Oncotrees (overall confidence 8.3%)

| → | 8q+ | 3q+ | 5q− | 4q− | 8p− | 1q+ | Xp− |
|---|---|---|---|---|---|---|---|
| ◇ | .99 | .06 | .51 | .22 | .004 | .8 | .06 |
| 8q+ | 0 | .092 | .08 | 0.16 | 0.4 | .02 | .007 |
| 3q+ | .002 | 0 | .04 | 0 | 0 | .09 | .04 |
| 5q− | .001 | .002 | 0 | .52 | .39 | .009 | .16 |
| 4q− | 0 | 0 | 27 | 0 | .14 | .05 | .11 |
| 8p− | 0 | 0 | .07 | .08 | 0 | .004 | .59 |
| 1q+ | 0 | 0 | 0 | .004 | 0 | 0 | 0 |
| Xp− | 0 | 0 | .003 | .003 | .04 | .01 | 0 |

FIG.7A

Algorithm 1 (overall confidence 8.6%)

| → | 8q+ | 3q+ | 5q− | 4q− | 8p− | 1q+ | Xp− |
|---|---|---|---|---|---|---|---|
| ◇ | .99 | .06 | .51 | .22 | .004 | .8 | .06 |
| 8q+ | 0 | .92 | .06 | .16 | .62 | .01 | .008 |
| 3q+ | .002 | 0 | .03 | .002 | 0 | .09 | .04 |
| 5q− | .001 | .002 | 0 | .5 | .26 | .009 | .17 |
| 4q− | 0 | 0 | .29 | 0 | .09 | .05 | .12 |
| 8p− | 0 | 0 | .07 | .08 | 0 | .004 | .59 |
| 1q+ | 0 | 0 | 0 | .004 | 0 | 0 | 0 |
| Xp− | 0 | .001 | .003 | .004 | .01 | .01 | 0 |

FIG.7B

Screening off (*Reichenbach*)

Background contexts (*Cartwright*)

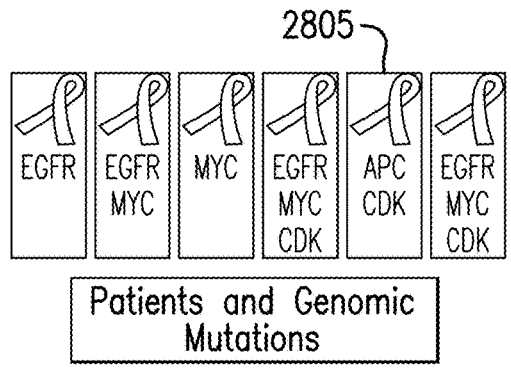
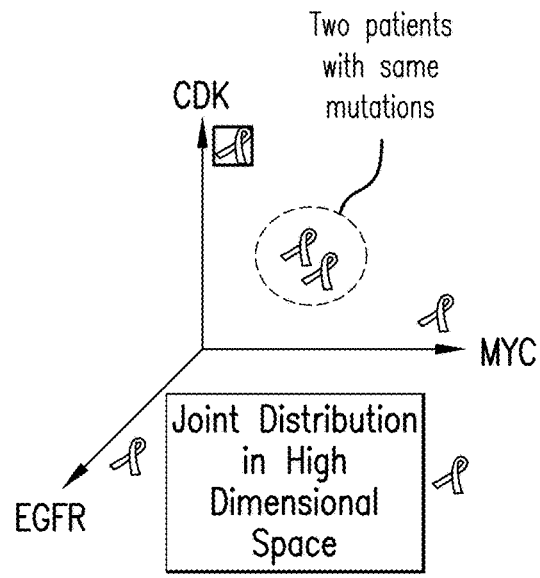
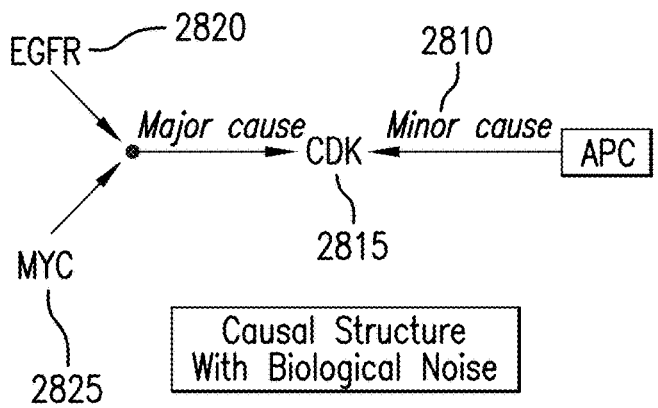
FIG.28A
FIG.28B
FIG.28C
FIG.28D

METHODS, COMPUTER-ACCESSIBLE MEDIUM AND SYSTEMS TO MODEL DISEASE PROGRESSION USING BIOMEDICAL DATA FROM MULTIPLE PATIENTS

CROSS-REFERENCE TO RELATED APPLICATIONS

This application is a continuation of U.S. patent application Ser. No. 15/032,903, filed on Apr. 28, 2016, which relates to and claims the benefit and priority from International Patent Application No. PCT/US2014/062688 filed on Oct. 28, 2014, which relates to and claims the benefit and priority from U.S. Patent Application No. 61/896,566, filed on Oct. 28, 2013, U.S. Patent Application No. 62/038,697 filed on Aug. 18, 2014, and U.S. Patent Application No. 62/040,802 filed on Aug. 22, 2014, the entire disclosures of which are incorporated herein by reference in their entireties.

FIELD OF THE DISCLOSURE

The present disclosure relates generally to cancer progression models, and more specifically, to exemplary embodiments of an exemplary system, method and computer-accessible medium for a determination of cancer progression models, which can include noise and/or biological noise and/or can use biological data from multiple patients.

BACKGROUND INFORMATION

Cancer is a disease of evolution. Its initiation and progression can be caused by dynamic somatic alterations to the genome manifested as point mutations, structural alterations of the genome, DNA methylation and histone medication changes. (See e.g., Reference 15). These genomic alterations can be generated by random processes, and since individual tumor cells compete for space and resources, the test variants can be naturally selected for. For example, if through some mutations of a cell acquires the ability to ignore anti-growth signals from the body, this cell may thrive and divide and its progeny may eventually dominate part of the tumor. This clonal expansion can be seen as a discrete state of the cancer's progression, marked by the acquisition of a genetic event, or a set of events. Cancer progression can then be thought of as a sequence of these discrete progression steps, where the tumor acquires certain distinct properties at each state. Different progression sequences can be used, although some can be more common than others, and not every order can be viable. (See, e.g., References 14 and 25).

In the last two decades, many specific genes and genetic mechanisms have been identified that are involved in different types of cancer (see, e.g. References 3, 19 and 31), and targeted therapies that aim to affect the product of these genes are developed at a fast pace. (See, e.g., Reference 25). However, unfortunately, the causal and temporal relations among the genetic events driving cancer progression remain largely elusive. The main reason for this state of affairs can be that information revealed in the data can usually be obtained only at one, or a few points, in time, rather than over the course of the disease. Extracting this dynamic information from the available static, or cross-sectional data can be a challenge, and the combination of mathematical, statistical and computational techniques can be needed to decipher the complex dynamics. The results of the research addressing these issues will have important repercussions for disease diagnosis and prognosis, and therapy.

In recent years, several methods that aim to extract progression models from cross-sectional data have been developed; starting from the seminal work on single-path-models (see, e.g., Reference 32), up to several models of oncogenetic trees (see, e.g., References 2, 4 and 4), probabilistic networks (see, e.g., Reference 17) and conjunctive Bayesian networks (see, e.g., References 1 and 11). Some of these models, use correlation to identify relations among genetic events. (See e.g., References 2, 4 and 5). These techniques reconstruct tree models of progression as independent acyclic paths with branches and no consequences. More complex models (see e.g., References 1 and 11), extract topologies such as direct acyclic graphs. However, in these cases, other constraints on the joint occurrence of events can be imposed.

Accordingly, there is a need to address and/or solve at least some of the deficiencies described herein above.

SUMMARY OF EXEMPLARY EMBODIMENTS

To that end, an exemplary system, method and computer-accessible medium for generating a model of progression a disease(s) using biomedical data of a patient(s) can be provided. Such exemplary system, method and computer-accessible medium can be used to, for example, obtain the biomedical data, and generate the model of progression which includes (i) states of the disease or (ii) transitions among the states based on the obtained biomedical data. The model of progression can include a progression graph. The progression graph can be based on a causal graph. The model of progression can include a directed acyclic graph, where nodes of the DAG can be atomic events and edges represent a progression between the atomic events. The model of progression can be further based on a noise model, which can include a biological noise model, an experimental noise model or a combination thereof. The biological noise model can be used to distinguish spurious causes from genuine causes.

In some exemplary embodiments of the present disclosure, the biomedical data can include genomics, transcriptomics, epigeneomics or imaging data and/or can include information pertaining to a normal cell(s), a tumor cell(s), cell-free circulating DNA or a circulating tumor cell(s). The states of the disease can be determined by genomics, transcriptomics or epigeneomics mutational profiles, and/or by a causality relationship whose strength is estimated by probability-raising by an unbiased estimator(s). The unbiased estimator can include a shrinkage estimator(s), which can be a measure of causation among any pair of events atomic events.

In certain exemplary embodiments of the present disclosure, the disease can include cancer. Further biomedical data related to a further patient(s) can be received, and information about the further patient can be generated based on the model of progression and the further biomedical data. The information can be a classification of a further disease(s) of the further patient(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 1 is a graph of an exemplary shrinkage coefficient according to an exemplary embodiment of the present disclosure;

FIGS. 2A and 2B are graphs of optimal λ datasets of different sizes according to an exemplary embodiment of the present disclosure;

FIGS. 3A and 3B are graphs illustrating an exemplary comparison of noise-free synthetic data according to an exemplary embodiment of the present disclosure;

FIGS. 4A and 4B are diagrams of a set of exemplary reconstructed trees according to an exemplary embodiment of the present disclosure;

FIGS. 7A and 7B are charts illustrating the estimated confidence for ovarian cancer progression according to an exemplary embodiment of the present disclosure;

FIGS. 28A-28D is a diagram illustrating an exemplary procedure according to an exemplary embodiment of the present disclosure;

Figure 5A:
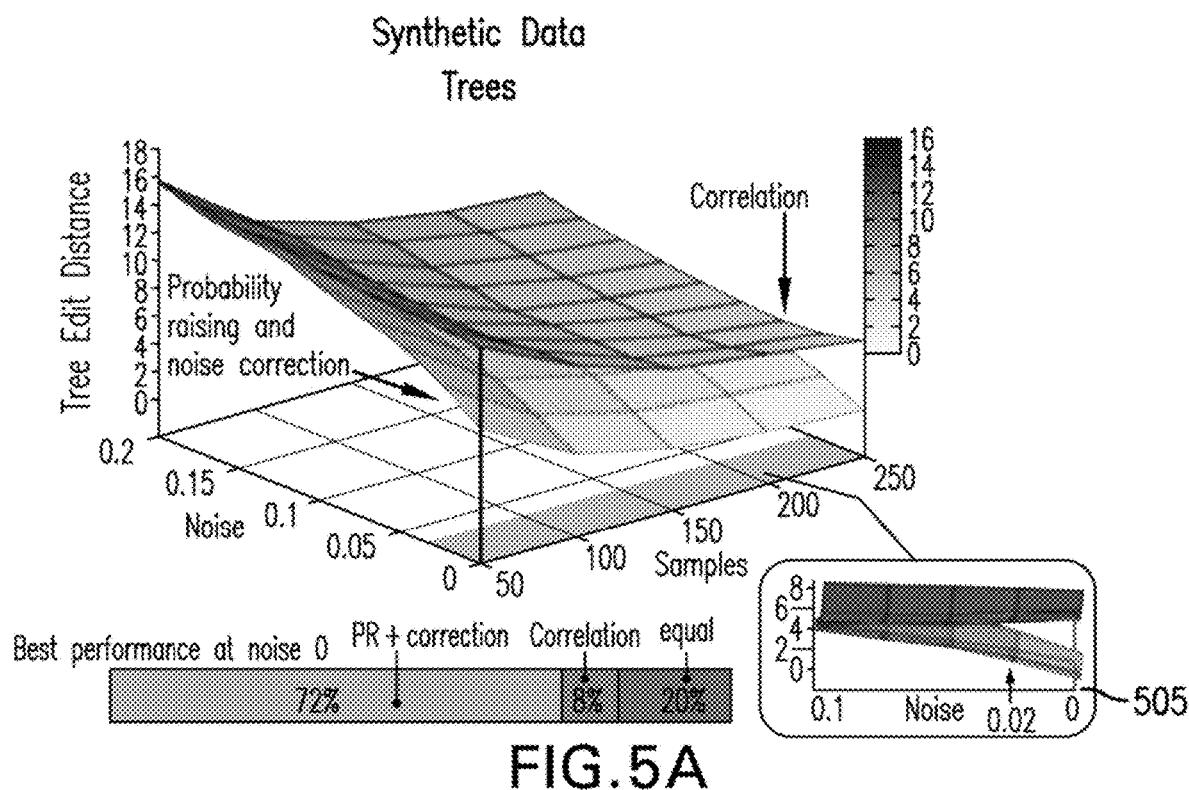
FIGS. 5A and 5B are graphs illustrating an exemplary reconstruction with noisy synthetic data and $\lambda=\frac{1}{2}$ according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION OF EXEMPLARY EMBODIMENTS

The exemplary biological notion of causality can be based on the notions of Darwinian evolution, in that it can be about an ensemble of entities (e.g., population of cells, organisms, etc.). Within this ensemble, a causal event, (e.g., c) in a member entity may result in variations (e.g., changes in genotypic frequencies); such variations can be exhibited in the phenotypic variations within the population, which can be subject to Darwinian positive, and subsequently, Malthusian negative selections, and sets the stage for a new effect event (e.g., e) to be selected, should it occur next; it can then be concluded that "▷".

While there could be other meaningful extensions of this exemplary framework (see, e.g., Reference 3), it can be sufficient to describe the causality relations implicit in the somatic evolution responsible for tumor progression. Via its very statistical nature, those relations that only reflect "Type-level Causality", but ignore "Token-level Causality", can be captured. Thus, while it can be estimated, for a population of cancer patients of a particular kind (e.g., atypical Chronic Myeloid Leukemia, aCML, patients) whether and with what probability a mutation, such as SETBP1, would cause certain other mutations, such as ASXL1 single nucleotide variants or indel to occur, it will remain silent as to whether a particular ASXL1 mutation in a particular patient was caused by an earlier SETBP1 mutation.

Exemplary Hume's regularity theory: The modern study of causation begins with the Scottish philosopher David Hume (1711-1776). According to Hume, a theory of causation could be defined axiomatically, using the following ingredients: temporal priority, implying that causes can be invariably followed by their effects (see, e.g., Reference 4), augmented by various constraints, such as contiguity, constant conjunction1, etc. Theories of this kind, that try to analyze causation in terms of invariable patterns of succession, have been referred to as regularity theories of causation.

The notion of causation has spawned far too many variants, and has been a source of acerbic debates. All these theories present well-known limitations and confusion, but have led to a small number of modern versions of commonly accepted, at least among the philosophers, frameworks. For example, the theory discussed and studied by Suppes, which is one of the most prominent causation theories, whose axioms can be expressible in probabilistic propositional modal logics, and amenable to algorithmic analysis. It can be the framework upon which the exemplary our analyses and procedures can be built.

Regularity theories can have many limitation, which are described below. Imperfect regularities: In general, it cannot be stated that causes can be invariably (e.g., without fail) followed by their effects. For example, while it can be stated state that "smoking can be a cause of lung cancer", there can still be some smokers who do not develop lung cancer.

Situations such as these can be referred to as imperfect regularities, and could arise for many different reasons. One of these which can be a very common situation in the context of cancer can involve the heterogeneity of the situations in which a cause resides. For example, some smokers may have a genetic susceptibility to lung cancer, while others do not. Moreover, some non-smokers may be exposed to other carcinogens, while others may not be. Thus, the fact that not all smokers develop lung cancer can be explained in these terms.

Irrelevance: An event that can invariably be followed by another can be irrelevant to it. (See, e.g., Reference 5). Salt that has been hexed by a sorcerer invariably dissolves when placed in water, but hexing does not cause the salt to dissolve. In fact, hexing can be irrelevant for this outcome. Probabilistic theories of causation capture exactly this situation by requiring that causes alter the probabilities of their effects.

Asymmetry: If it can be claimed that an event c causes another event e, then, typically, it can be anticipated to claim that e does not cause c, which would naturally follow from a strict temporal-priority-constraint (e.g., cause precedes effect temporally). In the context of the preceding example, smoking causes lung cancer, but lung cancer does not cause one to smoke.

Spurious Regularities: Consider a situation, not very uncommon, where a unique cause can be regularly followed by two or more effects. As an example, suppose that one observes the height of the column of mercury in a particular barometer dropping below a certain level. Shortly afterwards, because of the drop in atmospheric pressure, (the unobserved cause for falling barometer), a storm occurs. In this settings, a regularity theory could claim that the drop of the mercury column causes the storm when, indeed, it may only be correlated to it. Following common terminologies, such situations can be due to spurious correlations. There now exists an extensive literature discussing such subtleties that can be important in understanding the philosophical foundations of causality theory. (See, e.g., Reference 2).

The following exemplary notation will be used below. Atomic events, in general, are denoted by small Roman letters, such as a, b, c, . . . ; when it can be clear from the context that the event in the model can be, in fact, a genomic mutational event, it can be referred to directly using the standard biological nomenclature, for example, BRCA1, BRCA2, etc. Formulas over events will be mostly denoted by Greek letters, and their logical connectives with the usual "and" ($\wedge$), "or" ($\vee$) and "negation" ($\overline{\cdot}$) symbols. Standard operations on sets will be used as well.

Which quantity can be referred to, can be made clear from the context. In the following, $P(x)$ can denote the probability of x; $P(x \wedge y)$, the joint probability of x and y, which can be naturally extended to the notation $P(x \wedge y_1 \wedge \ldots \wedge y_n)$ for an arbitrary arity; and $P(x|y)$, the conditional probability of x given y. For example, x and y can be formulas over events.

As with causal structures, $c \triangleright e$, where c and e can be events being modeled, in order to denote the causal relation "c causes e". The notation to $\varphi \triangleright e$ can be generalized with the meaning generalized mutatis mutandis.

According to an exemplary embodiment of the present disclosure, an exemplary framework to reconstruct cumulative progressive phenomena, such as cancer progression, can be provided. The exemplary method, procedure, system, etc. can be based on a notion of probabilistic causation, which can be more suitable than correlation to infer causal structures. More specifically, it can be possible to utilize the notion of causation. (See e.g., Reference 30). Its basic intuition can be as follows: event a causes event b if (i) a occurs before b and (ii) the occurrence of a raises the probability of observing event b. Probabilistic notions of causation have been used in biomedical applications before (e.g., to find driver genes from CNV data (see e.g., Reference 20), and to extract causes from biological time series data (see e.g., Reference 22)), however, it can be believed that there was a lack of any inference of progression models in the absence of direct temporal information.

With the problem setting (see e.g., Reference 4), according to an exemplary embodiment of the present disclosure, an exemplary technique can be utilized to infer probabilistic progression trees from cross-sectional data. It can be assumed that the input can be a set of pre-selected genetic events such that the presence or the absence of each event can be recorded for each sample. Using the notion of probabilistic causation described herein, it can be possible to infer a tree whose induced distribution best describes causal structure implicit in the data.

The problem can be complicated by the presence of noise, such as the one provided by the intrinsic variability of biological processes (e.g., genetic heterogeneity) and experimental or measurement errors. To deal with this, it can be possible to utilize a shrinkage estimator to measure causation among any pair of events under consideration. (See, e.g., Reference 9). The intuition of this type of estimators can be to improve a raw estimate α (e.g., in this case probability raising) with a correction factor β (e.g., in this case a measure of temporal distance among events); a generic shrinkage estimator can be defined as θ=(1−λ)α(x)+λβ(x), where 0≤λ≤1 can be the shrinkage coefficient, x can be the input data and θ can be the estimates that should be evaluated. θ can be arbitrarily shrunk towards α or β by varying λ. The estimator can be biased. The power of shrinkage lies in the possibility of determining an optimal value for λ to balance the effect of the correction factor on the raw model estimate. This approach can be effective to regularize ill-posed inference problems, and sometimes the optimal λ can be determined analytically. (See, e.g., References 10 and 31).

According to an exemplary embodiment of the present disclosure, however, the performance of interest can be that of the reconstruction technique, rather than that of the estimator, usually measured as mean squared error. Thus, it is possible to numerically estimate the global optimal coefficient value for the reconstruction performance. Based on synthetic data, the methods, systems and computer-accessible medium according to the exemplary embodiments of the present disclosure can outperform the existing tree reconstruction algorithm. (See e.g., Reference 4). For example, the exemplary shrinkage estimator, according to an exemplary embodiment of the present disclosure, can provide, on average, an increased robustness to noisy data which can ensure that it can outperform the standard correlation-based procedure. (See e.g., id.). Further, the exemplary method, according to an exemplary embodiment of the present disclosure, can operate in an efficient way with a relatively low number of samples, and its performance can quickly converge to its asymptote as the number of samples increases. This exemplary outcome can indicate an applicability of the exemplary procedure with relatively small datasets without compromising its efficiency.

To that end, exemplary methods, computer-accessible medium, and systems, according to exemplary embodiments of the present disclosure, can be provided for modeling progression of a disease using patients' biomedical data, for example, genomics data from patients' tumor and normal cells to model progression of cancer, can be provided. Existing techniques to reconstruct models of progression for accumulative processes such as cancer, generally seek to estimate causation by combining correlation, and a frequentist notion of temporal priority. The exemplary methods, computer-accessible medium and systems can provide an exemplary framework to reconstruct such models based on the probabilistic notion of causation, which can differ fundamentally from that based on correlation. The exemplary embodiments of the methods, computer-accessible medium and systems can address the reconstruction problem in a general setting, which can be complicated by the presence of noise in the data, owing to the intrinsic variability of biological processes as well as experimental or measurement errors. To gain immunity to noise in the reconstruction performance, the exemplary methods, computer-accessible medium and systems can utilize a shrinkage estimator. The exemplary methods, computer-accessible medium and systems can be efficient even with a relatively low number of samples and its performance can quickly converge to its asymptote as the number of samples increases.

Exemplary Problem Setting

An exemplary setup of the reconstruction problem can be as follows. Assuming that a set G of n mutations (e.g., events, in probabilistic terminology) and m samples can be provided, it can be possible to represent a cross-sectional dataset as an m×n binary matrix. In this exemplary matrix, an entry (k, l)=1 if the mutation can be observed in sample k, and 0 otherwise. It should be reemphasized that such a dataset may not provide explicit information of time. The problem to be solved can be that of extracting a set of edges E yielding a progression tree T=(G ∪ {o}, E,o) from this matrix. To be more precise, it can be possible to reconstruct a proper rooted tree that can satisfy: (i) each node has at most one incoming edge in E, (ii) there may be no incoming edge to the root (iii) there may be no cycles. The root of T can be modeled using a (e.g., special) event o ∉ G, so to extract, in principle, heterogeneous progression paths, for example, forests. Each progression tree can subsume a distribution of observing a subset of mutations in a cancer sample.

Definition 1 (Tree-Induced Distribution)

Let T be a tree and α: E→[0, 1] a labeling function denoting the independent probability of each edge, T can generate a distribution where the probability of observing a sample with the set of alterations $$G^* \subseteq G \text{ is } \mathcal{P}(G^*) = \prod_{e \in E'} \alpha(e) \cdot \prod_{\substack{(u,v) \in E \\ e \in G^*, v \notin G}} [1 - \alpha(u, v)] \tag{1}$$

where E' ⊆ E can be the set of edges connecting the root o to the events in G*.

The exemplary temporal priority principle states that all causes should precede their effects. (See e.g., Reference 28). This exemplary distribution subsumes the following temporal priority: for any oriented edge (a→b) a sample can contain alteration b with probability P (a)P (b) which, roughly speaking, means that the probability of observing a can be greater than the probability of observing b.

The notion of tree-induced distribution can be used to state an important aspect which can make the reconstruction problem more difficult. The input data can be, for example, a set of samples generated, preferably, from an unknown distribution induced by an unknown tree that can be intended to be reconstructed. However, in some cases, it can be possible that no tree exists whose induced distribution generates exactly those data. When this happens, the set of observed samples can slightly diverge from any tree-induced distribution. To model these situations, a notion of noise can be introduced, which can depend on the context in which data can be gathered.

Exemplary Oncotree Approach

Previous method described how to extract progression trees, named "oncotrees", initially applied to static CNV data. (See e.g., Reference 4). In these exemplary trees, nodes can represent CNV events and edges correspond to possible progressions from one event to the next.

The reconstruction problem can be exactly as described above, and each tree can be rooted in the special event o. The choice of which edge to include in a tree can be based on the exemplary estimator $$w_{a \to b} = \log\left[\frac{\mathcal{P}(a)}{\mathcal{P}(a)+\mathcal{P}(b)} \cdot \frac{\mathcal{P}(a,b)}{\mathcal{P}(a)\mathcal{P}(b)}\right], \quad (2)$$

which can assign, to each edge a→b, a weight accounting for both the relative and joint frequencies of the events, thus measuring correlation. The exemplary estimator can be evaluated after including o to each sample of the dataset. In this definition the rightmost term can be the likelihood ratio (e.g., symmetric) for a and b occurring together, while the leftmost can be the asymmetric temporal priority measured by rate of occurrence. This implicit form of timing can assume that, if a can occur more often than b, then it likely can occur earlier, thus satisfying the inequality $$\frac{\mathcal{P}(a)}{\mathcal{P}(a)+\mathcal{P}(b)} > \frac{\mathcal{P}(b)}{\mathcal{P}(a)+\mathcal{P}(b)}.$$

An exemplary oncotree can be the rooted tree whose total weight (e.g., sum of all the weights of the edges) can be maximized, and can be reconstructed in $O(|G|^2)$ steps using Edmond's seminal result. (See e.g., Reference 6). By the exemplary construction, the resulting exemplary graph can be a proper tree rooted in o: each event can occur only once, confluences can be absent, for example, any event can be caused by at most one other event. The branching trees method has been used to derive progression trees for various cancer datasets (see, e.g., References 18, 21 and 27), and even though several extensions of the method exist (see, e.g., References 2 and 5), it is one of the most used methods to reconstruct trees and forests.

Exemplary Probabilistic Approach to Causation

Before introducing the notion of causation, upon which the exemplary procedure can be based, the approach to probabilistic causation is described. An extensive discussion on this topic, its properties and its problems has been previously discussed (See e.g., References 16 and 30)

Exemplary Definition 2 (Probabilistic Causation (See, e.g., Reference 30))

For any two events c and e, occurring respectively at times $t_c$ and $t_e$, under the assumptions that $0<P(c),P(e)<1$, the event c causes the event e if it occurs before the effect and the cause raises the probability of the effect, for example:

$$t_c < t_e \text{ and } \mathcal{P}(e|e) > \mathcal{P}(e|\bar{c}) \quad (3)$$

The exemplary input of the exemplary procedure can include cross-sectional data and no information about the timings to may be available. Thus the probability raising ("PR") property can be considered as a notion of causation, for example, P(e c)>P(e I−6'). Provided below is a review some exemplary properties of the PR.

Exemplary Proposition 1 (Dependency)

Whenever the PR holds between two events a and b, then the events can be statistically dependent in a positive sense, that can be, for example:

$$\mathcal{P}(b|a) > \mathcal{P}(b|\bar{a}) \iff \mathcal{P}(a,b) > \mathcal{P}(a)\mathcal{P}(b). \quad (4)$$

This property, as well as Property 2, is a well-known fact of the PR. Notice that the opposite implication holds as well. When the events a and b can still be dependent but in a negative sense, for example, P (a, b)<P (a)P (b), the PR does not hold, for example, $P(b|a)<P(b|\bar{a})$.

It can be possible to use the exemplary PR to determine whether a specific a pair of events a and b satisfy a causation relation. Thus facilitating the conclusion when the event a causes the event b, and a can be placed before b in the progression tree. Unfortunately, it may not be possible to simply state that a causes b when $P(b|a)<P(b|\bar{a})$ since, although PR can be known not to be symmetric, it holds.

Exemplary Proposition 2 (Mutual PR)

Proposition 2 (Mutual PR).
$$\mathcal{P}(b|a) > \mathcal{P}(b|\bar{a}) \iff \mathcal{P}(a|b) > \mathcal{P}(a|\bar{b}).$$

For example, if a raises the probability of observing b, then b raises the probability of observing a too.

Nevertheless, to determine causes and effects among the genetic events, it can be possible use the confidence degree of probability rising to decide the direction of the causation relationship between pairs of events. In other words, if a raises the probability of b more than the other way around, then a can be a more likely cause of b than b of a. As discussed, the PR may not be symmetric, and the direction of probability rising can depend on the relative frequencies of the events.

Exemplary Proposition 3 (Probability Raising and Temporal Priority)

For any two events a and b such that the probability raising $P(a|b)>P(a|\bar{b})$ holds, the following can be provided $$\mathcal{P}(a) > \mathcal{P}(b) \iff \frac{\mathcal{P}(b|a)}{\mathcal{P}(b|\bar{a})} > \frac{\mathcal{P}(a|b)}{\mathcal{P}(a|\bar{b})}. \quad (5)$$

For example, according to the PR model, given that the PR holds between two events, a raises the probability of b more than b raises the probability of a, if a can be observed more frequently than b. The ratio can be used to assess the PR inequality. An exemplary proof of this proposition can be found in the Appendix. From this exemplary result, it follows that if the timing of an event can be measured by the rate of its occurrence (e.g., P(a)>P(b) can imply that a happens before b), this exemplary notion of PR subsumes the same notion of temporal priority induced by a tree. Further, this can be the temporal priority made explicit in the coefficients of Desper's. Given these exemplary results, it can be possible to define the following notion of causation.

Exemplary Definition 3

For example, a causes b if a can be a probability raiser of b, and it occurs more frequently: $\mathcal{P}(b|a) > \mathcal{P}(b|\bar{a})$ and $\mathcal{P}(a) > \mathcal{P}(b)$.

Further, it is possible to utilize the conditions for the exemplary PR to be computable: every mutation a should be observed with probability strictly $0<P(a)<1$. Moreover, each pair of mutations (a, b) can be reviewed to be distinguishable in terms of PR, that can be P(a b)<1 or P(b I<1 similarly to the above condition. Any non-distinguishable pair of events can be merged as a single composite event. From now on, it can be assumed that these conditions have been verified.

Extracting progression trees with Probability Raising and Shrinkage Estimator

The exemplary procedure can be similar to Desper's algorithm, with one of the differences being an alternative weight function based on a shrinkage estimator.

Definition 4 (Shrinkage Estimator)

It is possible to define the shrinkage estimator m a→b of the confidence in the causation relationship from a to b as $$m_{a \to b} = (1 - \lambda)\alpha_{a \to b} + \lambda\beta_{a \to b}, \quad (6)$$

where $0 \leq \lambda \leq 1$ and $$\alpha_{a \to b} = \frac{\mathcal{P}(b \mid a) - \mathcal{P}(b \mid \bar{a})}{\mathcal{P}(b \mid a) + \mathcal{P}(b \mid \bar{a})} \qquad \beta_{a \to b} = \frac{\mathcal{P}(a,b) - \mathcal{P}(a)\mathcal{P}(b)}{\mathcal{P}(a,b) + \mathcal{P}(a)\mathcal{P}(b)}. \quad (7)$$

This exemplary estimator can combine a normalized version of the PR, the raw model estimate α, with the correction factor β. The exemplary shrinkage can improve the performance of the overall reconstruction process, not limited to the performance of the exemplary estimator itself. For example, m can induce an ordering to the events reflecting the confidence for their causation. However, this exemplary framework may not imply any performance bound for the, for example, mean squared error of m. The exemplary shrinkage estimator can be an effective way to get such an ordering when data is noisy. In the exemplary system, method and computer-accessible medium a pairwise matrix version of the estimator can be used.

---

Algorithm 1 Tree-alike reconstruction with shrinkage estimator

1: consider a set of genetic events G = {$g_1, \ldots, g_n$} plus a special event ◊, added to each sample of the dataset;

2: define a n × n matrix M where each entry contains the shrinkage estimator $$m_{i \to j} = (1 - \lambda) \cdot \frac{\mathcal{P}(j \mid i) - \mathcal{P}(j \mid \bar{i})}{\mathcal{P}(j \mid i) + \mathcal{P}(j \mid \bar{i})} + \lambda \cdot \frac{\mathcal{P}(i,j) - \mathcal{P}(i)\mathcal{P}(j)}{\mathcal{P}(i,j) + \mathcal{P}(i)\mathcal{P}(j)}$$

according to the observed probability of the events i and j;

3: [PR causation] define a tree $\mathcal{T} = (G \cup \{\diamond\}, E, \diamond)$ where (i → j) ∈ E for i, j ∈ G if and only if:

$$m_{i \to j} > 0 \text{ and } m_{i \to j} > m_{j \to i} \text{ and } \forall i' \in G, m_{i,j} > m_{i',j}.$$

4: [Correlation filter] define $G_j = \{g_i \in G \mid \mathcal{P}(i) > \mathcal{P}(j)\}$, replace edge (i → j) ∈ E with edge (◊ → j) if, for all $g_w \in G_j$, it holds $$\frac{1}{1 + \mathcal{P}(j)} > \frac{\mathcal{P}(w)}{\mathcal{P}(w) + \mathcal{P}(j)} \frac{\mathcal{P}(w,j)}{\mathcal{P}(w)\mathcal{P}(j)}.$$

---

Exemplary Raw Estimator and the Correction Factor

By considering, for example, only the exemplary raw estimator α, it can be possible to include an edge (a→b) in the tree consistently in terms of (i) Definition 3 and (ii) if α can be the best probability raiser for b. When P(a)=P(b), the events a and b can be indistinguishable in terms of temporal priority. Thus α may not be sufficient to decide their causal relation, if any. This intrinsic ambiguity becomes unlikely when β can be introduced, even if it can still be possible.

This exemplary formulation of a can be a monotonic normalized version of the PR ratio.

Proposition 4 (Monotonic normalization).

For any two events a and b we have $$\mathcal{P}(a) > \mathcal{P}(b) \Leftrightarrow \frac{\mathcal{P}(b \mid a)}{\mathcal{P}(b \mid \bar{a})} > \frac{\mathcal{P}(a \mid b)}{\mathcal{P}(a \mid \bar{b})} \Leftrightarrow \alpha_{a \to b} > \alpha_{b \to a}. \quad (8)$$

This exemplary raw model estimator can satisfy $-1 \leq a_{a \to b}$, $a_{b \to a} \leq 1$ and can have the following meaning: when it tends to −1, the pair of events can appear disjointly (e.g., they can show an anti-causation pattern in the observations), when it tends to 0, no causation or anti-causation can be inferred, and the two events can be statistically independent. And when it tends to 1, causation relationship between the two events can be robust. Therefore, a can provide a quantification of the degree of confidence for a given causation relationship, with respect to probability rising.

However, α does not provide a general criterion to disambiguate among groups of candidate parents of a given node. A specific case can be shown in which α may not be a sufficient estimator. For instance, a set of three events can be provided that can be involved in a causal linear path: a→b→c. In this case, when evaluating the candidate parents a and b for c, the following can be provided: $a_{a \to c} = a_{b \to c} = 1$. Accordingly, it can be possible to infer that $t_a < t_c$ and $t_b < t_c$, for example, a partial ordering, which may not help to disentangle the relation among a and b with respect to c.

In this exemplary case, the β coefficient can be used to determine which of the two candidate parents can occur earlier. In general, such a correction factor can provide information on the temporal distance between events, in terms of statistical dependency. In other words, the higher the coefficient, the closer two events can be. The exemplary shrinkage estimator m can then result in a shrinkable combination of the raw PR estimator α and of the β correction factor, which can satisfy an important property.

Exemplary Proposition 5 (Coherence in Dependency and Temporal Priority)

The β correction factor can be symmetrical, and can subsume the same notion of dependency of the raw estimator α, that can be, for example:

$$\mathcal{P}(a,b) > \mathcal{P}(a)\mathcal{P}(b) \Leftrightarrow \alpha_{a \to b} > 0 \beta_{a \to b} > 0 \text{ and } \beta_{a \to b} = \beta_{b \to a}. \quad (9)$$

Thus, the correction factor can respect the temporal priority induced by the raw estimator α.

The Correlation Filter.

Following Desper's approach, it can be possible to add a root o with P(o)=1 to separate different progression paths, which can then be represented as different sub-trees rooted in o. the exemplary system, method and computer-accessible medium initially builds a unique tree by using m. Then, the correlation-alike weight between any node j and o can be computed as, for example:

$$\frac{\mathcal{P}(\diamond)}{\mathcal{P}(\diamond)+\mathcal{P}(j)}\frac{\mathcal{P}(\diamond,j)}{\mathcal{P}(\diamond)\mathcal{P}(j)} = \frac{1}{1+\mathcal{P}(j)}.$$

If this quantity can be greater than the weight of j with each upstream connected element i, it can be possible to substitute the edge (i j) with the edge (o→j). It can then be possible to use a correlation filter because it would make no sense to ask whether o was a probability raiser for j, besides the technical fact that a may not be defined for events of probability 1. For example, this exemplary filter can imply a non-negative threshold for the shrinkage estimator, when a cause can be valid.

Exemplary Theorem 1 (Independent Progressions)

Let $G^* = \{a1, \ldots, ak\} \subset G$ a set of k events which can be candidate causes of some $b \notin G^*$, for example, $P(a_i) > P(b)$ and $m_{ai} \to b > 0$ for any $a_i$. There exist $1 < \gamma < 1/P(a_i)$ and $S > 0$ such that b determines an independent progression tree in the reconstructed forest, for example, the edge o b can be picked by the exemplary system, method and computer-accessible medium, if for any $a_i$ $$\mathcal{P}(a_i, b) < \gamma [\mathcal{P}(a_i) \mathcal{P}(b)] + \delta. \tag{10}$$

The proof of this Theorem can be found in the enclosed Appendix. What can be indicated by this exemplary theorem can be that, by examining the level of statistical dependency of each pair of events, it can be possible to determine how many trees can compose the reconstructed forest. Further, it can suggest that the exemplary system, method and computer-accessible medium can be defined by first processing the correlation filter, and then using m to build the independent progression trees in the forest. Thus, the exemplary procedure/algorithm can be used to reconstruct well-defined trees in the sense that no transitive connections and no cycles can appear.

Exemplary Theorem 2 (Procedure Correctness)

The exemplary system, method and computer-accessible medium can reconstruct a well-defined tree T without disconnected components, transitive connections and cycles.

The proof of this Theorem follows immediately from Proposition 3 and can be found in the enclosed Appendix.

Exemplary Performance of Procedure and Estimation of Optimal Shrinkage Coefficient Synthetic data can be used to evaluate the performance of the exemplary system, method and computer-accessible medium as a function of the shrinkage coefficient A. Many distinct synthetic datasets were created for this. The procedure performance was measured in terms of Tree Edit Distance ("TED") (see, e.g., Reference 35). For example, the exemplary minimum-cost sequence of node edit operations (e.g., relabeling, deletion and insertion) that transforms the reconstructed trees into the ones generating the data.

Exemplary Synthetic Data Generation

Synthetic datasets were generated by sampling from various random trees, constrained to have depth log(JG1), since wide branches can be hard to reconstruct than straight paths. Unless differently specified, in all the experiments, 100 distinct random trees, or forests, accordingly to the test to perform of 20 events each were used. This is a fairly reasonable number of events, and can be in line with the usual size of reconstructed trees. (See, e.g., References 13, 24, 26 and 29). The scalability of the reconstruction performance was tested against the number of samples by letting IGI range from 50 to 250, with a step of 50, and by replicating 10 independent datasets for each parameters setting.

A form of noise was included in generating the datasets, so to account for (i) the realistic presence of biological noise (e.g., the one provided by bystander mutations, genetic heterogeneity, etc.) and (ii) experimental or measurement errors. A noise parameter $0 < v < 1$ can denote the probability that any event assumed a random value (e.g., with uniform probability), after sampling from the tree-induced distribution'. This can introduce both false negatives and false positives in the datasets. Algorithmically, this exemplary process can generate, on average, $|G| v/2$ random entries in each sample (e.g. with v=0.1 there can be, on average, one error per sample). It can be possible to assess whether these noisy samples can mislead the reconstruction process, even for low values of v.

In what follows, it can be possible to refer to datasets generated with $v > 0$ as noisy synthetic dataset. In the exemplary experiments, v can be discretized by 0.025, (e.g., about 2.5% noise).

Exemplary Optimal Shrinkage Coefficient

Given that the events can be dependent on the topology to reconstruct, it was not possible to determine analytically an optimal value for the shrinkage. The exemplary assumption that noise can be uniformly distributed among the events may appear simplistic. In fact some events may be more robust, or easy to measure, than others. For example, works more sophisticated noise distributions can be considered coefficient by using, for example, the standard results in shrinkage statistics. (See e.g., Reference 9). Therefore, an empirical estimation of the optimal A can be used, both in the case of trees and forests.

As shown in FIG. 1, the variation in the performance of the exemplary system, method and computer-accessible medium the exemplary system, method and computer-accessible medium as a function of A can be indicated, for example, in the specific case of datasets with 150 samples generated on tree topologies. The exemplary optimal value (e.g., lowest TED) for noise-free datasets (e.g., v=0) can be obtained for $\lambda \to 0$, whereas for the noisy datasets a series of U-shaped curves can indicate a unique optimum value for $\lambda \to \frac{1}{2}$, with respect to all the levels of noise. Identical results can be obtained when dealing with forests. Further, exemplary experiments show that the estimation of the optimal $\lambda$ may not be dependent on the number of samples in the datasets. (See FIG. 2). An exemplary analysis was limited to datasets with the typical sample size that can be characteristic of data currently available. In other words, if the noise-free case can be considered, the best performance can be obtained by, for example, shrinking m to the PR model raw estimate α, for example:

$$m_{a \to b} \stackrel{\lambda \to 0}{\approx} \alpha_{a \to b} \tag{11}$$

which can be obtained by setting $\lambda$ to a very small value, e.g. $10^{-2}$, in order to consider the contribution of the correction factor too. Conversely, when considering the case of $v > 0$, the best performance can be obtained by averaging the shrinkage effect, as for example:

$$m_{a \to b} \stackrel{\lambda=1/2}{=} \frac{\alpha_{a \to b}}{2} + \frac{\beta_{a \to b}}{2}. \quad (12)$$

These exemplary results can indicate that, in general, a unique optimal value for the shrinkage coefficient can be determined.

FIGS. 2A and 2B shown an optimal λ with datasets of different sizes similar to FIG. 1, with sample sizes of 50 and 250 respectively. The estimation of the optimal shrinkage coefficient λ is irrespective of sample size.

Exemplary Performance of Procedure Compared to Oncotrees

As shown in exemplary graphs of FIGS. 3A and 3B, the performance of the exemplary system, method and computer-accessible medium (element 305) can be compared with oncotrees (element 310), for the case of noise-free synthetic data. In this exemplary case, the optimal shrinkage coefficient was used in equation (11): λ→0. FIGS. 4A and 4B show diagrams of an example of a reconstructed tree where, for the noise-free case, whereas the exemplary system, method and computer-accessible medium can infer the correct tree while oncotrees mislead a causation relation. Examples of reconstruction from a dataset by the Target tree (see FIG. 4A, where numbers represent the probability of observing a mutation while generating sample), with v=0. The oncotree (shown in FIG. 4B) misleads the correct causal relation for the double-circled mutation. It evaluates w=0 for the real causal edge and w=0.14 for the wrong one. The exemplary system, method and computer-accessible medium, according to an exemplary embodiment of the present disclosure, can infer the correct tree.

In general, the TED of the exemplary system, method and computer-accessible medium can be, on average, bounded above by the TED of the oncotrees, both in the case of trees (see FIG. 3A) and forests (see FIG. 3B). For trees, with a low number of samples (e.g., 50) the average TED of the exemplary system, method and computer-accessible medium can be around 7, whereas for Desper's technique can be around 13. The exemplary performance of both procedures can improve as long as the number of samples can be increased: the exemplary system, method and computer-accessible medium has the best performance (e.g., TED≈0) with 250 samples, while oncotrees have TED around 6. When forests can be considered, the difference between the performances of the procedures can slightly reduce, but also in this case the exemplary system, method and computer-accessible medium clearly outperforms branching trees.

The exemplary improvement due to the increase in the sample set size tends toward a plateau, and the initial TED for the exemplary estimator is close to the plateau value. Thus, this can indicate that the exemplary system, method and computer-accessible medium has good performance with few samples. This can be an important result, particularly considering the scarcity of available biological data.

Figure 5B:
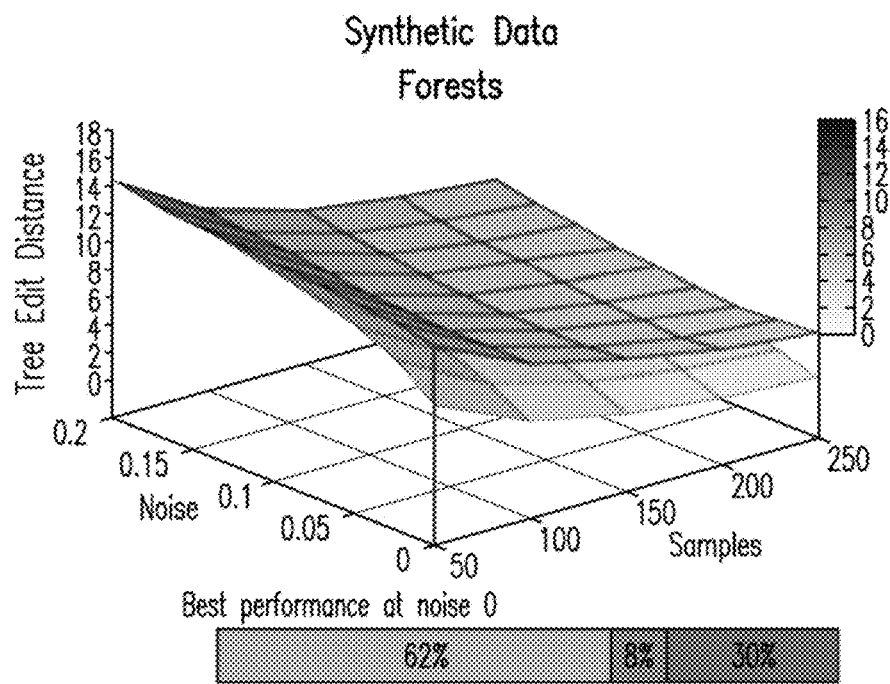

In the exemplary graphs of FIGS. 5A and 5B, the comparison is extended to noisy datasets. In this exemplary case, the optimal shrinkage coefficient in equation (12): λ→½ can be used. The exemplary results can confirm what can be observed in the case of noise-free data, as exemplary the exemplary system, method and computer-accessible medium outperforms Desper's branching trees up to v=0.15 (e.g., v=0.1), for all the sizes of the sample sets. (See e.g., element 505). The bar plots represent the percentage of times the best performance is achieved at v=0.

Exemplary Performance on Cancer Datasets

The exemplary results above indicate that the exemplary method, according to an exemplary embodiment of the present disclosure, outperforms oncotrees. The exemplary procedure was tested on a real dataset of cancer patients.

To test the exemplary reconstruction procedure on a real dataset, it was applied to the ovarian cancer dataset made available within the oncotree package. (See, e.g., Reference 4). The data was collected through the public platform SKY/M-FISH (see, e.g., Reference 23), which can be used to facilitate investigators to share and compare molecular cytogenetic data. The data was obtained by using the Comparative Genomic Hybridization technique ("CGH") on samples from papillary serous cystadenocarcinoma of the ovary. This exemplary procedure uses fluorescent staining to detect CNV data at the resolution of chromosome arms. This type of analysis can be performed at a higher resolution, making this dataset rather outdated. Nevertheless, it can still serve as a good test-case for the exemplary approach. The seven most commonly occurring events can be selected from the approximate 87 samples, and the set of events can be the following gains and losses on chromosomes arms G={8q+, 3q+,1q+,5q−, 4q−, 8p−, Xp−}, where for example, 4q can denote a deletion of the q arm of the 4th chromosome.

Figure 6A:
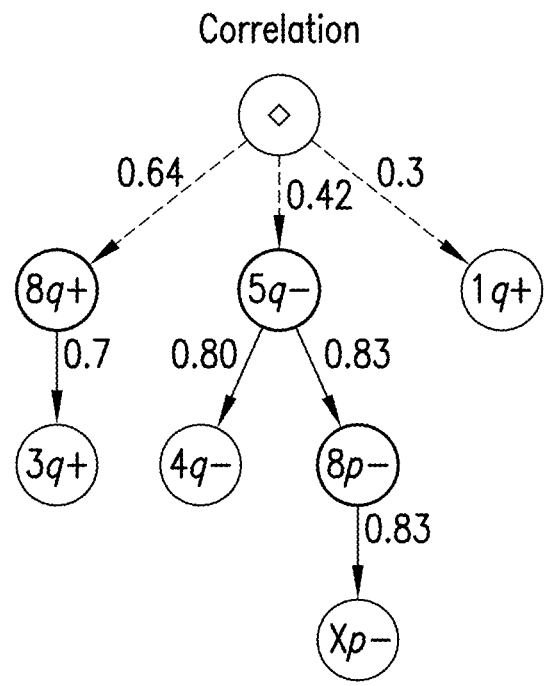
FIGS. 6A and 6B are graphs of an exemplary oncotree reconstruction of an ovarian cancer progression according to an exemplary embodiment of the present disclosure.
Figure 6B:
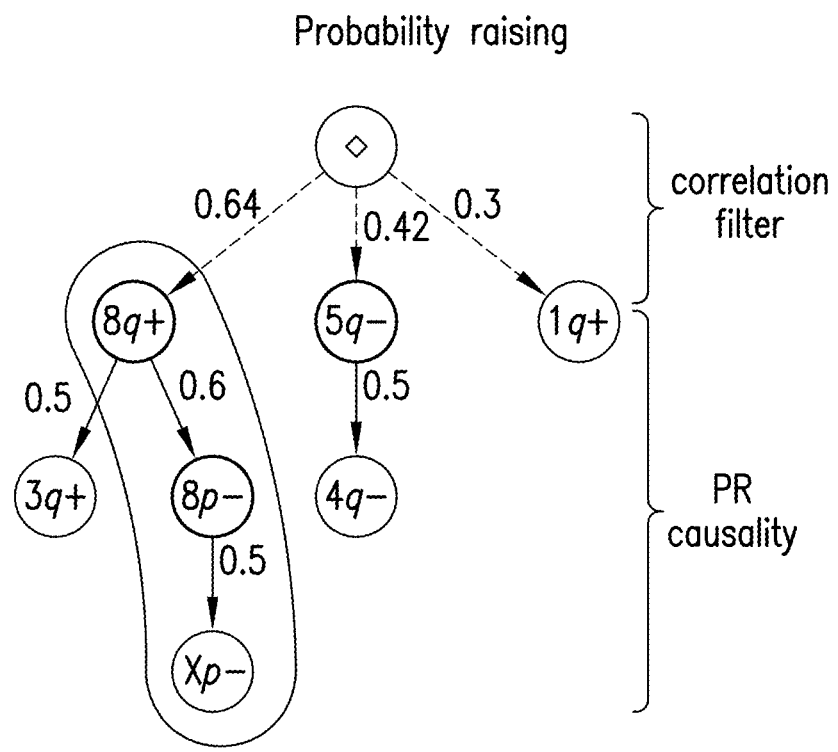

In the exemplary diagrams of FIGS. 6A and 6B, the trees reconstructed by the two approaches can be compared. The exemplary procedure, according to the exemplary embodiment of the present disclosure, can differ from Desper's in terms of how it predicts by predicting the causal sequence of alterations

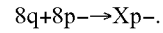
8q+8p−→Xp−.

For example, all the samples in the dataset can be generated by the distribution induced by the recovered tree. Thus facilitating the consideration of this exemplary dataset as noise-free; algorithmically, this facilitates the use of the exemplary estimator for λ→0).

While, a biological interpretation for this result is not provided, it is known that common cancer genes reside in these regions (e.g., the tumor suppressor gene PDGFR on 5q, and the oncogene MYC on 8q, and loss of heterozygosity on the short arm of chromosome 8 can be very common. Recently, evidence has been reported that location 8p contains many cooperating cancer genes. (See, e.g., Reference 34).

To assign a confidence level to these inferences, both parametric and non-parametric bootstrapping methods can be applied to the exemplary results. (See, e.g., Reference 7). For example, these tests consists of using the reconstructed trees (in the parametric case), or the probability observed in the dataset (in the non-parametric case) to generate new synthetic datasets, and then reconstruct the progressions again. (See, e.g., Reference 8). The confidence can be given by the number of times the trees shown in FIGS. 6A and 6B are reconstructed from the generated data. A similar approach can be used to estimate the confidence of every edge separately. For oncotrees the exact tree can be obtained about 83 times out of about 1000 non-parametric resamples, so its estimated confidence can be about 8.3%. For the exemplary procedure, according to the exemplary embodiment of the present disclosure, the confidence can be about 8.6%. In the non-parametric case, the confidence of oncotrees can be about 17% while that of the exemplary procedure can be much higher, for example, 32%. For the non-parametric case, an exemplary edge confidence is shown in the exemplary tables of FIGS. 7A and 7B. For example, the exemplary procedure, according to an exemplary embodiment of the present disclosure, can reconstruct the inference 8q+8p− with high confidence (confidence of about 62%, and 26% for 5q−8p−), while the confidence of the edge 8q+5q− can be only 39%, almost the same as 8p−8q+(confidence of about 40%). FIGS. 7A and 7B show the frequency of edge occurrences in the non-parametric bootstrap test, for the trees shown in FIGS. 6A and 6B. Element 705 represents <0.4%, element 710 represents 0.4%-0.8%, and element 715 represents >0.8%. Bold entries are the edges received using the exemplary system, method and computer-accessible medium.

Figure 8A:
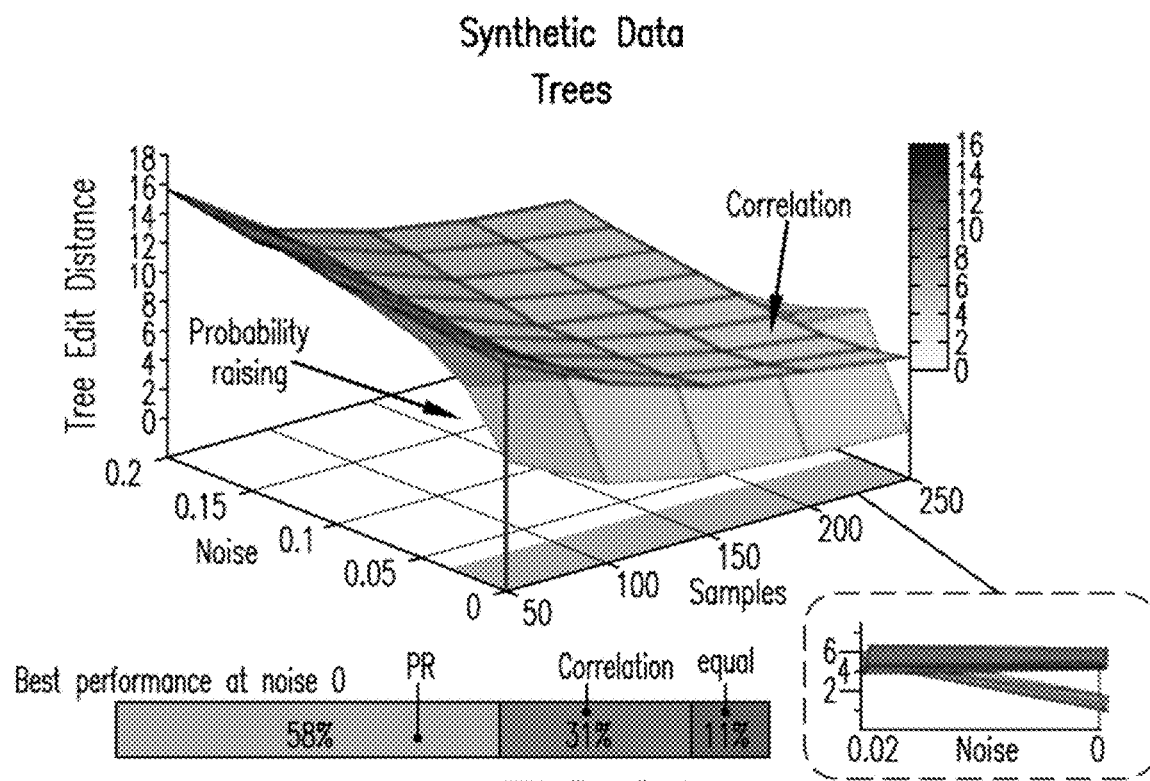
FIGS. 8A and 8B are graphs illustrating the exemplary reconstruction with the noisy synthetic data where $\lambda=0$ according to an exemplary embodiment of the present disclosure.
Figure 8B:
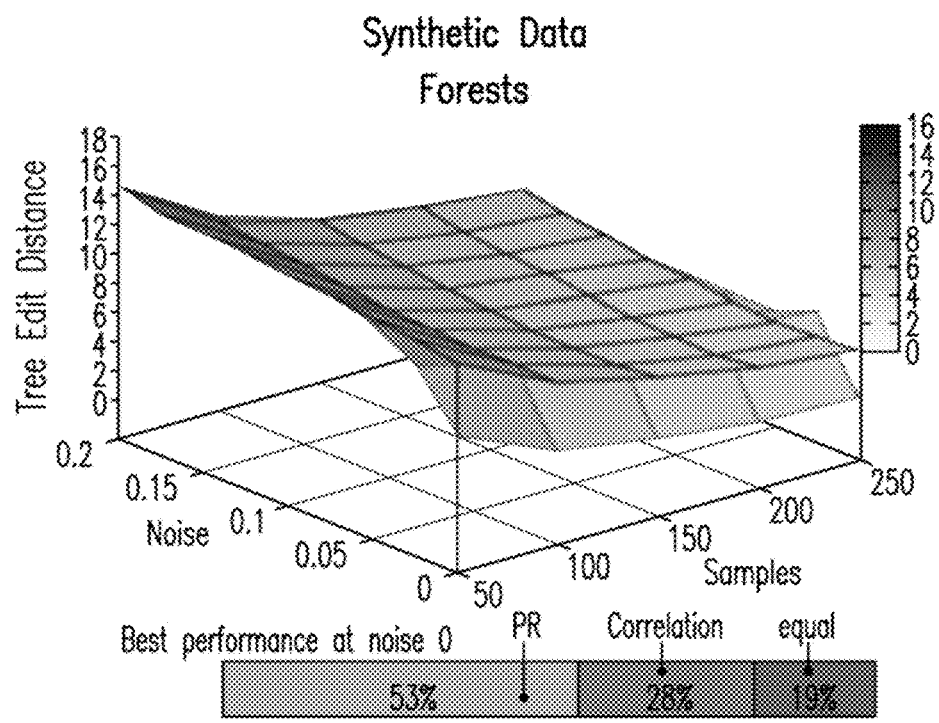

FIGS. 8A and 8B illustrate exemplary graphs providing an exemplary reconstruction with noisy synthetic data and $\lambda \rightarrow 0$. The exemplary settings of the exemplary experiments are the same as those used for FIG. 5, but the estimator is shrunk to a by $\lambda \rightarrow 0$ (e.g., $\lambda = 0.01$). For example, in element 805, the performance of the exemplary system, method and computer-accessible medium can converge with the Exemplary Desper's for v approximately equal to 0.01. Thus it is faster than the case where $\lambda$ is approximately equal to ½.

Exemplary Analysis of Other Datasets

The differences between the reconstructed trees can also be based on datasets of gastrointestinal and oral cancer. (See, e.g., References 13 and 26). In the case of gastrointestinal stromal cancer, among the 13 CGH events considered (see e.g., Reference 13), for gains on 5p, 5q and 8q, losses on 14q, 1p, 15q, 13q, 21q, 22q, 9p, 9q, 10q and 6q, the branching trees can identify the path progression as, for example:
1p−15q−−+13q−−+21q−
while the exemplary system, method and computer-accessible medium can reconstruct the branch as, for example:
1p−−→15q−1p−→13q−→21q−

In the case of oral cancer, among the 12 CGH events considered for gains on 8q, 9q, 11q, 20q, 17p, 7p, 5p, 20p and 18p, losses on 3p, 8p and 18q, the reconstructed trees differ since oncotrees identifies the path as, for example:
8q+→20q+→20p+

These examples show that the exemplary the exemplary system, method and computer-accessible medium can provide important differences in the reconstruction compared to the branching trees.

Exemplary Discussion

As described herein, an exemplary framework for the reconstruction of the causal topologies, according to an exemplary embodiment of the present disclosure, has been described that can provide extensive guidance on a cumulative progressive phenomena, based on the probability raising notion of probabilistic causation. Besides such a probabilistic notion, the use of an exemplary shrinkage estimator has been discussed for efficiently unraveling ambiguous causal relations, often present when data can be noisy. Indeed, an effective exemplary procedure can be described for the reconstruction of a tree or, in general, forest models of progression which can combine, for the first time, probabilistic causation and shrinkage estimation.

Such exemplary procedure was compared with a standard approach based on correlation, to show that that the exemplary method can outperform the state of the art on synthetic data, also exhibiting a noteworthy efficiency with relatively small datasets. Furthermore, the exemplary procedure has been tested on low-resolution chromosomal alteration cancer data. This exemplary analysis can indicate that the exemplary procedure, system and computer accessible medium, according to an exemplary embodiment of the present disclosure, can infer, with high confidence, exemplary causal relationships which would remain unpredictable by basic correlation-based techniques. Even if the cancer data that used can be coarse-grained, and does not account for, for example, small-scale mutations and epigenetic information, this exemplary procedure can be applied to data at any resolution. In fact, it can require an input set of samples containing some alterations (mutations in the case of cancer), supposed to be involved in a certain causal process. The exemplary results of the exemplary procedure can be used not only to describe the progression of the process, but also to classify. In the case of cancer, for instance, this genome-level classifier could be used to group patients and to set up a genome-specific therapy design.

Further complex models of progression can be inferred with probability raising, for example, directed acyclic graphs. (See, e.g., References 1, 11 and 12). These exemplary models, rather than trees, can explain the common phenomenon of preferential progression paths in the target process via, for example, confluence among events. In the case of cancer, for example, these models can be more suitable than trees to describe the accumulation of mutations.

Further, the exemplary shrinkage estimator itself can be modified by, for example, introducing, different correction factors. In addition, regardless of the correction factor, an analytical formulation of the optimal shrinkage coefficient can be provided with the hypotheses which can apply to the exemplary problem setting. (See e.g., References 10 and 31).

Exemplary Simplified Framework

The currently existing literature lacks a framework readily applicable to the problem of reconstructing cancer progression, as governed by somatic evolution; however, each theory has ingredients that can be highly promising and relevant to the problem.

Each of the existing theories faces various difficulties, which can be rooted primarily in the attempt to construct a framework in its full generality: each theory aims to be both necessary and sufficient for any causal claim, in any context. In contrast, the exemplary system, method, and computer-accessible medium, according to an exemplary embodiment of the present disclosure simplifies the problem by breaking the task into two: first, defining a framework for Suppes' prima facie notion, though it admits some spurious causes and then dealing with spuriousness by using a combination of tools, for example, Bayesian, empirical Bayesian, regularization. The framework can be based on a set of conditions that can be necessary even though not sufficient for a causal claim, and can be used to refine a prima facie cause to either a genuine or a spurious cause (e.g., or even ambiguous ones, to be treated as plausible hypotheses which can be refuted/validated by other means).

Statement of Assumptions.

Along with the described interpretation of causality, throughout this document, the following exemplary simplifying assumptions can be made:

(i) All causes involved in cancer can be expressed by monotonic Boolean formulas. For example, all causes can be positive and can be expressed in CNF where all literals occur only positively. The size of the formula and each clause therein can be bounded by small constants.

(ii) All events can be persistent. For example, once a mutation has occurred, it cannot disappear. Hence, situations where $P(e|c) < P(e|\bar{c})$ are not modelled.

(iii) Closed world. All the events which can be causally relevant for the progression can be observable and the observation can significantly describe the progressive phenomenon.

(iv) Relevance to the progression. All the events have probability strictly in the real open interval (e.g., 0, 1), for example, it can be possible to asses if they can be relevant to the progression.

(v) Distinguishability. No two events appear equivalent, for example, they can neither be both observed nor both missing simultaneously.

Exemplary Learning of Bayesian Networks ("BN"s)

A BN can be a statistical model that succinctly represents a joint distribution over n variables, and encodes it in a direct acyclic graph over n nodes (e.g., one per variable). In BNs, the full joint distribution can be written as a product of conditional distributions on each variable. An edge between two nodes, A and B, can denote statistical dependence, $P(A \wedge B) \neq P(A)P(B)$, no matter on which other variables can be conditioned on (e.g., for any other set of variables C it holds $P(A \wedge B|C) \neq P(A|C)P(B|C)$). In such an exemplary graph, the set of variables connected to a node X can determine its set of "parent" nodes $\pi(X)$. Note that a node cannot be both ancestor and descendant of another node, as this would cause a directed cycle.

The joint distribution over all the variables can be written as $\Pi_x P(X|\pi(X))$. If a node has no incoming edges (e.g., no parents), its marginal probability can be $P(X)$. Thus, to compute the probability of any combination of values over the variables, the conditional probabilities of each variable given its parents can be parameterized. If the variables can be binary, the number of parameters in each conditional probability table can be locally of exponential size (namely, $2^{|\pi(X)|}-1$). Thus, the total number of parameters needed to compute the full joint distribution can be of size $\Sigma_X 2^{|\pi(X)|-1}$, which can be considerably less than $2^n - 1$.

A property of the graph structure can be, for each variable, a set of nodes called the Markov blanket which can be defined so that, conditioned on it, this variable can be independent of all other variables in the system. It can be proven that for any BN, the Markov blanket can consist of a node's parents, children as well as the parents of the children.

The usage of the symmetrical notion of conditional dependence can introduce important limitations of structure learning in BNs. In fact, note that edges $A \rightarrow B$ and $B \rightarrow A$ denote equivalent dependence between A and B. Thus distinct graphs can model the exact same set of independence and conditional independence relations. This yields the notion of Markov equivalence class as a partially directed acyclic graph, in which the edges that can take either orientation can be left undirected. A theorem proves that two BNs can be Markov equivalent when they have the same skeleton and the same v-structures; the former being the set of edges, ignoring their direction (e.g., $A \rightarrow B$ and $B \rightarrow A$ constitute a unique edge in the skeleton) and the latter being all the edge structures in which a variable has at least two parents, but those do not share an edge (e.g., $A \rightarrow B \rightarrow C$). (See, e.g., Reference 52).

BNs have an interesting relation to canonical Boolean logical operators $\wedge$, $\vee$ and $\oplus$ formulas over variables. These formulas, which can be "deterministic" in principle, in BNs, can be naturally softened into probabilistic relations to facilitate some degree of uncertainty or noise. This probabilistic approach to modeling logic can facilitate representation of qualitative relationships among variables in a way that can be inherently robust to small perturbations by noise. For instance, the phrase "in order to hear music when listening to an mp3, it can be necessary and sufficient that the power be on and the headphones be plugged in" can be represented by a probabilistic conjunctive formulation that relates power, headphones and music, in which the probability that music can be audible depends only on whether power and headphones can be present. On the other hand, there can be a small probability that the music will still not play (e.g., perhaps no songs were loaded on to the device) even if both power and headphones are on, and there can be small probability that music can be heard even without power or headphone.

Note that the subset of networks that have discrete random variables that may be visible can only be considered. Networks with latent and continuous variables present their own challenges, although they share most of the mathematical foundations discussed here.

Exemplary Approaches to Learn the Structure of a BN

Classically, there have been two families of methods aimed at learning the structure of a BN from data. The methods belonging to the first family seek to explicitly capture all the conditional independence relations encoded in the edges, and are referred to as constraint based approaches. The second family, that of score based approaches, seeks to choose a model that maximizes the likelihood of the data given the model. Since both the exemplary approaches can lead to intractability (e.g., NP-hardness) (see, e.g., References 53 and 54), computing and verifying an optimal solution can be impractical and, therefore, heuristic procedures have to be used, which only sometimes guarantee optimality. A third class of learning procedures that takes advantage of specialized logical relations have been introduced below. Below is a description of other exemplary approaches. After the exemplary approach is introduced, it can be compared with that of all the techniques described.

Exemplary Constraint Based Approaches

An intuitive explanation of several common procedures used for structure discovery can be presented by explicitly considering conditional independence relations between variables.

The basic idea behind all procedures can be to build a graph structure reflecting the independence relations in the observed data, thus matching as closely as possible the empirical distribution. The difficulty in this exemplary approach can be in the number of conditional pairwise independence tests that a procedure would have to perform to test all possible relations. This can be exponential, which can be conditioned on a power set when testing for the conditional independence between two variables. This inherent intractability benefits from the introduction of approximations.

In this exemplary case, two (or more or less) exemplary constraint based procedures, the PC procedure (see, e.g., Reference 55) and the Incremental Association Markov Blanket ("IAMB") can be focused on, (see, e.g., Reference 56), because of their proven efficiency and widespread usage. In particular, the PC procedure can solve the aforementioned approximation problem by conditioning on incrementally larger sets of variables, such that most sets of variables will never have to be tested. Whereas the IAMB first computes the Markov blanket of all the variables and conditions only on members of the blankets.

The PC procedure (see, e.g., Reference 55) begins with a fully connected graph and, on the basis of pairwise independence tests, iteratively removes all the extraneous edges. It can be based on the idea that if a separating set exists that makes two variables independent, the edge between them can be removed. To avoid an exhaustive search of separating sets, these can be ordered to find the correct ones early in the search. Once a separating set can be found, the search for that pair can end. The exemplary PC procedure can order separating sets of increasing size 1 starting from 0, the empty set, and incrementing until 1=n−2. The exemplary procedure stops when every variable has fewer than 1−1 neighbors, since it can be proven that all valid sets must have already been chosen. During the computation, the larger the value of 1 can be, the larger number of separating sets must be considered. However, by the time 1 gets too large, the number of nodes with degree 1 or higher must have dwindled considerably. Thus, in practice, only a small subset of all the possible separating sets can need to be considered.

A distinct type of constraint based learning procedures uses the Markov blankets to restrict the subset of variables to test for independence. Thus, when this knowledge can be available in advance, a conditioning on all possible variables does not have to be tested. A widely used, and efficient, procedure for Markov blanket discovery can be IAMB. In it, for each variable X, a hypothesis set H(X) can be tracked. The goal can be for H(X) to equal the Markov blanket of X, B(X), at the end of the exemplary procedure. IAMB can consist of a forward and a backward phase. During the forward phase, it can add all possible variables into H(X) that could be in B(X). In the backward phase, it can eliminate all the false positive variables from the hypotheses set, leaving the true B(X). The forward phase can begin with an empty H(X) for each X. Iteratively, variables with a strong association with X (e.g., conditioned on all the variables in H(X)) can be added to the hypotheses set. This association can be measured by a variety of non-negative functions, such as mutual information. As H(X) grows large enough to include B(X), the other variables in the network will have very little association with X, conditioned on H(X). At this point, the forward phase can be complete. The backward phase can start with H(X) that contains B(X) and false positives, which can have little conditional association, while true positives can associate strongly. Using this exemplary test, the backward phase can remove the false positives iteratively until all but the true positives can be eliminated.

Exemplary Score Based Approaches

This exemplary approach to structural learning seeks to maximize the likelihood of a set of observed data. Since it can be assumed that the data can be independent and identically distributed, the likelihood of the data $\mathcal{L}(\cdot)$ can be simply the product of the probability of each observation. That can be, for example:

$$\mathcal{L}(D) = \prod_{d \in D} P(d)$$

for a set of observations D. Since it can be beneficial to infer a model $\mathcal{G}$ that best explains the observed data, the likelihood of observing the data given a specific model $\mathcal{G}$ can be defined as, for example:

$$\mathcal{LL}(\mathcal{G}, \mathcal{D}) = \prod_{d \in D} P(d \mid \mathcal{G})$$

The actual likelihood may not be used in practice, as is quantity can become very small, and impossible to represent in a computer. Instead, the logarithm of the likelihood can be used for three reasons. First, the log(·) function can be monotonic. Second, the values that the log-likelihood takes do not cause the same numerical problems that likelihood does. Third, it can be easy to compute because the log of a product can be the sum of the logs (e.g., log(xy)=log x+log y), and the likelihood for a Bayesian network can be a product of simple terms.

For example, there can be a problem in learning the network structure by maximizing log-likelihood alone. In particular, for any arbitrary set of data, the most likely graph can always be the fully connected one (e.g., all edges can be present), since adding an edge can only increase the likelihood of the data. To correct for this phenomenon, log-likelihood can be supplemented with a regularization term that can penalize the complexity of the exemplary model. There can be a plethora of regularization terms, some based on information theory and others on Bayesian statistics (see, e.g. Reference 57), which can serve to promote sparsity in the learned graph structure, though different regularization terms can be better suited for particular applications.

Additionally, in this exemplary case, a particularly relevant and known score, the Bayesian Information Criterion ("BIC"), (see, e.g., Reference 50) can be described, which will be subsequently compared to the performance of the exemplary approach.

BIC uses a score that can consist of a log-likelihood term and a regularization term depending on a model $\mathcal{G}$ and data $\mathcal{D}$, where, for example:

$$BIC(\mathcal{G}, \mathcal{D}) = \mathcal{LL}(\mathcal{G}, \mathcal{D}) - \frac{\log m}{2} dim(\mathcal{G}) \qquad (13)$$

Here, D can denote the data, m can denote the number of samples and dim($\mathcal{G}$) can denote the number of parameters in the model. Because dim(·) can depend on the number of parents each node has, it can be a good metric for model complexity. Moreover, each edge added to tj can increase model complexity. Thus, the regularization term based on dim(·) can favor graphs with fewer edges and, more specifically, fewer parents for each node. The term log m/2 essentially weighs the regularization term. The effect can be that the higher the weight, the more sparsity will be favored over "explaining" the data through maximum likelihood.

The likelihood can be implicitly weighted by the number of data points, since each point can contribute to the score. As the sample size can increase, both the weight of the regularization term and the "weight" of the likelihood can increase. However, the weight of the likelihood can increase faster than that of the regularization term. Thus, with more data, likelihood can contribute more to the score, and the observations can be trusted more, and can have less of a need for regularization. Statistically speaking, BIC can be a consistent score. (See, e.g., Reference 50). In terms of structure learning, this observation can imply that for sufficiently large sample sizes, the network with the maximum BIC score can be I-equivalent to the true structure. Consequently, $\mathcal{G}$ can contain the same independence relations as those implied by the true exemplary structure. As the independence relations can be encoded in the edges of the graph, a Markov-equivalent network can be learned, with the same skeleton and the same v-structures as the true graph, though not necessarily with the correct orientations for each edge.

Exemplary Learning Logically Constrained Networks

As discussed herein, it was noted that an important class of BNs can capture common binary logical operators, such as $\wedge$, $\vee$, and $\oplus$. Although the learning procedures mentioned above can be used to infer the structure of such networks, some exemplary procedures can employ knowledge of these logical constraints in the learning process.

A widely used approach to learn a monotonic cancer progression network with a directed acyclic graph ("DAG") structure and conjunctive events can be Conjunctive Bayesian Networks (see CBNs, (see, e.g., Reference 58)). This exemplary model can be a standard BN over Bernoulli random variables with the constraint that the probability of a node X taking the value 1 can be zero if at least one of its parents has value 0. This can define a conjunctive relationship, in that all the parents of X must be 1 for X to possibly be 1. Thus, this model alone cannot represent noise, which can be an essential part of any real data. In response to this shortcoming, hidden CBNs, (see, e.g., Reference 59), were developed by augmenting the set of variables: to each CBN variable X, which can capture the "true" state, and can be assigned a correspondence to a new variable Y that can represent the observed state. Thus, each new variable Y can take the value of the corresponding variable X with a high probability, and the opposite value with a low probability. In this exemplary model, the variables X can be latent. For example, they may not be present in the observed data, and have to be inferred from the observed values for the new variables. Learning can be performed via a maximum likelihood approach, and can be separated into multiple iterations of two steps. First, the parameters for the current hypothesized structure can be estimated using the Expectation-Maximization procedure (see, e.g., Reference 60), and the likelihood given those parameters can be computed. Second, the structure can be perturbed using some hill climbing heuristic. A Simulated Annealing procedure (see, e.g., Reference 61) can be used for this step. These two steps can be repeated until the score converges. However, the Expectation-Maximization procedure only guarantees convergence to a likelihood local maximum and, thus, the overall exemplary procedure may not be guaranteed to converge to the optimal structure.

Since CBNs can represent the current benchmark for the reconstruction of cancer progression models from cross-sectional genomic data, their comparison with the exemplary approach can be informative.

Exemplary a Framework for Prima Facie Causation

For the sake of clarity, the exemplary procedures can include successive steps of successively increasing complexity of the causal formulas; for example, going from single-cause (e.g., "atomic") formulas, to conjunctive formulas consisting of atomic events to formulas in Conjunctive Normal Forms ("CNF") (e.g., [('burning cigarette'$\wedge$'dried wood')$\vee$('lightning'$\wedge$'no rain')$\triangleright$ 'forest fire']). The causal formulas can be represented as a directed graph: G=(V, E), where the nodes can be the atomic events, and edges can be between an event that appears positively as a literal in the formula describing the cause and an event that can be its effect: $\forall_{c,e \in V}\langle c,e\rangle \in E$, if c can be a literal in $\varphi$ and $\varphi \triangleright e$.

Throughout the Specification "real world" can refer to the concrete instance where data can be gathered (e.g., as opposed to the counterfactual terminology of "possible worlds") and by "topology", a combination of structural and quantitative probabilistic parameters.

Exemplary Single-Cause Prima Facie Topologies

When at most a single incoming edge can be assigned to each event (e.g., an event has at most one unique cause in the real world: $\forall_{e \in V} \exists!_{e \in V} c \triangleright e$), this can be called a causal structure single-cause prima facie topology, a special and important case of the most general prima facie topology causal structures. Note that the general model can be represented as a DAG where each edge can be a prima facie cause between a parent and its child. In the special case of the single-cause prima facie topology, the causal graphs can be trees or, more generally, forests when there can be disconnected components. Thus, each progression tree subsumes a distribution of observing a subset of the mutations in a cancer sample (see, e.g., Reference 62).

Figure 10A:
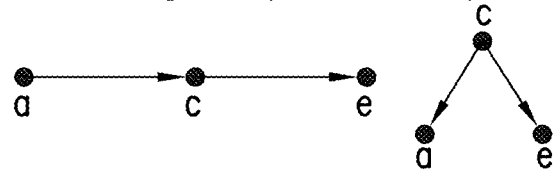
FIGS. 10A and 10B are diagrams of examples of screening-off and background context according to an exemplary embodiment of the present disclosure.
Figure 10B:
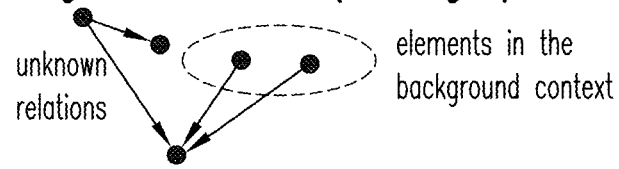

The following propositions (e.g., shown in exemplary graphs of FIGS. 10A and 10B) were shown to hold for single-cause prima facie topologies, and used to derive an procedure to infer tree (e.g., forests) models of cancer progression based upon the Suppes definition. (See, e.g., Reference 62). Examples of screening-off and of background context are shown in an exemplary diagram of FIG. 10A, which illustrate an example of Reichenbach's screening-off where c can be a genuine cause of e and a can be a genuine cause of c, and the correlations between a and e may only just manifestations of these known causal connections, and c can be a common cause of both a and e. FIG. 10B illustrates an exemplary diagram of Cartwright's background context.

Figure 11:
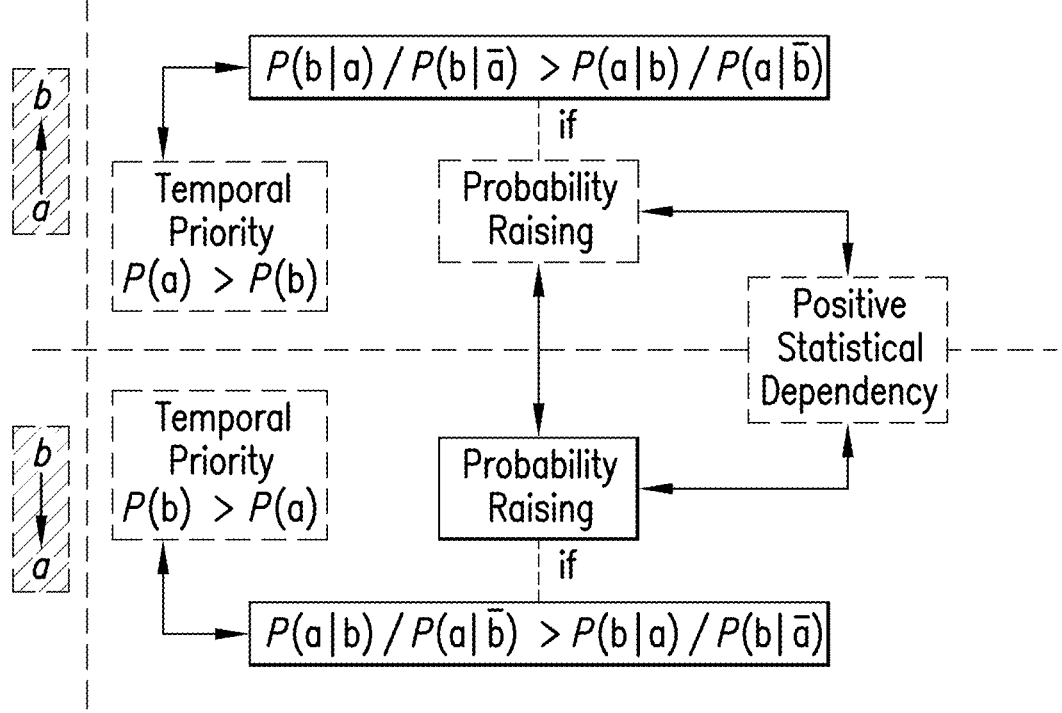
FIG. 11 is a diagram of exemplary properties and/or procedures according to an exemplary embodiment of the present disclosure.

FIG. 11 illustrates a diagram of exemplary (e.g., prima facie) properties. For example, properties of Suppes definition of probabilistic causation where c can be a prima facie cause of e if the cause can be a probability raiser of e, and it can occur more frequently.

Statistical dependence. Whenever the PR holds between two events c and e, then the events can be statistically dependent in a positive sense, for example:

$$P(e|c) > P(e|\bar{c}) \Leftrightarrow P(e \wedge c) > P(e)P(c). \tag{14}$$

Mutuality. If c can be a probability raiser for e, then so can be the converse, for example: $P(e|c) > P(e|\bar{c}) \Leftrightarrow P(c \wedge e) > P(c|\bar{e})$ Natural ordering. For any two events c and e such that c can be a probability raiser for e, a "natural" ordering arises to disentangle a causality relation can be, for example:

$$P(c) > P(e) \Leftrightarrow \frac{P(e|c)}{P(e|\bar{c})} > \frac{P(c|e)}{P(c|\bar{e})}. \quad (15)$$

Putting together all these exemplary properties, it can be natural to derive the following equivalent characterization of Suppes Definition: c can be said to be a prima facie cause of e if c can be a probability raiser of e, and it occurs more frequently Thus, for example:

$$c \triangleright e \Leftrightarrow P(e|c) > P(e|\bar{c}) \wedge P(c) > P(e). \quad (16)$$

The assertion above restates that single-causes, involving only persistent events, can lead to a model of real world time (e.g., $t_c$ and $t_e$, in Suppes Definition), which can be consistently imputed to the observed frequencies of events.

Consequent to this definition, it can be observed that it can be necessary, but not sufficient to identify the causal real world processes (e.g., path or branch) and, thus, to solve causality per se. In fact, as it can be seen in the FIGS. 12A and 12B, arrows 1205 (e.g., consistently in the real world and in the topology) make this definition necessary, while arrows 1210 (e.g., spurious, resulting from transitivities, because of the single-cause hypothesis) render the condition insufficient. Arrows 1210 can be present to indicate potential genuine causes corresponding to real causes (e.g., which can be the case when observations can be statistically significant for the real world). Thus, a correct inferential procedure will have to select real causes among the potential genuine ones, a subset of prima facie causes.

As discussed above, spurious causes can manifest through spurious correlation or chance. In the infinite sample size limit the "law of large numbers" can eliminate the effect of chance. In other words, with large enough sample, chance by itself will not suffice to satisfy Suppes Definition. The former situation for spuriousness can depend on the real world topology, and can appear under observation like a prima-facie/genuine cause in disguise, even with an infinite sample size (e.g., edges 1215), for which the "temporal direction" has no causal interpretation, as it depends on the data and topology). For these reasons, a single-cause prima facie topology asymptotically will not contain false negatives (e.g., all real world causes can be in the topology as Suppes Definition can be necessary) but it might contain, depending on the real world topology, false positives (e.g., arrows 1210 and edges 1215, as Suppes Definition may not be sufficient).

Exemplary Conjunctive-Cause Prima Facie Inference

A propositional formula composed of conjunctions of a set of literals can be denoted by, for example: $c = c_1 \wedge \ldots \wedge c_n$, which can imply that n events $c_1, \ldots, c_n$, have occurred (e.g., in some unspecified order) so as to collectively cause some effect e (e.g., shown as in FIG. 13), and it can be assumed that each $c_i (1 \leq i \leq n)$ can be an atomic event.

Suppes' notion of probabilistic causation (e.g., Suppes Definition) can be naturally extended to con-junctive clauses as in the following definition:

Definition 5 (Conjunctive Probabilistic Causation)

For any conjunctive event $c = c_1 \wedge \ldots \wedge c_n$ and e, occurring respectively at times $\{t_{c_i} | i = 1, \ldots n\}$ and $t_e$, under the mild assumptions that $0 < P(c_i), P(e) < 1$, for any i, the conjunctive event c can be a prima facie conjunctive cause of $e(c \triangleright e)$ if all of its components $c_i$ occur before the effect and their occurrences collectively raises the probability of the effect as, for example:

$$\max\{t_{c_1}, \ldots t_{c_n}\} < t_e \text{ and } P(e|c) > P(e|\bar{c}) \quad (17)$$

where $P(e|c) = P(e|c_1 \wedge \ldots \wedge c_n)$ and $P(e|\bar{c}) = P(e|\bar{c_1} \wedge \ldots \wedge \bar{c_n}) = P(e|\bar{c_1} \wedge \ldots \wedge \bar{c_n})$.

This extension follows the semantics of conjunctive connectives, which states that all causes must occur before the effect, thus justifying the choice of picking the latest event, in time, prior to e to generalize Suppes Definition: namely, the max$\{\cdot\}$ operation applied to the causal events. This definition retains the semantics of single-cause prima facie unchanged, as it can be a special case with c=c and max$\{t_{c_i}\} = t_c$. Unfortunately, as before, it still has the same weakness that it can be necessary, but not sufficient, to identify conjunctive-causal relations, and hence lacks the power to define causality per se.

The properties of single-causes prima facie topologies extend appropriately to conjunctive topologies.

Exemplary Proposition 1

The properties of statistical dependence, mutuality and natural ordering for single-causes can still be valid for conjunctive clauses.

Figure 13:
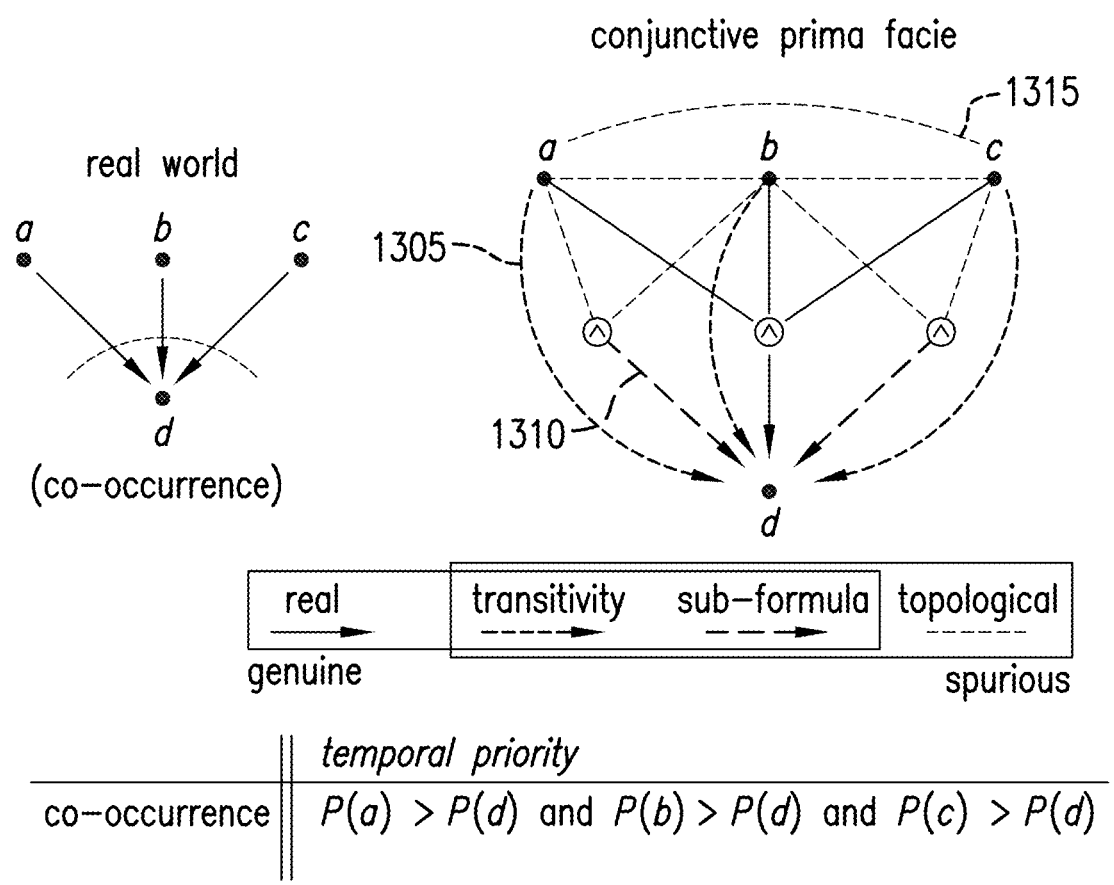
FIG. 13 is a diagram of exemplary conjunctive-cause topology according to an exemplary embodiment of the present disclosure.

In this exemplary case, some caution can be exercised in distinguishing between prima facie single or conjunctive causes. As shown in FIG. 13, in fact, for a simple conjunctive clause in the real world (e.g., a and b and c) the following conjunctive clauses $$a \wedge b \triangleright d \; a \wedge c \triangleright d \; b \wedge c \triangleright d$$

as well as the single causes $a \triangleright d$, $b \triangleright d$ and $c \triangleright d$, can be prima facie. The single causes can be spurious or transitive, as in FIG. 12. However, spurious sub-formulas can be called the conjunctive clauses that can be syntactically strictly sub-formulas of $a \wedge b \wedge c \triangleright d$, for example, the only formula it can be beneficial to infer. As in branch processes, topology-dependent spurious causes may appear because of spurious correlations. These causal relations can include general spurious formulas constituting of a sub-formula and any of its parents. Similarly, spurious causes due to chance can vanish asymptotically as sample size grows to infinity. In summary, it can be noted that a conjunctive topology, similarly to the single-cause framework, will not contain false negatives (e.g., all real world causes in the topology) but it might contain, depending on the real world topology, false positives (e.g., edges 1305, 1310 and 1315 of FIG. 13).

It can be noted that the total number of potential formulas and transitivities can be exponential in the size of $|G|=n$, which can be, for example:

$$\sum_{i=1}^{n-1} \binom{n-1}{i} = 2^{n-1} - 1.$$

Figure 12A:
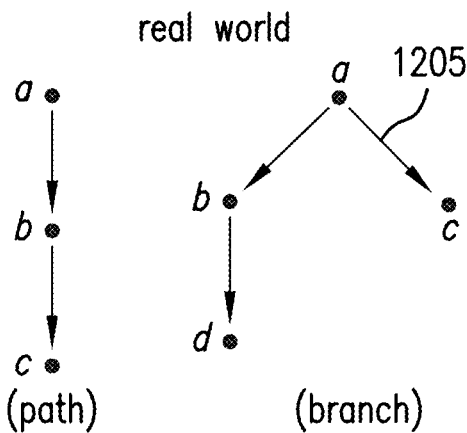
FIGS. 12A and 12B are diagrams of exemplary single-cause topology according to an exemplary embodiment of the present disclosure.
Figure 12B:
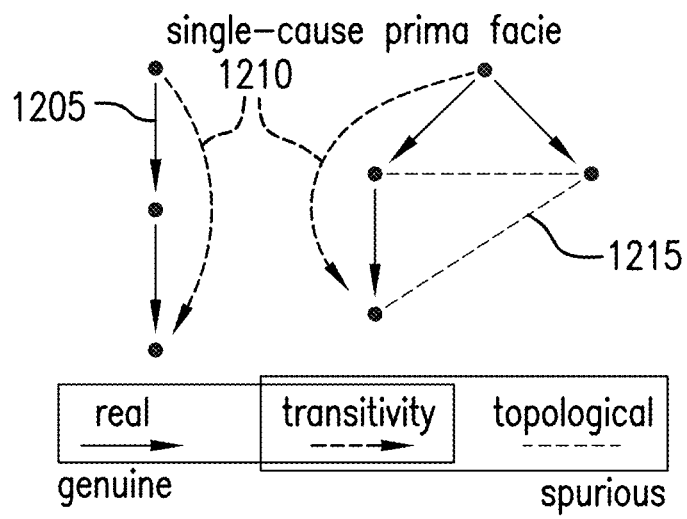

This can be a lower bound accounting only for the level of the connective, and can be expected to grow further when more complex real world processes can be considered. Finally, as shown in FIGS. 12A and 12B, the number of spurious causes due to topology (e.g., edges 1215), can be quadratic in the formula size, being, for example $$2\binom{n-1}{2} = (n-1)(n-2).$$

This complexity hints at the fact that an exhaustive search of all the possible conjunctive formula may not be feasible, in general.

In order to generalization to formulas in conjunctive normal form Next, consider a formula in conjunctive normal form ("CNF"), where, for example:

$$\varphi = c_1 \wedge \ldots \wedge c_n,$$

where each $c_1$ can be a disjunctive clause $c_1 = c_{i,1} \vee \ldots \vee c_{i,k}$ over a set of literals, each literal representing an event (e.g., a Boolean variable) or its negation. By following the same exemplary approach as used earlier to extend Suppes' Definition from single to conjunctive clauses, $\varphi \triangleright e$.

Exemplary Definition 6 (e.g., CNF Probabilistic Causation)

For any CNF formula $\varphi$ and e, occurring respectively at times $t_\varphi$, and $t_e$, under the mild assumptions that $0 < P(\varphi)$, $P(e) < 1$, $\varphi$ can be a prima facie cause of e if, for example:

$$t_\varphi < t_e \text{ and } P(e|\varphi) > P(e|\overline{\varphi}). \tag{18}$$

As described above, this definition subsumes Definition 5, and can be necessary, but not sufficient, to identify causal relations, hence lacking the power to solve causality per se.

In this exemplary case, the number of prima facie (e.g., including both genuine and spurious) causes can grow combinatorially much more rapidly than the simplest case of a unique conjunctive clause. This situation can be rather alarming, since even the simplest case already produces an exponentially large set of prima facie causes in terms of the number of events. In this case, in fact, further causal relations can emerge as a result of mixing events from all the clauses of $\varphi$. CNF formulas follow analogous properties as single and conjunctive topologies, as shown below.

The properties of statistical dependence, mutuality and natural ordering for single and conjunctive prima facie topologies can extend to CNF formulas mutatis mutandis. For illustrative purposes, consider the formula $(a \wedge b) \vee c \triangleright d$, which can be in disjunctive normal form ("DNF"). If, for example, the claim $a \triangleright d$ can be evaluated, the background context would be the atomic event c, being b-dependent when a causes d. A symmetric situation holds, to evaluate $b \triangleright d$. In light of this discussion, note that if the formula to can be converted to its CNF analogue $(a \vee c) \wedge (b \vee d) \triangleright d$, the roles of sub-formulas $a \vee c$ and $b \vee c$ can be interpreted in identifying a background context, c. It follows that, for any CNF formula, the atomic events of all the disjunctive clauses in the equivalent DNF formula provide all the possible background contexts a-la-Cartwright.

The exemplary system, method, and computer-accessible medium, according to an exemplary embodiment of the present disclosure, can include timing in the real world. Consider the CNF formula above, and denote it as cp, and recall that Definition 6 utilizes $t_\varphi < t_d$. One might wonder whether a trivial time-ordering relation exists, whose complexity can be linear with respect to all the operators in $\varphi$. Were it so, $\varphi$ can be parsed into its constituents, and recursively express the temporal relations as a direct function of those relations that hold for its sub-formulas. Unfortunately, this appears not to be the case, except when the underlying syntax can be restricted to certain specific operators (e.g., conjunctions). Thus appropriate care must be taken in implementing a model of real world time. Thus, an exemplary procedure, working on the illustrative example of the previous paragraph, cannot conclude any ordering about $t_{a \vee c}$, $t_{b \vee c}$ and $t_d$, solely by looking at the observed probabilities of their atomic events—instead it must gather the correct information for certain sub-formulas at the level of their connective (e.g., the V in this case). A general rule that avoids these difficulties, and devises a correct and efficient timing-inference procedures, can be stated as follows: it can be safe to model probabilistic causation in terms of whole formulas, while permitting compositional reasoning over sub-formulas, only when the syntax can be restricted to certain Boolean connectives.

Exemplary Inference Procedure

The exemplary structure of the reconstruction problem can be as follows. Assume that there is a set G of n mutations (e.g., events, in probabilistic terminology) and m samples, represented as a cross-sectional dataset, for example, without explicit timing information, in an m×n binary matrix $D \in \{0,1\}^{m \times n}$ in which an entry $D_{k,l} = 1$ if the mutation 1 was observed in sample k, and 0 otherwise. Note that dataset lacking explicit timing information can typically be, for instance, in cancer patient data.

To introduce the exemplary system, method, and computer-accessible medium additional notations can be utilized: $\mathcal{U}$ can denote the universe of all possible causal claims $\varphi \triangleright e$, where $\varphi$ can be a CNF formula over the events in D (e.g., $G \subseteq \mathcal{U}$) and e ca be an atomic event. With $\mathcal{C} \subset \mathcal{U}$, it all the causal claims whose formulas can be conjunctive over atomic events may not contain disjunctions. For a general CNF formula $\varphi$ it can be denoted by chunks ($\varphi$) its set of disjunctive clauses. For example, $a \wedge b \triangleright e \in \mathcal{C}$ while $(a \vee \overline{b}) \wedge (c \vee d) \wedge e \triangleright f \notin \mathcal{C}$ and chunks $((a \vee \overline{b}) \wedge (c \vee d) \wedge e) = \{(a \vee \overline{b}), (c \vee d), e\}$.

Inferred Structures.

The exemplary system, method, and computer-accessible medium, according to an exemplary embodiment of the present disclosure, can reconstruct a general DAG from the input data. It can share many structural and procedureic properties with the Conjunctive Bayesian Networks approach (see, e.g., Reference 58)—especially in the context of cancer progression models. However, the exemplary system, method, and computer-accessible medium, according to an exemplary embodiment of the present disclosure, can face no obstacle in spontaneously inferring from the input data various sub-structures of a DAG, for example, forests—or, more specifically, trees—although it has no "hard-coded" policies for doing so. Thus, the exemplary system, method, and computer-accessible medium, according to an exemplary embodiment of the present disclosure, can be expected to be applicable in a context-agnostic manner, and can compete well with other exemplary approaches, which may not be a priori restricted from having advantageous structural information, (See, e.g., References 62-65).

The exemplary DAGs can build on arbitrary CNF formulas, using the strategy that disjunctive clauses can be first summarized by unique DAG nodes. As an example, a formula $(a \vee b) \wedge c \wedge d$ will be modeled with three nodes: one for $(a \vee b)$, the aggregated disjunction, one for c and one for d. The reasons disjunctions may not be handled are discussed below.

In the following, a progression DAG can be denoted as $\mathcal{D} = (N, \pi)$ where $N \subseteq \mathcal{U}$ can be the set of nodes (e.g., mutations or formulas) and $\pi$: N→$\wp$ (N): can be a function associating to each node j its parents $\pi(j)$. This exemplary model can yield the following.

Exemplary Definition 4 (e.g., DAG Causal Claims)

A $\mathcal{D}=(N, \pi)$ models the causal claims N $$= \bigcup_{j \in N} \{(c_1 \wedge \ldots \wedge c_n) \triangleright j \mid \pi(j) = \{c_1, \ldots, c_n\}\},$$

where $c_1 \wedge \ldots \wedge c_n$ can be a CNF formula and any $c_j$ can either be a ground event or a disjunction of events.

Going back to the example above, in the exemplary DAG there can be $\pi(j)=\{(a \vee b), c, d\}$ whose underlying causal claim would be $(a \vee b) \wedge c \wedge d \triangleright j$.

Each DAG can be augmented with a labeling function $\propto$: N→[0,1] such that $\propto(i)$ can be the independent probability of observing mutation i in a sample, whenever all of its parent mutations can be observed (e.g., if any). Each DAG can induce a distribution of observing a subset of events in a set of samples (e.g., a probability of observing a certain mutational profile, as defined below. $\mathcal{D}$ Exemplary Definition 5 (e.g., DAG-Induced Distribution)

Let $\mathcal{D}$ be a DAG and $\propto$:N→[0,1] a labeling function, $\mathcal{D}$ generates a distribution where the probability of observing N*⊆N events can be, for example:

$$P(N^*) = \prod_{x \in N^*} \propto (x) \cdot \prod_{y \in N/N^*} [1 - \propto (y)] \quad (19)$$

whenever x∈N*, $\pi(x) \subset N^*$, and 0 otherwise.

Notice that this definition, as expected, can be equivalent to the previously-used definitions (see, e.g., Reference 58), and can retain a tree-induced distribution. (See, e.g., References 62, 63 and 65). Further, notice that a sample which contains an event but not all of its parents, can have a zero probability, thus subsuming the conjunctive interpretation of the exemplary DAGs. These types of samples, which can represent "irregularities" with respect to D, might be generated when adding false positives/negatives to the sampling strategy. Finally, because nodes can be disjunctive formulas can extend this exemplary DAG definition to express causal claims with generic CNF formulas.

Inference Confidence:

bootstrap and statistical testing. A statistical foundation to the exemplary inferences can be provided, which employ such classical techniques as bootstrap (see, e.g., References 66 and 67), and the Mann-Whitney U test. (See, e.g., Reference 68).

In data preprocessing bootstrap with rejection resampling can be used. This can be used to estimate a distribution of the marginal and joint probabilities, where for each event: (i) repetitions rows can be sampled from the input matrix D (e.g., bootstrapped dataset), (ii) the distributions can be estimated from the observed probabilities, and (iii) values which do not satisfy 0<P(i)<1 and P(i|j)<1 P(j|i)<1 can be rejected, which can be iterated restarting from (i). This can conclude when there are at least about 100 values.

Any inequality (e.g., checking temporal priority and probability raising) can be estimated as follows: the Mann-Whitney U test with p-values set to 0.05 can be performed. This can be a non-parametric test of the null hypothesis that two populations can be the same against an alternative hypothesis, and can be especially useful to understand whether a particular population, for example P(i), tends to assume larger values than the other, for example, P(j). By employing this exemplary test, which does not need to assume Gaussian distributions for the populations, confidence p-values for both temporal priority and probability raising can be computed.

Once a DAG model can be inferred with the exemplary system, method, and computer-accessible medium, both para-metric and non-parametric bootstrapping methods can be used to assign a confidence level to its respective claims, and ultimately, to the overall exemplary causal model. These tests can consist of using the reconstructed model (e.g., in the parametric case), or the probabilities observed in the dataset (e.g., in the non-parametric case) to generate new synthetic datasets, which can then be reused for reconstructing of the progressions (see, e.g., Reference 67). The confidence can be given by the number of times the DAG, or any of its claims can be reconstructed from the generated data.

Exemplary CAPRI: A Hybrid Procedure for General CNF Formulas

Building upon the framework presented above, the exemplary system, method, and computer-accessible medium, according to an exemplary embodiment of the present disclosure, can be used to infer cancer progression models from cross-sectional data. The exemplary procedure can be hybrid in the sense that it can combine a structure-based approach (e.g., as of Definition 6) with a likelihood-fit constraint and, according to its input, can infer causal claims with various logical expressivity. Its computational complexity, which can be highly dependent on the expressivity of the claims, as well as its correctness are discussed below.

CAncer PRogression Inference (e.g., CAPRI can utilize its input, a matrix D and, optionally, a set of k input causal claims $\Phi)=\{\varphi_1 \triangleright e_1, \ldots \varphi_k \triangleright e_k\}$, where each $\varphi_i$ can be a CNF formula and $\varphi_i \not\sqsubseteq e_i$. Here $\sqsubseteq$ can represent the usual syntactical ordering relation among atomic events and formulas, for example, $a \sqsubseteq (a \vee b) \wedge c \wedge d$, and can be simply utilized to disallow malformed input claims, which would vacuously be labeled as prima facie causality (e.g., as of Definition 6), but would have no real causal meaning. For example, in the example above, it makes no sense to say that "a causes $(a \vee b) \wedge c \wedge d$." The augmented input $\Phi$, which can contain claims of the most complex type CAPRI can infer, can be optional in the sense that, if $\Phi=0$, the exemplary system, method, and computer-accessible medium can be able to infer "all" conjunctive causal claims over atomic events (e.g., claims $a \wedge b \wedge c \triangleright e$ in $\mathcal{C}$), but not general CNF ones.

CAPRI can begin performing a lifting operation over D, and then build a DAG D. Lifting operation can evaluate each CNF formula $\varphi_i$ for all input causal claims in $\Phi$ and its result, a lifted D, can be an extended input matrix for the exemplary system, method, and computer accessible medium. As an example, consider a claim $\Phi=\{(a \vee \overline{b}) \wedge (c \vee d) \wedge e \triangleright f\}$, the result of lifting for an input matrix D over a, . . . , f can be $$D = \begin{bmatrix} a & b & c & d & e & f \\ \hline 1 & 1 & 1 & 1 & 0 & 1 \\ 0 & 0 & 0 & 0 & 1 & 0 \\ 1 & 0 & 1 & 0 & 0 & 0 \\ 1 & 1 & 0 & 1 & 1 & 1 \\ 1 & 0 & 1 & 1 & 0 & 0 \end{bmatrix},$$

$$D(\Phi) = \begin{bmatrix} a & b & c & d & e & f & \varphi \\ \hline 1 & 1 & 1 & 1 & 0 & 1 & 0 \\ 0 & 0 & 0 & 0 & 1 & 0 & 0 \\ 1 & 0 & 1 & 0 & 0 & 0 & 0 \\ 1 & 1 & 0 & 1 & 1 & 1 & 1 \\ 1 & 0 & 1 & 1 & 0 & 0 & 0 \end{bmatrix},$$

since $\varphi=(a\vee \overline{b})\wedge(c\vee d)\wedge e$ and, for example, $(1 \vee \overline{0})\wedge(1 \vee 0)\wedge 0 \equiv 0$. After the lifting, $\mathcal{D}$ can be built by individually including in its set of nodes all the disjunctive sub-formulas of such CNF formulas, plus G. In the preceding example, $\{(a\vee \overline{b}), (c\vee d), e\}$ can be nodes in $\mathcal{D}$ note that $e \in G$). Notice that $D(\Phi)=D$ and $N=G$ if $\Phi=\emptyset$.

Subsequently, the parent function (e.g., the edges in $\mathcal{D}$) can be built by pair-wise implementation of exemplary Definition 6, which has been shown to subsume also Suppes Definition and exemplary Definition 5. For the sake of simpler exposition, the coefficients $\Gamma_{i,j}$ and $\Lambda_{i,j}$ can be used to evaluate temporal priority and probability raising, respectively, which can be needed to be strictly positive by exemplary Definition 6. Two cases can be distinguished: (i) when a causal claim directly involving an atomic event can be evaluated, or (ii) a chunk of an input formula. When a claim "i causes j" can be evaluated, and i∈G, it can be beneficial that exemplary Definition 6 can be satisfied. If so i can be a prima facie cause of j and it can be added to $\pi(j)$. When the same is performed for an input formula $\varphi$, if it can be prima facie for an event j, which can add $\varphi$ via all its constituting chunks to $\pi(j)$. This can be needed because the DAG $\mathcal{D}$ can be built by chunking input formulas, while the lifting operation can be performed on whole formulas; in reference to the examples above, when $\varphi$ can be prima facie to f, $(a\vee \overline{b})$, $(c\vee d)$ and e to $\pi(f)$ can be added. Moreover, since claims with the rightmost part an atomic event can be of interest, $\pi(j)=\emptyset$ for any j∈G. In case of the preceding input, for instance, any incoming edge in $(a\vee \overline{b})$ and $(c\vee d)$ does not need to be considered, while edges incoming in e solely from an atomic event can be considered. As for labeling, note that no label can be assigned to this kind of nodes. Further, since this construction can be consistent with the exemplary approach and the conjunctive interpretation of $\mathcal{D}$, once the steps defined in Eqs. 20 and 21 have been performed, $\mathcal{D}$ can be a prima facie DAG.

As prima facie causality can provide only a necessary condition, filtering out all spurious causes that might have been included in D can be performed. The underlying intuition can be as follows. For any prima facie structure, spurious claims can be contribute to reduce the likelihood-fit relative to true claims, and thus a standard maximum-likelihood fit can be used to select and prune the prima facie DAG. Based on all the discussion made above, a regularization term can be necessary to avoid overfitting. For example, if simple log-likelihood were used, it can be expected that the best model can actually be the prima facie structure. For this reason, the regularization score discussed above can be adopted; namely Bayesian Information Criterion ("BIC"), which can implement Occam's razor by combining log-likelihood fit with a penalty criterion proportional to the log of the DAG size via Schwarz Information Criterion. (See, e.g., Reference 69).

With 4)=0 only conjunctive causal claims in C can be inferred by the exemplary procedure, since the set of nodes of $\mathcal{D}$ can be N=G. Analysis of complexity, correctness and expressivity of CAPRI can now be presented.

Exemplary Complexity, Correctness And Expressivity Of CAPRI

Exemplary Complexity. The previous sections have stressed the rapidity with which the set of causal claims (e.g., or formulas) grow for a given model. Thus making their inference highly intractable. However, this complexity can be intrinsic to the problem. Or put alternatively, it can be independent of the underlying theory of causation. Unlike the heuristic approaches commonly used by many others to infer general causal claims, the exemplary system, method, and computer-accessible medium, according to an exemplary embodiment of the present disclosure and incorporate a twofold approach. To infer simple claims (e.g., single or conjunctive causes, at most), the exemplary CAPRI's execution can be self-contained (e.g., no input besides D can be required) and polynomial in the size of D. Instead, the number of inferable general causal claims (e.g., CNF) can be limited, by requiring that they be specified as an input to the exemplary system, method, and computer-accessible medium, according to an exemplary embodiment of the present disclosure in 0. In this case the exemplary CAPRI tests, with a polynomial cost, those claims plus the simple ones, and its complexity spans over many orders of magnitude according to the structural complexity of the input set 0, as further elaborated in the following theorem.

Exemplary Theorem 3 (Asymptotic Complexity)

Let $|G|=n$ and $D \in \{0,1\}^{m \times n}$ where m≫n, and let N the nodes in the DAG returned by CAPRI, the worst case time and space complexity of building a prima facie topology can be, ignoring the cost of bootstrap, for example:

---

Algorithm 1 CAncer PRogression Inference (CAPRI)

1: Input: A set of events G = $\{g_1, g_n\}$, an m × n matrix $D \in \{0,1\}^{m \times n}$ and k CNF causal claims $\Phi = \{\varphi_1 \rhd e_1, \ldots, \varphi_k \rhd e_k\}$ where, for any i, $e_i \not\in \varphi_i$ and $e_i \in G$;

2: [Lifting] Define the lifting of D to D ($\Phi$) as the augmented matrix $$D(\Phi) = \begin{bmatrix} D_{1,1} & \cdots & D_{1,n} & \varphi_1(D_1,.) & \cdots & \varphi_k(D_1,.) \\ \vdots & \ddots & \vdots & \vdots & \ddots & \vdots \\ D_{m,1} & \cdots & D_{m,n} & \varphi_1(D_m,.) & \cdots & \varphi_k(D_m,.) \end{bmatrix}. \quad (9)$$

by adding a column for each $\varphi_i \rhd c_i \in \Phi$, with $\varphi_i$ evaluated row-by-row define the coefficients $$\Gamma_{i,j} = \mathcal{P}(i) - \mathcal{P}(j), \text{ and } \Lambda_{i,j} = \mathcal{P}(j|i) - \mathcal{P}(j|\bar{i}), \quad (10)$$

pair-wise over D ($\Phi$);

-continued

Algorithm 1 CAncer PRogression Inference (CAPRI)

3: [DAG structure] Define a DAG $\mathcal{D} = (N, \pi)$ where $$N = G \cup \left(\bigcup_{\varphi_1} \text{chunks}_{(\varphi_1)}\right), \pi(j \notin G) = \emptyset; \quad (11)$$

$$\pi(j \in G) = \{i \in G \mid \Gamma_{i,j} \wedge A_{i,j} > 0\} \cup$$

$$\{\text{chunks}(\varphi) \mid \Gamma_{\varphi,j} \wedge A_{\varphi,i} > 0, \varphi \triangleright j \in \Phi\}.$$

4: [DAG labeling] Define the labeling $\alpha$ as follows $$\alpha(j) = \begin{cases} \mathcal{P}(j), & \text{if } \pi(j) = \emptyset \text{ and } j \in G; \\ \mathcal{P}(j \mid i_1 \wedge \ldots \wedge i_n), & \text{if } \pi(j) = \{i_1, \ldots i_n\}. \end{cases}$$

5: [Likelihood fit] Filter out all spurious causes from $\mathcal{D}$ by likelihood fit with the regularization BIC score and set $\alpha(j) = 0$ for each removed connection.
6: Output: the DAG $\mathcal{D}$ and $\alpha$;

$\Theta(mn)$ time and $\Theta(n^2)$ space, if $\Phi = \emptyset$;

$\Theta(|\Phi|mn)$ time and $\Theta(|\Phi| m)$ space, if $\Phi \subset \mathcal{U}$ and $|N| \ll m$ (i.e., there are sufficiently many samples to characterize the input formulas);

$\mathcal{O}(2^{2^n})$ time and space, if $\Phi = \mathcal{U}$.

As shown above, the procedureic complexity can span over many orders of magnitude according to the structural complexity of the input set 1) which can determine the number of nodes in the returned DAG, for example, |N|. Hence, aside from the cost of likelihood fit, the cost of the procedure can be polynomial only if $\Phi$ can be polynomial in the number of input samples and atomic events. This observation forewarns one of the hazard of a brute force approach, which attempts to test all possible causal claims. Generally speaking, despite the price of possibly "missing" some real causal claims, one should be able to identify most relevant causal structures by exploiting domain-knowledge, biological priors, and empirical/statistical estimations in selecting reasonable input $\Phi$ (e.g., focusing on certain key driver-mutations over the others). Note that this problem's inherent computational intractability does not negate the power of the procedureic automation, relative to what can be achievable with manual analysis.

Exemplary Correctness and Expressivity.

Let $\mathcal{W} \subseteq \mathcal{U}$ be the set of true causal claims in the real world, which can be inferred (e.g., in the tests of the exemplary procedure on synthetic data, W can be known, once a DAG to generate its input data can be fixed). Here, the relation between $\mathcal{W}$ and the set of causal claims retrieved by the exemplary procedure can be investigated as a function of sample size m and the presence of false positives/negatives which can be assumed to occur at rates $\in_+$ and $\in_-$.

Below $\Sigma$ denotes the set of causal relations, implicit in the DAG $\mathcal{D}$ returned by the exemplary procedure for an input set $\Phi$ and a matrix D; this can be written as $D(\Phi) \parallel -\Sigma$. Such claims can be evaluated as in exemplary Definition 7. The following can be proved.

Exemplary Theorem 4 (Soundness and Completeness)

When the sample size $m \to \infty$ and the data can be uniformly affected by false positives and negatives rates $\in_- = \in_+ \in [0,1)$, if the input given can be a superset of the true causal claims, then the exemplary CAPRI can reconstruct exactly the true causal formulas $\mathcal{W}$, that can be, if $\mathcal{W} \subset \Phi$ then $D(\Phi) \parallel - \mathcal{W} \cap \Phi$.

Notice that if it could be assumed that $\Phi$ characterizes $\mathcal{W}$ well, then all real causal claims can be in $\Phi$, and the corollaries below follow immediately.

Exemplary Corollary 1 (Exhaustivity)

Under the hypothesis of the above theorem $D(\mathcal{U}) \parallel - \mathcal{W}$.

Exemplary Corollary 2 (Least Fixed Point)

$\mathcal{W}$ can be the lfp of the monotonic transformation as, for example:

$$\underset{\Phi}{\sqcup} D(\Phi) \equiv D\left(\underset{\Phi}{\sqcup} \Phi\right) \parallel \vdash \mathcal{W}$$

Since a direct application of this exemplary theorem can incur a prohibitive computational cost, it only serves to idealize the ultimate power of the exemplary system, method, and computer-accessible medium. That can be, the theorem only states that the exemplary CAPRI can be able to select only the true causal claims asymptotically, as the size of $\mathcal{U}$ grows, albeit exponentially. It can also clarify that the exemplary system, method, and computer-accessible medium, according to an exemplary embodiment of the present disclosure can "filter out" all the spurious causal claims (e.g., true negatives), and produce the true positives from the set of the genuine causal claims more and more reliably as a function of the computational and data resources.

Now the exemplary attention can be restricted to conjunctive clauses in C—for example, those formulas which can be defined only on atomic events—so as to enable a fair comparison. (See, e.g., Reference 58).

Exemplary Theorem 5 (Inference of Conjunctive Clauses)

Let $\Phi = \emptyset$; as before, when the sample size $m \to \infty$ and the data can be uniformly affected by false positives and negatives rates $e_- = e_+ \in [0,1)$, then only conjunctive clauses on atomic events can be inferred, which can either be true or spurious for general CNF formulas. That can be: if $D(\emptyset) |||-\Sigma$ then $\Sigma \subseteq \mathcal{W}$. Furthermore, 1. $\Sigma \cap \mathcal{W}$ can be true claims and
2. for any other claim of $\alpha \triangleright e \in (\Sigma/\Sigma \cap \mathcal{W})$ there exist $\beta \triangleright e \in \mathcal{W} \setminus \mathcal{W}$ such that $\beta$ screens off $\alpha$ from e.

This exemplary theorem states that even if one can be neither willing to pay the cost of augmenting the input set of formulas nor can a suitable formula be found to augment, the exemplary system, method, and computer-accessible medium can still be capable of inferring conjunctive clauses, whose members can be either genuine or a conjunctive sub-formula of a more complex genuine CNF formula $\beta$ (e.g., regardless of whether a cause of the second kind can be considered to be spurious).

An immediate corollary of these two exemplary theorems can be that the exemplary system, method, and computer-accessible medium works correctly, when it can be fed with all possible conjunctive formulas.

Exemplary Corollary 3

Under the hypothesis of the above theorems, $D(\emptyset) |||-\Sigma \Leftrightarrow D(\mathcal{C})|||-\Sigma$.

In practice, though still exponential, the exemplary system, method, and computer-accessible medium, according to an exemplary embodiment of the present disclosure, can be less computationally intensive, when using $\mathcal{W}$ than with $\mathcal{U}$, as it can trade off computational complexity against expressivity of the inferred causal claims.

In the context of automatic inference of logical formulas expressivity of the inferred claims relates to compositional inference. In particular, it can be easy to see that for a disjunctive formula $c_1 \vee \ldots \vee c_n$, the following holds where, for example:

$$c_1 \vee \ldots \vee c_n \triangleright e \not\Rightarrow \forall_{c_i} c_i \triangleright e,$$

which can be the reason why full CNF formulas cannot compositionally inferred by reasoning over their constituents (e.g., any $c_i$, might not satisfy the prima facie definition on its own). Thus, the hypothesis set $\Phi$ can be relied upon, unless one could assume to know a priori the formulas and hence the background contexts (e.g., any other c, for j≠i), which poses a circularity issue. An instance of this constraint can be of particular importance with respect to cancer. For example, in modeling synthetic lethality (see FIG. 14) which can be expressed as $c_1 \oplus c_2 \triangleright e$ where $c_1 \oplus c_2 = (c_1 \wedge \bar{c}_2) \vee (\bar{c}_1 \wedge c_2)$.

Figure 14:
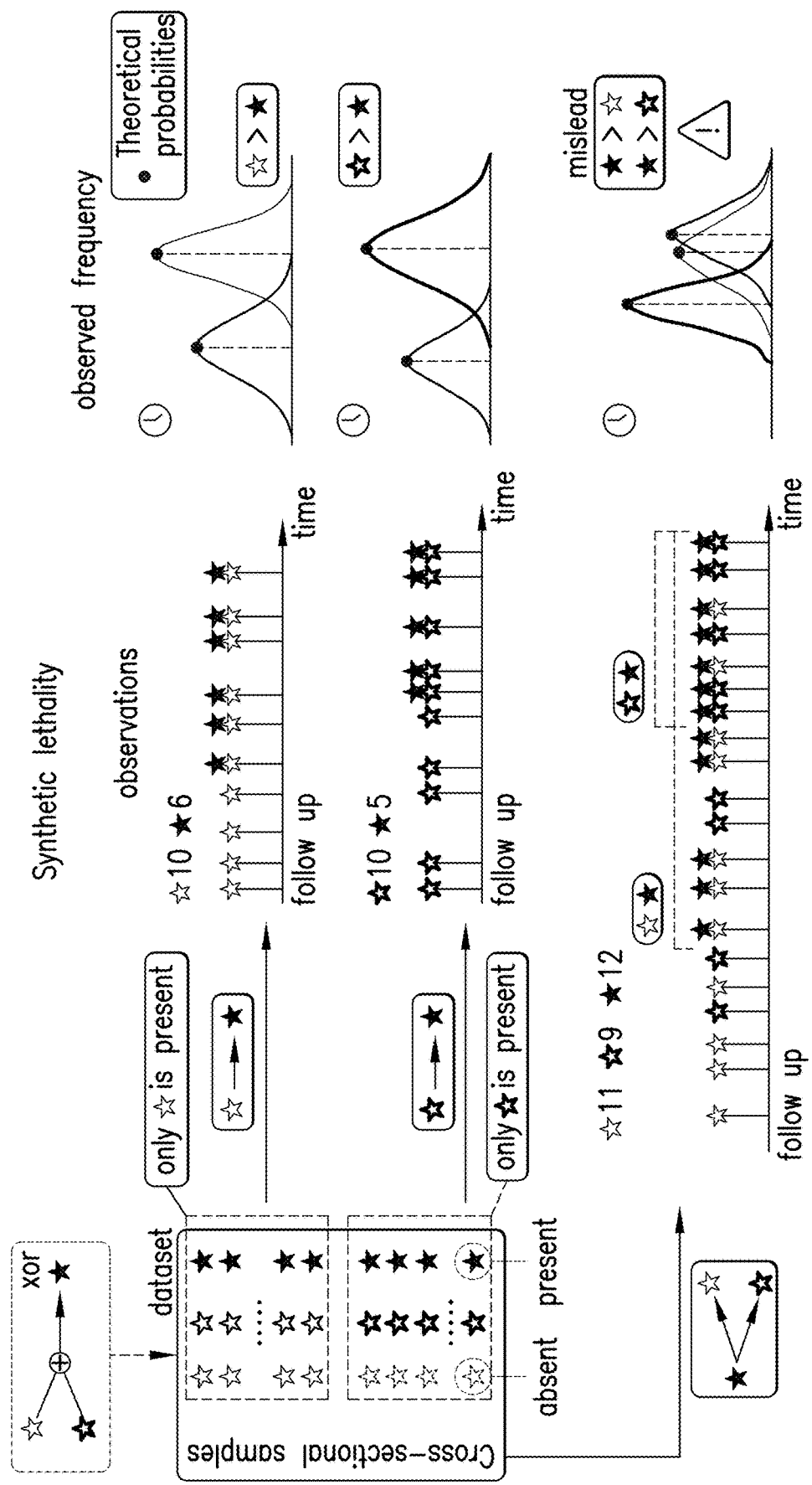
FIG. 14 is a diagram of caveats in inferring synthetic lethality relations according to an exemplary embodiment of the present disclosure.

In particular, FIG. 14 illustrates exemplary diagrams providing caveats in inferring synthetic lethality relations. For a synthetic lethality causal relation among a and b towards c, if one considers a dataset of aggregated samples, the risk of misleading the temporal priority relation among a, b and c can be high. If one were to know, a priori, that aⓇb is part of the claim, one could separate data and work safely. Unfortunately, being unknown a priori, only domain knowledge, biological priors or hypothesis testing can be relied upon.

The exemplary system, method, and computer-accessible medium, according to an exemplary embodiment of the present disclosure, can be applied to infer tree or forest models of progression, and can be evaluated empirically against other approaches in the literature which can be specifically tailored for tree/forests. (See, e.g., References 62, 63 and 65). All these exemplary approaches can have the same quadratic complexity (e.g., in the number of events in |G| and, just as with the exemplary CAPRI, can be shown to converge asymptotically to the correct tree, even in the presence of noisy observations. Despite asymptotic equivalence, the exemplary procedures can differ in performance under various settings of finite data (e.g., usually, synthetic), as previously described. The simpler procedure, CAncer PRogression Extraction with Single Edges (e.g., CAPRESE, (see, e.g., Reference 62), can differ from CAPRI, as it relies on a score based on probability raising with a shrinkage estimator, which can intuitively correct for the sample size and noise. (See, e.g., References 66 and 67).

Exemplary Results: Synthetic Data

Figure 15:
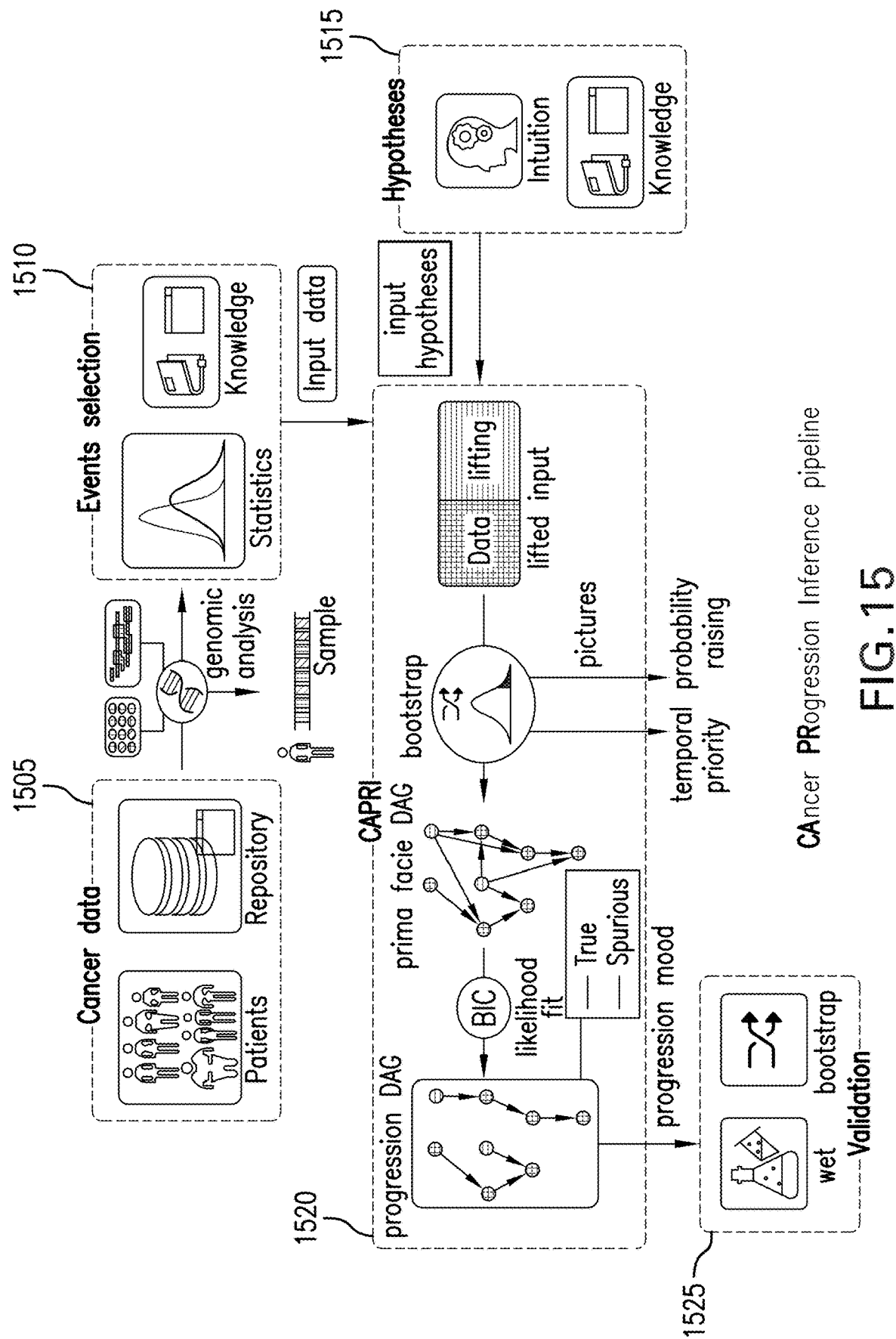
FIG. 15 is a diagram of an exemplary pipeline and/or procedure for a exemplary CAncer PRogression Inference ("CAPRI") according to an exemplary embodiment of the present disclosure.

A general pipeline for CAPRI's usage is depicted in a diagram of FIG. 15. CAPRI can be implemented in the open source R package TRONCO (e.g., second version, available at standard R repositories). The pipeline can start with data gathering 1505, either experimentally or via shared repositories, and genomic analysis to create, for example, somatic mutation or Copy-Number Variations profiles for each sample. Then, events can be selected (element 1510) via statistical analysis and biological priors, to construct a suitable input data matrix D which can satisfy CAPRI's assumptions. Hypothesis 1515 of any causal claim can then be generated, based on prior knowledge. CAPRI (element 1520) can then be executed, which can result in p-values for temporal priority and probability raising to be returned, along with the inferred progression model. Validation (element 1525) concludes the pipeline.

The performance of all the procedures were assessed with four different types of topologies: (i) trees, (ii) forests, (iii) DAGs without disconnected components and (iv) DAGs with disconnected components. Irrespective of the topology considered, atomic events were used, which can imply that the kind of causal claims that can be experimented with, can either be single or conjunctive. Based on exemplary Corollary 3, it sufficed to run CAPRI with 0=0. This can be consistent with the fact that the exemplary procedure can infer more general formulas if an input "set of putative causes, $\Phi=\emptyset$" can be given in addition—a fact which could have biased the exemplary analysis in the exemplary favor in the more general situation. For the sake of completeness, however, specific CNF formulas were also tested, as shown below.

Type (i-ii) topologies can be DAGs constrained to have nodes with a unique parent; condition (i) further restricts such DAGs to have no disconnected components, meaning that all nodes can be reachable from a starting root r. Practically, condition (i) satisfies $|\pi(j)|=1$ for j≠r, and $\pi(r)=\emptyset$, while in (ii) can be presented. This kind of topology can be either reconstructed with ad-hoc procedures (see, e.g., References 62, 63 and 65) or general DAG-inference techniques. (See, e.g., References 55, 56, 58, 69 and 70). Type (iii-iv) topologies can be DAGs which have either a unique starting node r, or a set of independent sub-DAGs. Similarly, condition (iii) satisfies $|\pi(j)|\geq 1$ for j≠r, and $\pi(r)=\emptyset$, while in (iv) can be facilitated to be present, as it was in condition (ii). This kind of topology may not be reconstructed with tree-specific procedures, and thus only certain procedures could be used for comparison. (See e.g., References 55, 56, 58, 69 and 70).

The selection of these different type of topologies may not be a mere technical exercise, but rather it can be motivated, in the exemplary application of primary interest, by heterogeneity of cancer cell types and possibility of multiple cells of origin. In particular, type (ii) with respect to (i) and type (iv) with respect to (iii), can be attempts at modeling independent progressions of a cancer via multiple roots. Clearly, these variations confound the inference problem further, since samples generated from such topologies will likely contain sets of mutations that can be correlated but can be pair-wise causally irrelevant—a well-studied and widely discussed problem. Finally, note that, to generate synthetic data according to (i-iv), the constraints on π(·) can be straightforwardly applied to the exemplary, system, method, and computer-accessible medium.

Exemplary Generating Synthetic Data.

Let n be the number of events to include in a DAG and let $p_{min}=0.05=1-p_{max}$, a DAG without disconnected components (e.g., an instance of type (iii) topology), maximum depth log n and where each node has at most w* parents (e.g., $|π(j)| \leq w^*$, for j≠r) can be generated as follows:
1: pick an event r E G as the root of the DAG;
2: assign to each j≠r an integer in the interval [2, [log n]] representing its depth in the DAG (e.g., 1 can be reserved for r), ensure that each level has at least one event;
3: for all events j≠r do
4: let l be the level assigned to e;
5: pick $|π(j)|$ uniformly over (0, w*], and accordingly define π(j) with events selected among those at which level l-1 was assigned;
6: end for
7: assign ∝(r) a random value in the interval [$p_{min}$, $p_{max}$];
8: for all events j≠r do
9: let y be a random value in the interval [$p_{min}$, $p_{max}$], assign ° (f)_y H a(x)

$$\propto (j) = y \prod_{x \in π(j)} \propto (x)$$

10: end for
11: return the generated DAG;

When an instance of type (iv) topology can be generated, the above exemplary procedure can be repeated to create its constituent DAGs. In this case, if multiple DAGs can be generated, each one with randomly sampled $n_i$ events, it can be beneficial that $|G|=\Sigma n_i=n$. When instances of type (i) topology can be needed where w*=1, and by iterating multiple independent sampling instances of type (ii) topology can be generated. When required DAGs were sampled, these can be used to generate an instance of the input matrix D for the exemplary reconstruction procedures.

To account for noise in the data, a parameter v∈(0, 1) can be introduced, which can represent the probability of each entry to be random in D, thus representing a false positive $\in_+$ and a false negative rate $\in_-$ where, for example:

$$\epsilon_+ = \epsilon_- = \frac{v}{2}.$$

Exemplary Performance Measures.

Synthetic data was used to evaluate the performance of the exemplary CAPRI as a function of dataset size, $\in_+$ and $\in_-$.

In general, since the exemplary interest lies primarily in the causal structure underlying the progressive phenomenon of cancer evolution, it can be beneficial to measure the number of genuine claims inferred (e.g., true positives, TP), and the number of unidentified spurious causes (e.g., false positives, FP). Similarly, false negative ("FN") can be called a genuine cause that fail to recognize as causal and true negative, and ("TN") can be a cause correctly identified as spurious. With these measures we evaluated the rates of precision and recall as follows:

$$\text{precision} = \frac{TP}{TP+FP}, \text{ and recall} = \frac{TP}{TP+FN}$$

The overall structural performance was measured in terms of the Hamming Distance ("HD"), (see, e.g., Reference 71), the minimum-cost sequence of node edit operations (e.g., deletion and insertion) that can transform the reconstructed topology into the true ones (e.g., those generating data). This exemplary measure corresponds to just the sum of false positives and false negative and, for a set of n events, can be bounded above by n(n-1) when the reconstructed topology contains all the false negatives and positives.

To estimate reliable statistics, the following exemplary approach can be used to assess the results. For each type of topology that can be considered, about 100 distinct progression models can be generated, and for each value of sample size and noise rate, about 10 datasets from each topology can be sampled. Thus, every performance entry (e.g., Hamming, precision or recall) can be the average of about 1000 reconstruction results. This can be the setting used in most cases, unless differently specified.

Exemplary Performance With Different Topologies And Small Datasets

Figure 16:
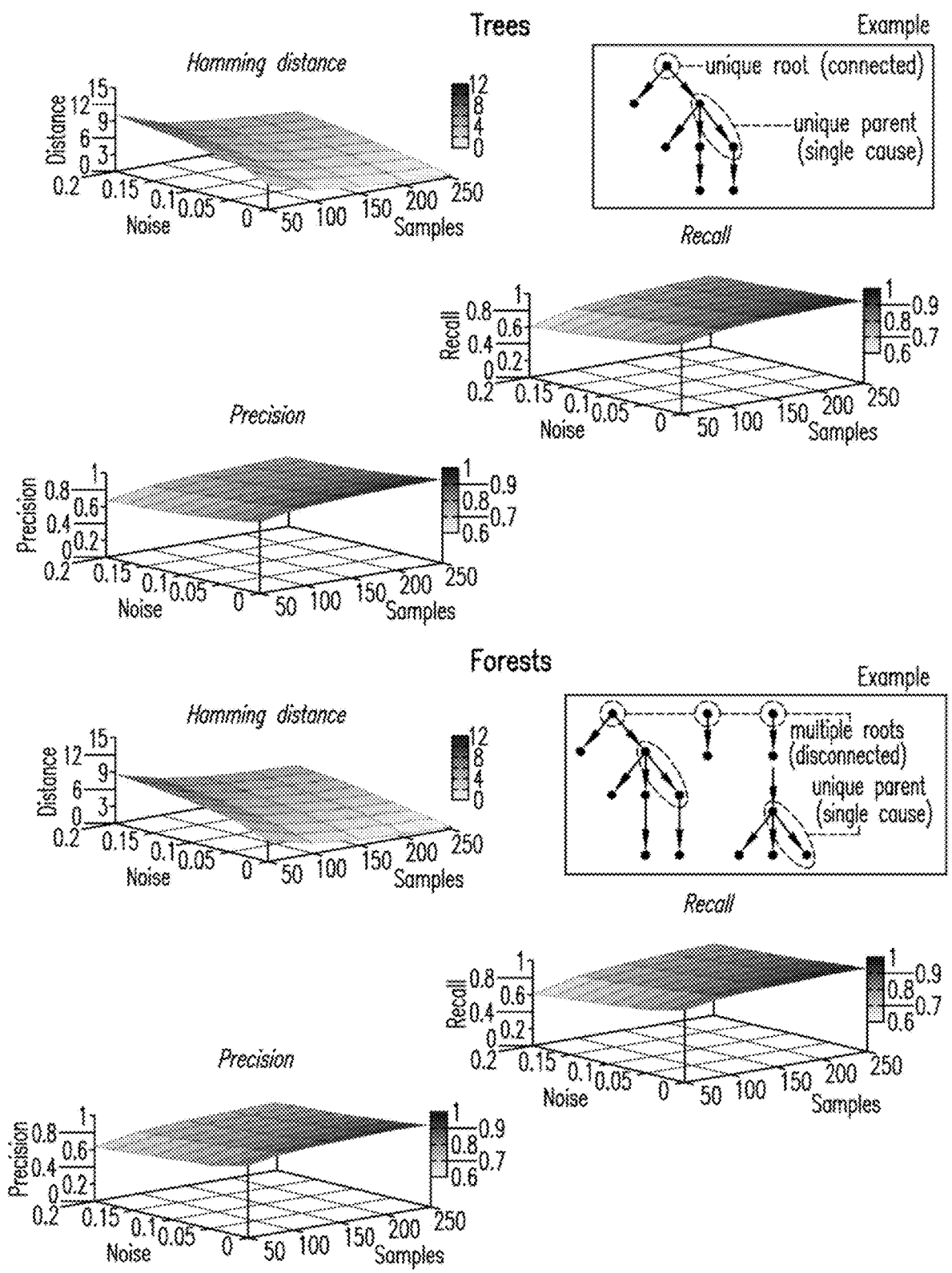
FIG. 16 is a set of diagrams and reconstruction trees for DAGs for small exemplary data sets according to an exemplary embodiment of the present disclosure.

The performance of CAPRI can be estimated for datasets with sizes that can be likely to be found in currently available cancer databases, such as The Cancer Genome Atlas, TCGA (see, e.g., Reference 72), for example, m≈250 samples, and about 15 events. The results are shown in FIG. 16, for topologies (i) and (ii), and FIG. 17, for topologies (iii) and (iv). There, all the results obtained by running the procedure with bootstrap resampling are shown, although results without this pre-processing leave the conclusions unchanged.

Figure 17:
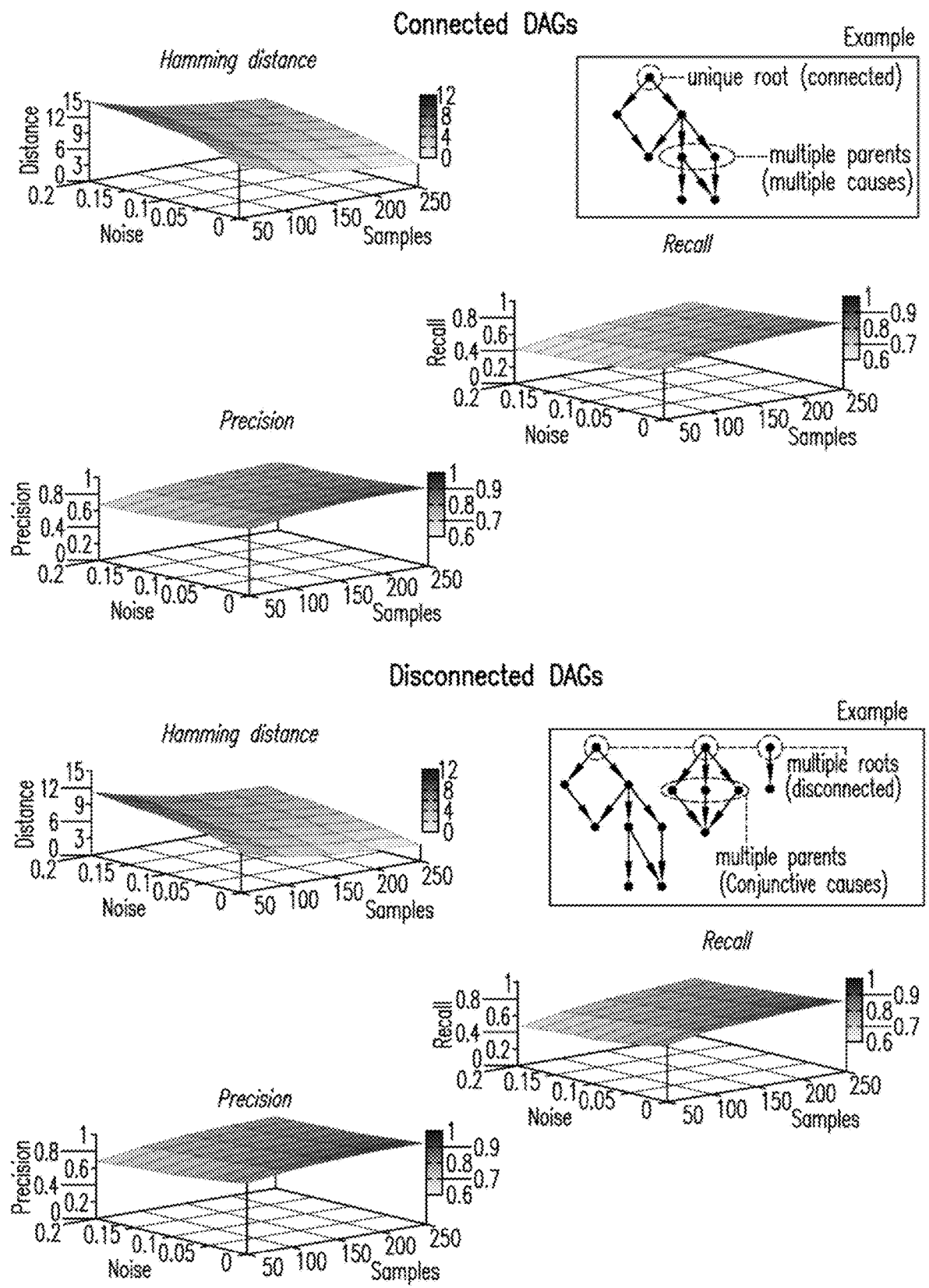
FIG. 17 is a set of diagrams and reconstruction trees and forests for small exemplary data sets according to an exemplary embodiment of the present disclosure.

Results suggest a trend that can be expected, which can be that performance degrades as noise increases and sample size diminishes. However, it can be particularly interesting to notice that, in various settings, the exemplary CAPRI almost converges to a perfect score even with these small datasets. This happens for instance with type (i-ii) topologies, where the Hamming distance almost drops to about 0 for m≥150. In general, reconstructing forests can be easier than trees, when the same number of events n can be considered. This can be a consequence of the fact that, once n can be fixed, forests can be likely to have less branches since every tree in the forest has less nodes. When reconstructing type (iii-iv) topologies, instead, the convergence-speed of CAPRI to lower Hamming distance can be slower, as one might reasonably expect. In fact, in those settings the distance never drops below about 3, and more samples would be required to get a perfect score. This can be considered to be a remarkable result, when compared to the worst-case Hamming distance value of 15·14=210. FIG. 17 also suggest that disconnected DAGs can be easier to reconstruct than connected ones, when a fixed number of events can be considered. Similarly to the above, this could be credited to the fact that the size of the conjunctive claims can generally be smaller, for fixed n. With respect to the precision and recall scores, it can be noted that the exemplary CAPRI can be robust to noise, since the loss in the score-values appear nearly unaffected by any increase in the noise parameter.

Exemplary Comparison With Other Reconstruction Techniques

For the following exemplary comparison, the following categories can be used:

Exemplary Structural approaches include such procedures as Incremental Association Markov Blanket ("IAMB") and the PC procedure, both subjected to log-likelihood maximization; (See, e.g., References 55 and 56).

Exemplary Likelihood: approaches encompass various maximum-likelihood approaches constrained by either the Bayesian Dirichlet with likelihood equivalence ("BDE") or the Bayesian Information Criterion ("BIC") scores; (See, e.g., References 69 and 70).

Exemplary Hybrid: approaches can be mixed approaches as exemplified by hidden Conjunctive Bayesian Networks ("CBN"), and Cancer Progression Inference with Single Edges (e.g., CAPRESE) which can be applied only to trees and forests. (See, e.g., References 58 and 62).

For all the exemplary procedures, their standard R implementations can be used, which can be, for example: for IAMB, BDE and BIC package bnlearn can be used, for the PC procedure package pcalg can be used, for CAPRESE TRONCO (e.g., first release) can be used, and for CBN h-cbn can be used. (See, e.g., References 73-75). Other exemplary procedures exist, but those which satisfied at least one of the following exemplary criteria were selected: they seemed more effective in inferring causal claims (e.g., IAMB and PC), they regularize the Bayesian overfit (e.g., BDE and BIC), they assume a prior (e.g., BDE) or they were developed specifically for cancer progression inference (e.g., CBN and CAPRESE).

Notice that all the exemplary procedures capable of inferring generic DAGs but CAPRESE (see, e.g., Reference 62) were selected, which can only be applied to infer trees or forests (e.g., type (i-ii) topologies). There exist other approaches specifically tailored for such topologies, (see, e.g., References 63 and 65), however since (see, e.g., Reference 62) it can be shown that CAPRESE can be better than other exemplary approaches. CAPRI can be considered to be in the Hybrid category, though its performance with all the other approaches was compared, with the aim of investigating which approach can be more suitable to reconstruct the topologies defined above.

Figure 18:
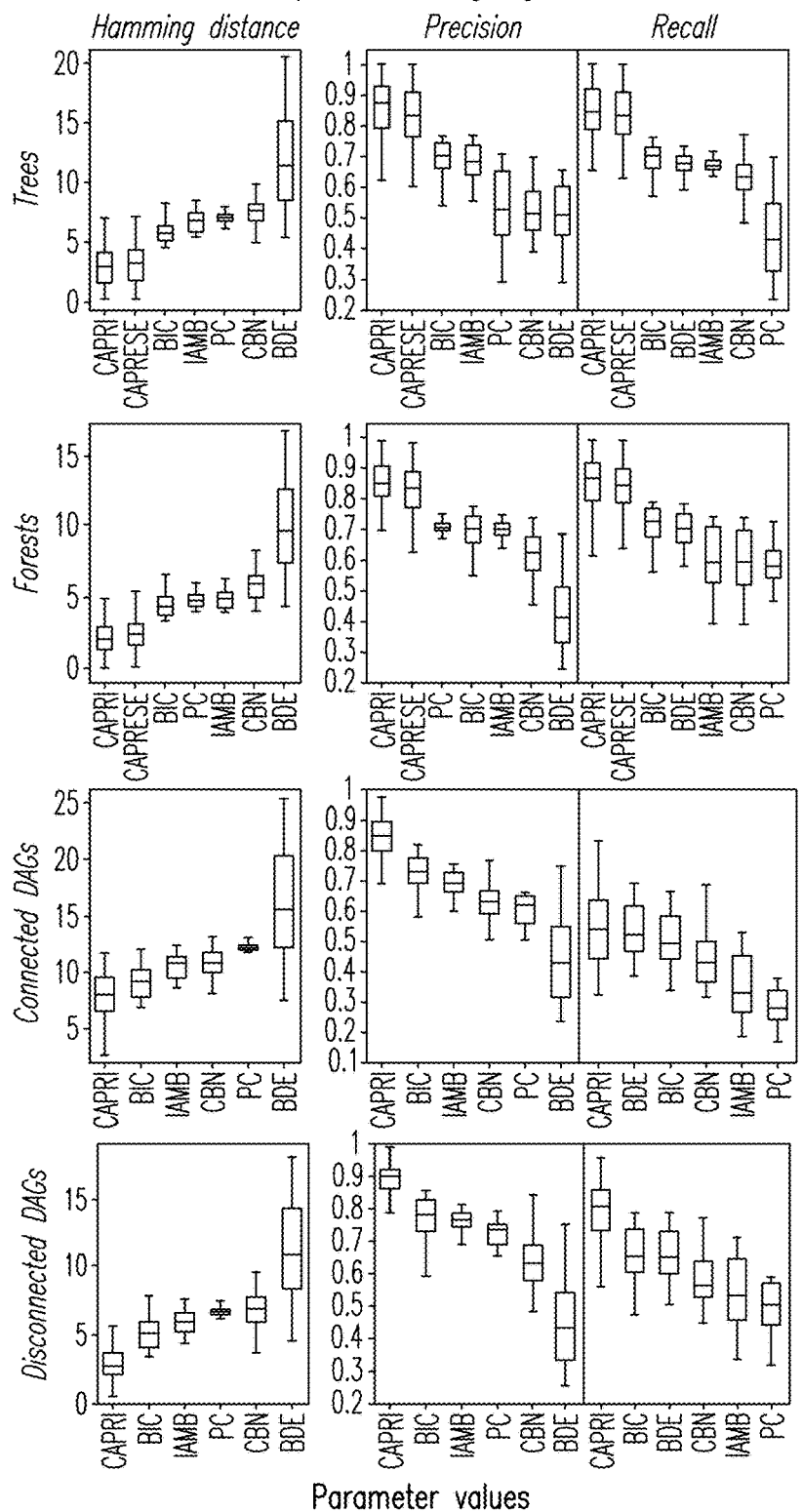
FIG. 18 is a set of diagrams illustrating exemplary conjunctive causal claims according to an exemplary embodiment of the present disclosure.
Figure 19:
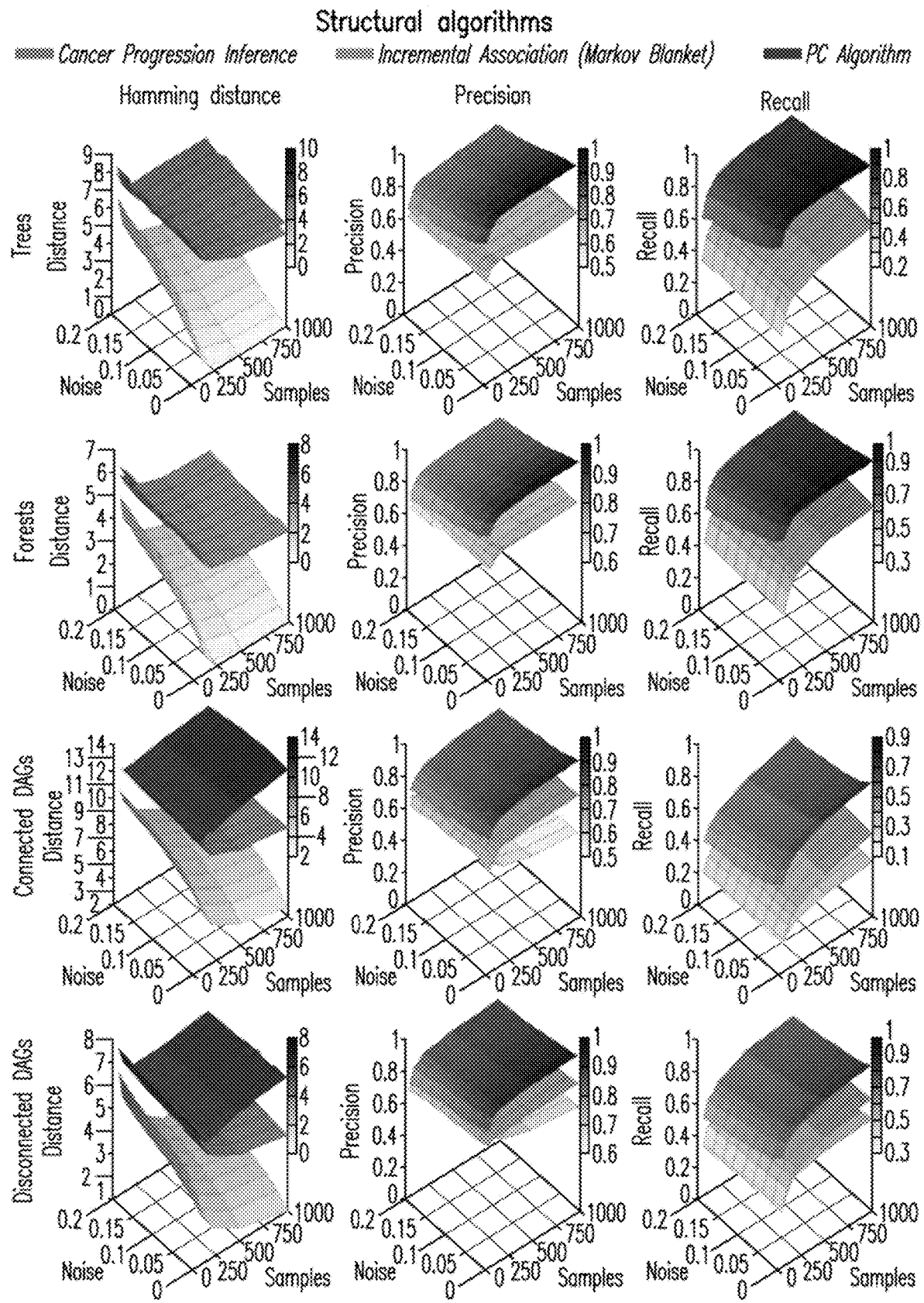
FIG. 19 is a set of graphs illustrating comparisons with conventional progression models.
Figure 20:
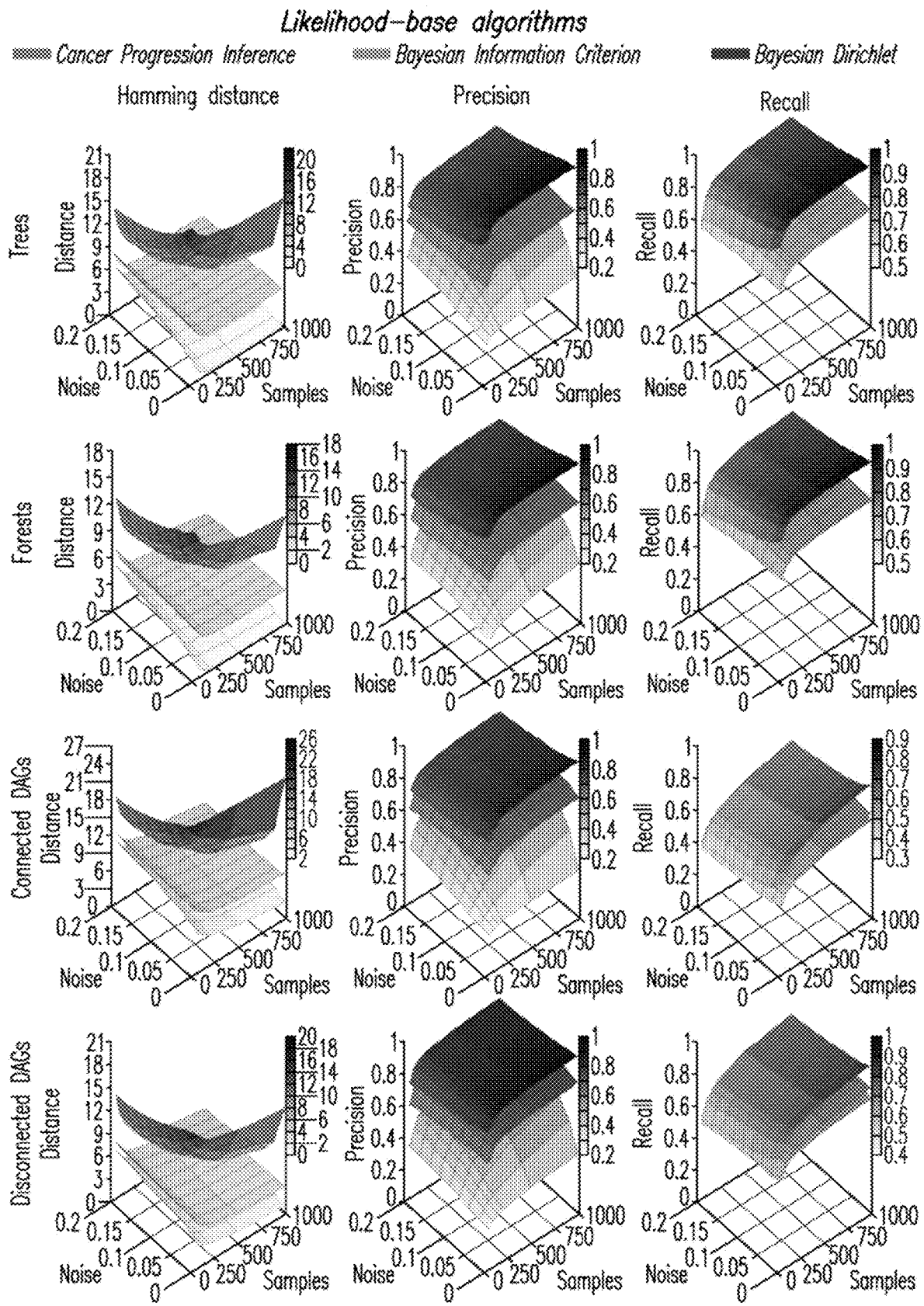
FIG. 20 is a further set of graphs illustrating comparisons with conventional progression models.
Figure 21:
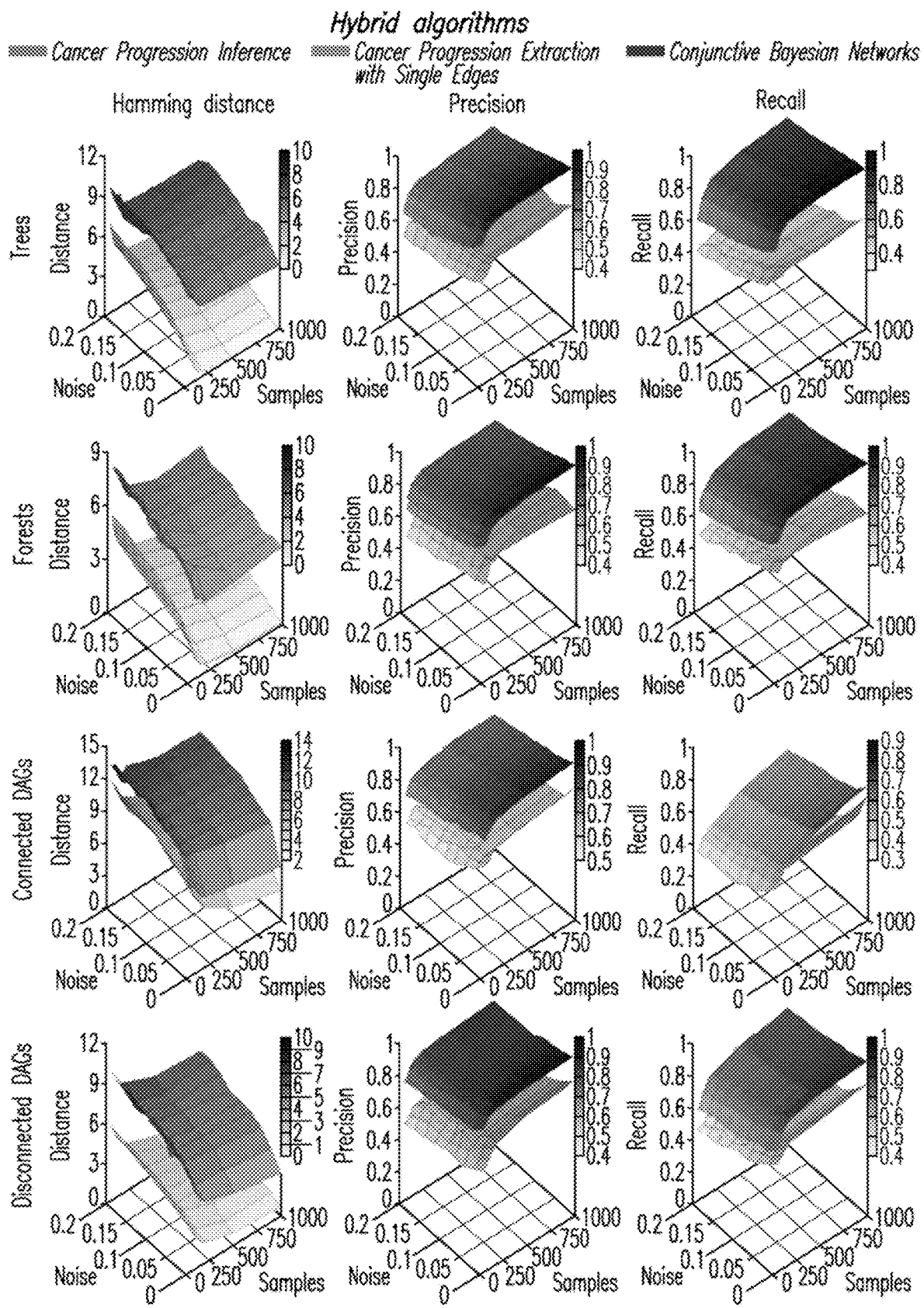
FIG. 21 is an even further set of graphs illustrating comparisons with conventional progression models.

The general trend is summarized in graphs of FIG. 18, where these exemplary procedures were ranked according to the median performance they achieve, as a function of noise and sample size, and provide the parameters used for comparison. In FIG. 19, CAPRI can be compared with the structural approaches (e.g., IAMB and PC). In FIG. 20, it can be compared with the likelihood approaches (e.g., BIC and BDE) and, in graphs of FIG. 21, it can be compared with the hybrid ones. Because of the high computational cost of running CBNs the number of ensembles performed can be about 100 for CBNs, while it can be about 1000 for all other exemplary procedures. While this strategy provides less robust statistics for CBNs (e.g., less "smooth" performance surfaces), it can be sufficiently accurate to indicate the general comparative trends and relative performance efficiency.

Exemplary Reconstruction Without Hypotheses: Disjunctive Causal Claims

For example, the exemplary procedure expects, as an input, all the hypothesized causal claims to infer more expressive logical formulas, for example, claims with pure CNF formulas or even disjunctive claims over atomic events. Nonetheless, it can be instructive to investigate its performance in two specific cases: namely, (i) without hypotheses ($\Phi=0$) and (ii) for datasets sampled from topologies with disjunctive causal claims.

To generate the input dataset, the exemplary generative procedure used for the other tests can be modified to reflect the switch from conjunctive to disjunctive causal claims. This task can be simple, since the labeling function a can be changed to account for the probability of picking any subset of the clauses in the disjunctive claim, and not picking the others. The exemplary DAGs can be used with about 10 events, and disjunctive causal claims with at most about 3 atomic events involved, which can be a reasonable size of a disjunctive claim, given the events considered. This exemplary setting can generally be harder than the one shown in FIGS. 19-21. Thus the performance can be expected to be somewhat inferior.

Figure 22:
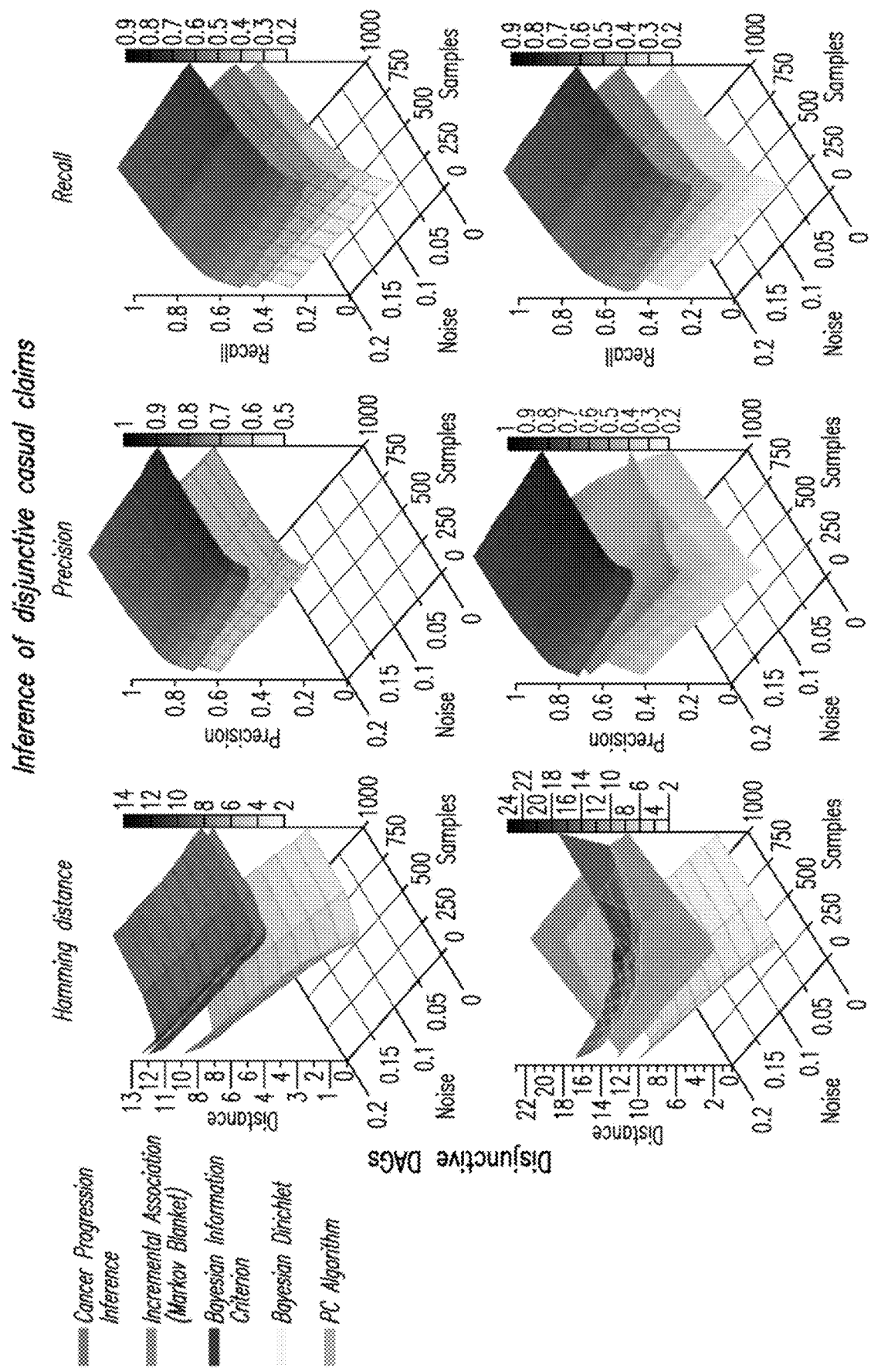
FIG. 22 is a set of charts illustrating the exemplary reconstruction of disjunctive causal claims with no hypothesis according to an exemplary embodiment of the present disclosure.

The exemplary CAPRI can be compared with other exemplary procedures used so far, the results of which are shown in FIG. 22, where $\Phi=0$, as noted earlier. The graphs confirm the trends suggested by previous analyses: namely, CAPRI can infer the correct disjunctive claims more often than the others. Note also that the performance can be measured on the reconstructed topology only, since, without input hypotheses, the exemplary procedure can evaluate only conjunctive claims, and does not facilitate different types of relations (e.g., disjunction) to be inferred automatically. However, observed performance improvement can be much lower, and the Hamming distance can fail to rise above about 4. Furthermore, convergence to optimal performance was not observed for m≤1000, and it appears not to be reachable even for m>>1000 (e.g., at least, when no hypotheses can be used). It can also be possible that, as n and the number of maximum disjunctive clauses increase, the result could be an even less satisfactory speed of convergence.

Exemplary Reconstruction With Hypotheses: Synthetic Lethality

Whether the exemplary CAPRI can infer synthetic lethality relations, when these can be directly hypothesized in the input set 0 can be considered. This can be confirmed with a test of the simplest form, for example:

$$a \oplus b \triangleright c,$$

for a set of events G={a, b, c} where progression can be forced from a to c to be preferential, for example, it appears with about a 0.7 probability while b to c does so with only about a 0.3 probability. Despite this being the smallest possible causal claim, the goal was to estimate the probability of such a claim being robustly inferable, when $\Phi=\{a \oplus b \triangleright c\}$, and its dependence on the sample size and noise. The performance of all the procedures can be measured, with an input lifted according to the claim so that all procedures start with the same initial pieces of information. The performance metric estimates how likely an edge from $a \oplus b$ to c could be found in the reconstructed structures.

Figure 23:
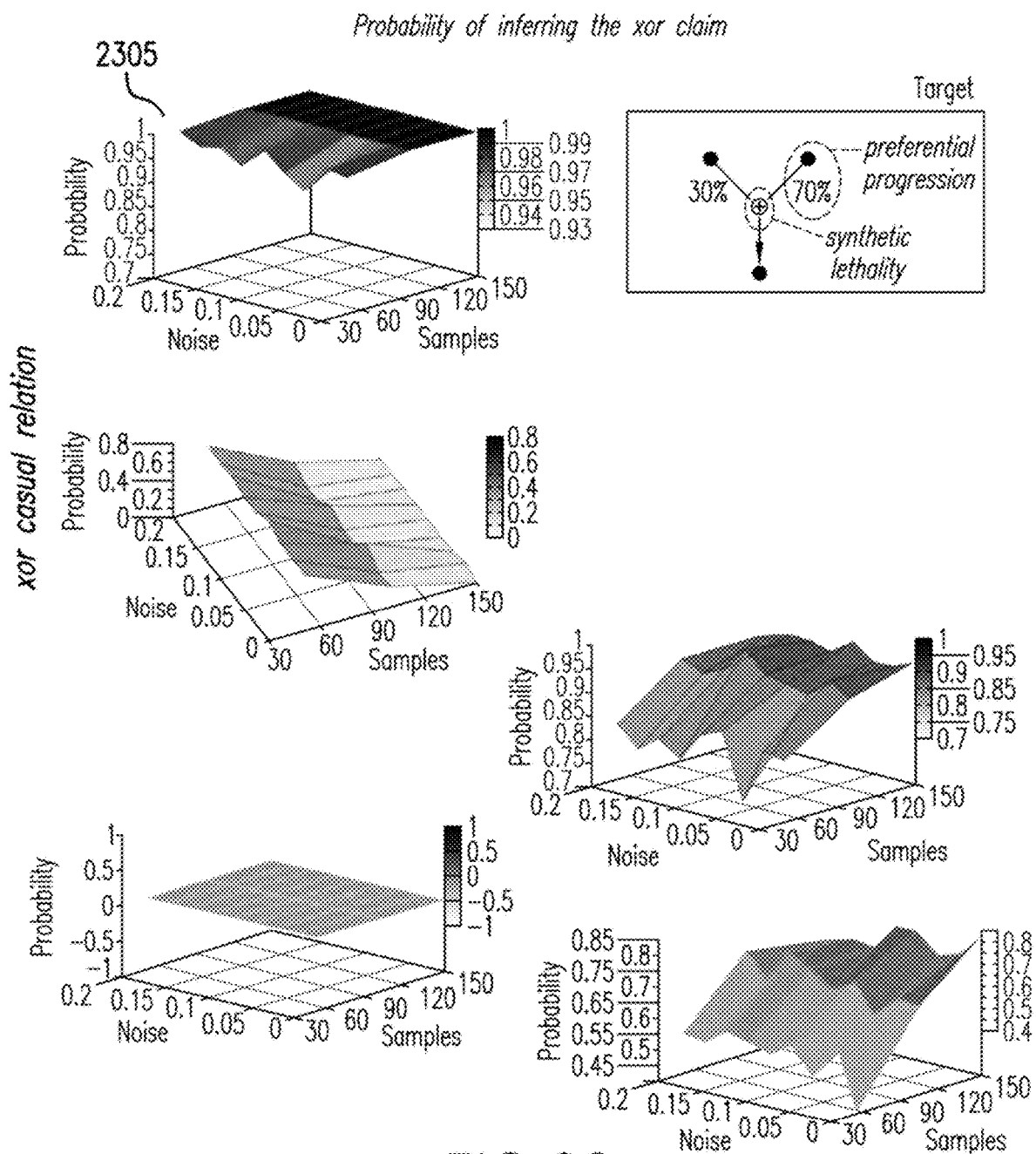
FIG. 23 is a set of diagrams illustrating the exemplary reconstruction of synthetic lethality with hypotheses according to an exemplary embodiment of the present disclosure.

Exemplary results of this exemplary comparison are shown in exemplary graphs of FIG. 23. For example, the exemplary CAPRI can succeed in inferring the synthetic lethality relation more than about 93% of the times, irrespective of the noise and sample size used. In particular, with m≥60, the exemplary procedure can infer the correct claim at any execution, thus suggesting that the exemplary CAPRI, with the correct input hypotheses, can infer complicated claims, many of which could have high biological significance. Naturally, it would be reasonably expected that the performance of any of these procedures would drop, were the target relations part of a bigger model.

Indeed, FIG. 23 illustrate exemplary graphs of the reconstruction with hypotheses of synthetic lethality. The average probability of inferring a claim aE b>c (e.g., synthetic lethality) can be seen, when this is provided in the input set D. Also shown is a probability for CAPRI, the likelihood-based algorithms with BIC and BDE scores, and the structural IAMB and PC procedure. Data can be generated from model 2305 (e.g., unbalanced "exclusive or" with a preferential progression), samples size ranges from about 30 to about 120, noise rate from about 0% to about 20% and about 1000 ensembles are generated for each configuration of noise and sample size. Results suggest that a threshold level on the number of samples exists such that CAPRI can infer the correct claim when <1_{a(R)b D c}.

Figure 24:
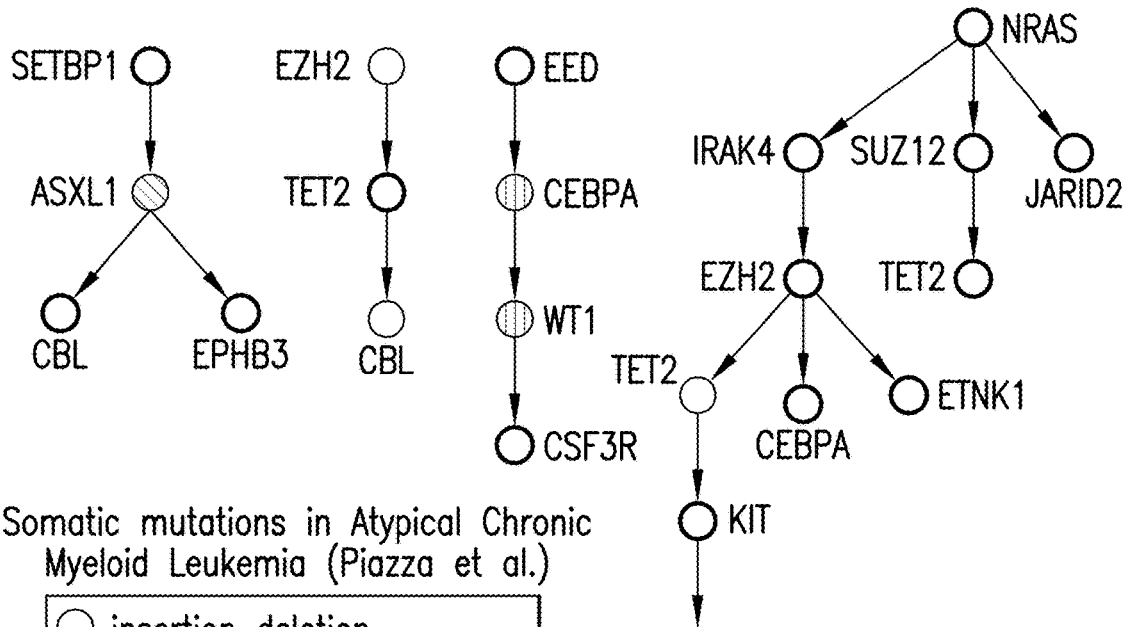
FIG. 24 is a diagram illustrating exemplary progression models according to an exemplary embodiment of the present disclosure.

The results of the exemplary reconstruction with other approaches are shown in exemplary diagrams of FIG. 24, while delineating the differences in the structures reconstructed by the exemplary CAPRI. FIG. 24 also shows the exemplary reconstruction with the structural procedure algorithm Incremental Association Markov Blanket with log-likelihood, and the likelihood-based procedure with Bayesian Information Criterion score. For example, only BIC infers the same relations on SETBP1 as those inferred by CAPRI. Somatic mutations considered here involve the following genes: SETBP1, NRAS, KRAS, TET2, EZH2, CBL, ASXL1, IDH2, IDH1, WT1, SUZ, SF3B1, RUNX1, RBBP4, NPM1, JARID 2, JAK2, FLT3, EED, DNMT3A, Ex23, CEBPA, EPHB3, ETNK1, GATA2, IRAK4, MTA2, CSF3R and KIT. In the plot we show only those events for which at least a causal claim was inferred.

Figure 25:
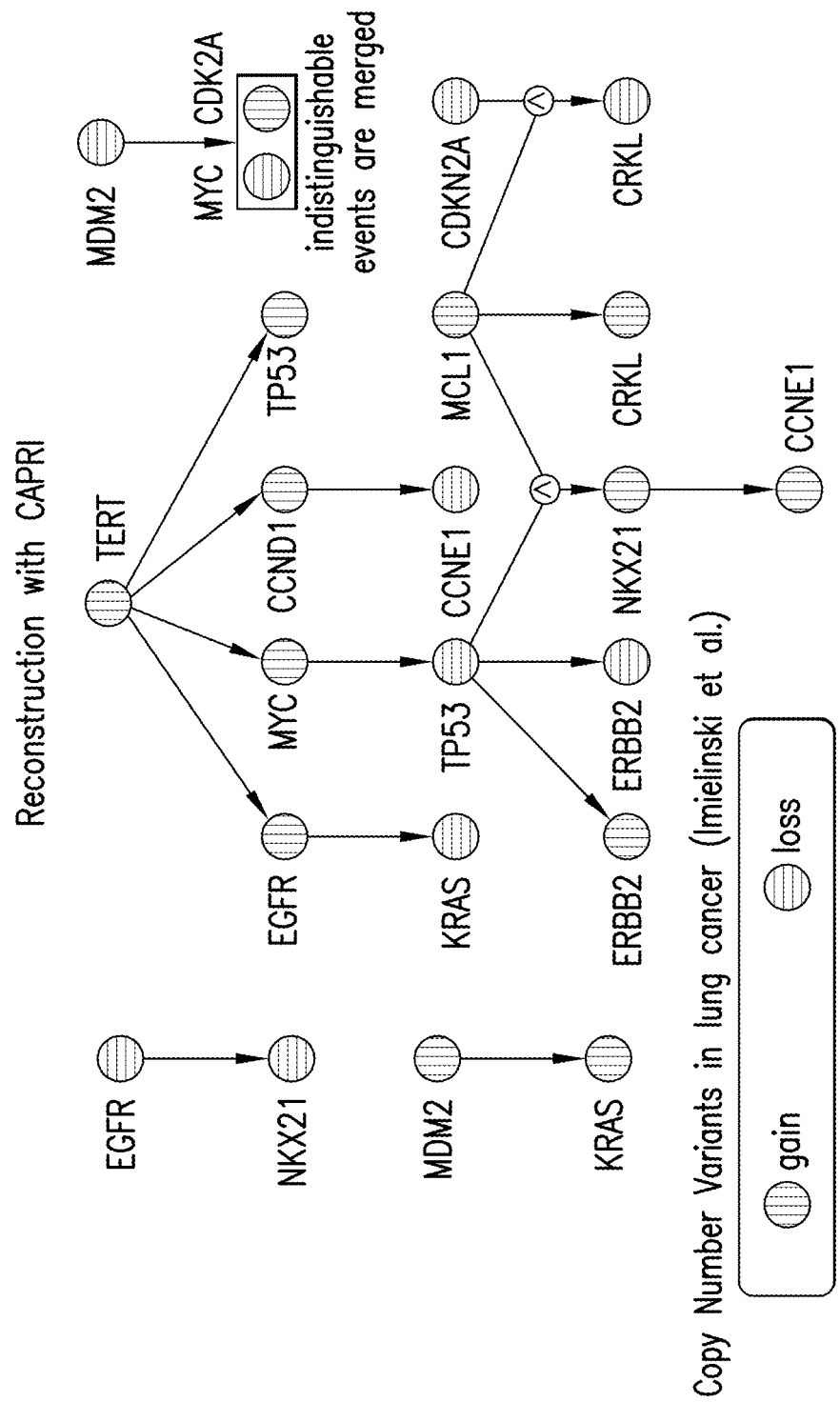
FIG. 25 is a diagram illustrating further exemplary progression models according to an exemplary embodiment of the present disclosure.

FIG. 25 shows a progression model of Copy Number Variants ("CNV"s) in lung cancer inferred with CAPRI from previously-published data.

Figure 26:
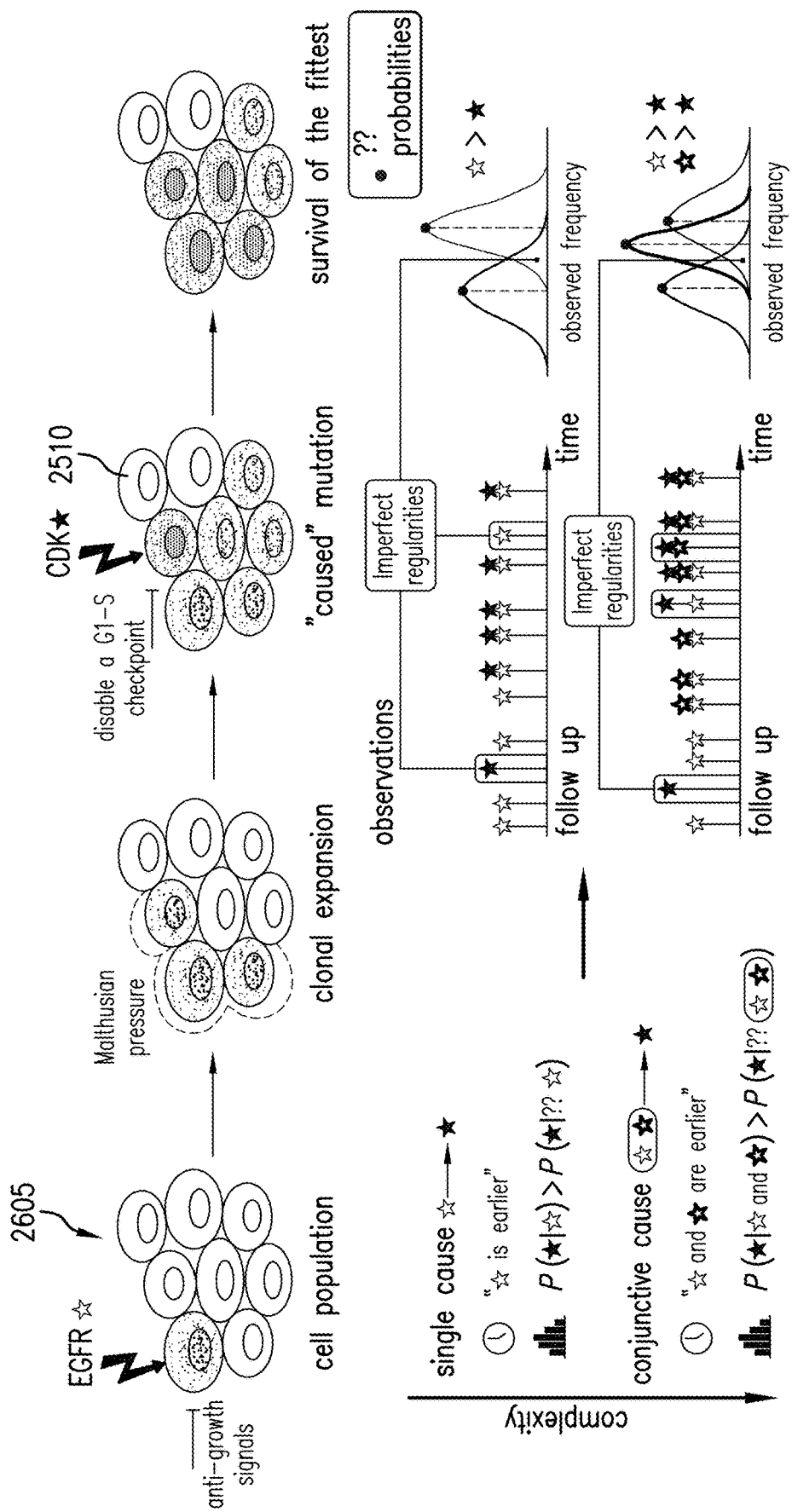
FIG. 26 is a diagram illustrating exemplary CAPRI procedures according to an exemplary embodiment of the present disclosure.

As show in exemplary illustrations of FIG. 26, the exemplary CAPRI procedure can examine cancer patients' genomic data to determine \causal" relationships among the chromosomal aberrations (mutations, copy number fluctuations, epigenetic medications, etc.) that modulate the somatic evolution of a tumor. When CAPRI concludes that aberration a (e.g., EGFR) 2605 causes aberration b (e.g., CDK 2510), it implies that the cells with a-mutation initially enjoyed a selective advantage resulting in a clonal expansion, which in turn created a Malthusian pressure (e.g., a micro-environment with deregulated glutamine) that allowed for the cells with b-mutations to emerge with higher fitness (e.g., by disabling a G1-S checkpoint). Such causal relations can be succinctly expressed using Suppes' probabilistic causation, which postulates that if a causes b, in the sense described here, then a occurs before b (e.g., temporal priority) and occurrences of a raises the probability of emergence of b (e.g., probability raising). These properties are checked by the exemplary CAPRI by combining ideas from model checking and Bayes network theory, as illustrated in FIG. 26. Since CAPRI uses model checking, it is capable of also testing complex causal claims: for example, conjunctive causal claims.

Figure 27:
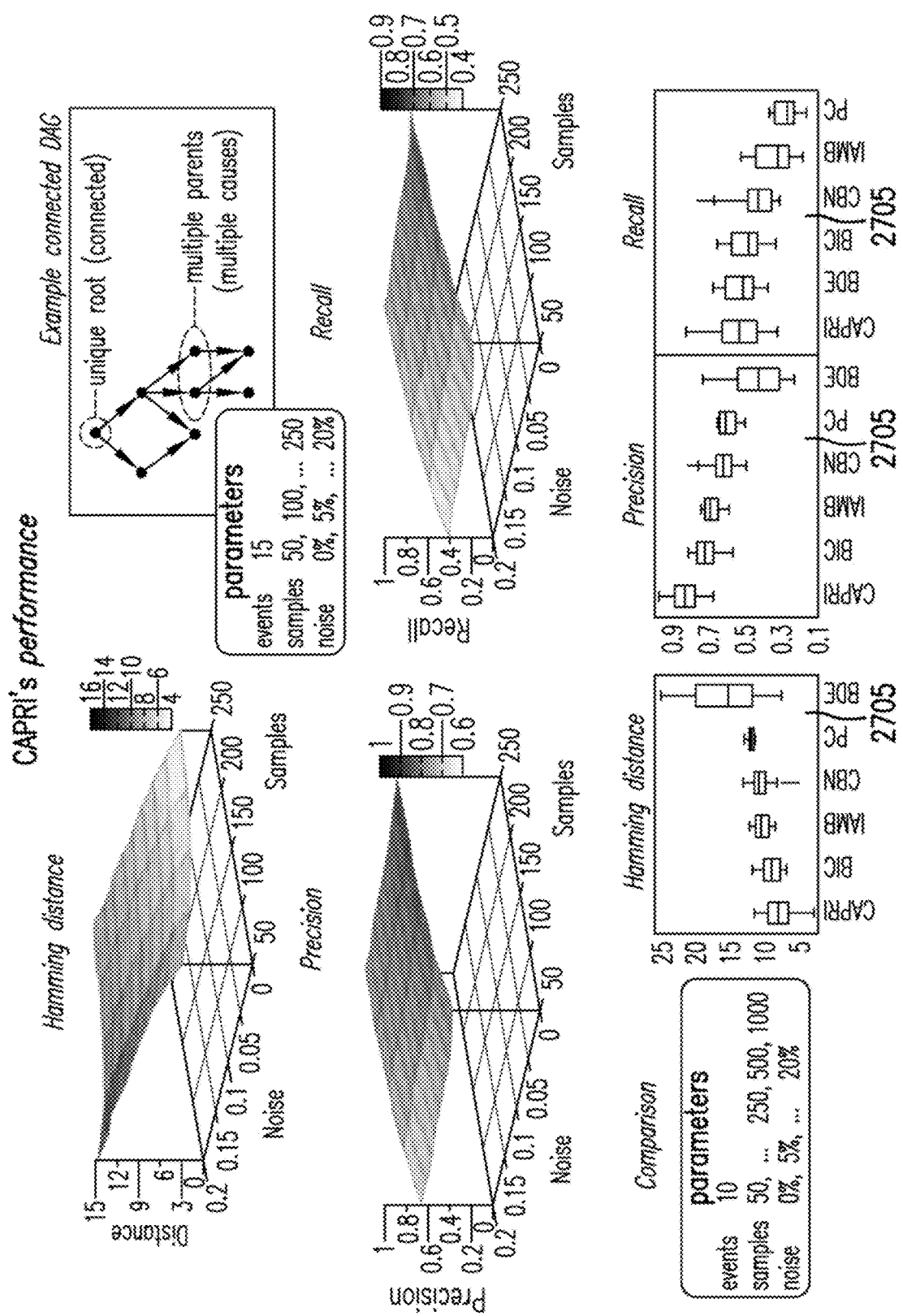
FIG. 27 is a set of exemplary diagrams and charts illustrating the accuracy and performance of the exemplary CAPRI according to an exemplary embodiment of the present disclosure.

As shown in exemplary graphs or FIG. 27, CAPRI's accuracy and performance was calibrated against various competing algorithms via extensive computer simulation. Hamming distance ("HD"), precision and recall of CAPRI were assessed with synthetic data generated by DAGs confluences. A unique progression and number of samples likely to be found in currently available databases such as TCGA, (e.g., m 250). Lower values of HD can imply that the exemplary procedure has mislabeled fewer genuine and spurious causes. Noise can account for both false positives and negatives. Graph 2705 plot comparison of CAPRI with IAMB, PC, BIC, BDE, CBN and CAPRESE, and is presented sorted according to the median performance.

Exemplary Model Description And Structure Learning

Exemplary Bayesian Networks

BN can be a statistical model that provides a sparse and succinct representation of a multivariate probability distribution over n random variables and encodes it into a sparse directed acyclic graph ("DAG"), G=(V, E) over n=|V| nodes, one per variable2, and |E|<<|V|² directed edges. A DAG can consist of a set of nodes (V) and a set of directed edges (E) between these nodes, such that there may be no directed cycles between any two nodes. In the exemplary setting, each node represents a Bernoulli random variable taking values in {0, 1}. The full joint distribution factors as a product of conditional probability distributions ("CPDs") of each variable, given its parents in the graph. In a DAG, the set of parents of node Xi consists of all the nodes with edges that point to Xi and can be written as P a(Xi). CPDs can be presented in, FIGS. 28A-28D, in which show a possible assignment of the parents and the corresponding probability of the child, which can be, a Bernoulli random variable $\epsilon$ {0, 1}, when it takes the value 1.

$$\mathcal{P}(x_1, \ldots, x_n) = \prod_{X_i \in V} \mathcal{P}(X_i = x_i \mid \text{Pa}(X_i) = x_{Pa(i)}). \tag{20}$$

The set of edges E can represent all the conditional independence relations between the variables. Specifically, an edge between two nodes Xi and Xj can denote statistical conditional dependence, no matter on which other variables can be conditioned. Mathematically this means that for any set of variables S⊆V\{Xi, Xj}, it holds that P(Xi, Xj|S)/=P (Xi|S)P(Xj|S). In the BN, the symmetrical nature of statistical dependence means that the graphs Xi→Xj and Xi←Xj encode the same conditional independence relations. Such graphs can be called I-equivalent (e.g., independence) and a set of such graphs a Markov equivalence class. In fact, any graphs that contain the same skeletons and v-structures can be Markov equivalent. Here, the skeleton can refer to the undirected set of edges, in which Xi→Xj and Xi←Xj both map to Xi↔Xj, and a v-structure refers to a node with a set of at least two parents, in which no pair of parents share an edge. In BN terminology, a parent with no shared edge can be considered "unwed parents." For this reason, the v-structure can often be called an immorality. In other texts, it can be referred to as an unshielded collider.

Exemplary Monotonic Progression Networks

A class of Bayesian networks over Bernoulli random variables called monotonic progression networks ("MPNs") can be defined. (See e.g., Reference 86). MPNs formally represent informal and intuitive notions about the progression of persistent events that accumulate monotonically, based on the presence of other persistent events. The terms variable and event can be used interchangeably. The conditions for an event to happen can be represented in the CPDs of the BN using probabilistic versions of canonical Boolean operators, namely conjunction (^), inclusive disjunction (V), and exclusive disjunction (⊕), as well as any combination of propositional logic operators. FIGS. 28A-28D show an example of the CPDs associated with various operators.

While this exemplary framework can facilitate any formula to define the conditions of the parent events conducive for the child event to occur, a simpler design can be chosen to avoid the complexity of the number of possible logical formulas over a set of parents. Namely, three types of MPNs can be defined (e.g., a conjunctive MPN ("CMPN"), a disjunctive MPN ("DMPN"), sometimes referred to as a semi-monotonic progression network ("SMPN") and an exclusive disjunction MPN ("XMPN"). The operator associated with each network type can define the logical relation among the parents that should hold for the child event to take place. Arbitrarily complex formulas can still be represented as new variables, whose parent set can consist of the variables in the formula and whose value can be determined by the formula itself. This exemplary design choice assumes that most of the relations in a particular application fall under one category, while all others can be special cases that can be accounted for individually. Mathematically, the CPDs for each of the MPNs are defined below as, for example:

CMPN:

$$Pr(X=1|\Sigma P\alpha(X)<|P\alpha(X)|)\leq \epsilon,$$

$$Pr(X=1|\Sigma Pa(X)=|Pa(X)|)>\epsilon.$$

DMPN:

$$Pr(X=1|\Sigma Pa(X)=0)\leq \epsilon,$$

$$Pr(X=1|\Sigma Pa(X)>0)>\epsilon.$$

XMPN:

$$Pr(X=1|\Sigma Pa(X)\neq 1)\leq \epsilon,$$

$$Pr(X=1|\Sigma Pa(X)=1)>\epsilon.$$

The inequalities above define the monotonicity constraints specific to each type of MPN, given a fixed "noise" parameter E. When a particular event occurs, despite the monotonicity constraint, the sample can be negative with respect to that event. If the event does not occur or occurs in compliance with the monotonicity constraint, then it can be a positive sample of that event. Note that in the case in which E=0, the monotonicity constraints can be deterministic, and all samples can be positive. By convention, the rows of a CPD can be referred to as positive, and negative rows and θ+can refer to the conditional probability of some positive row I, and θ– can refer to the conditional probability of some negative row i.

Exemplary Structure Learning

Many procedures exist to carry out structure learning of general Bayesian networks. They usually fall into two families of procedures, although several hybrid approaches have been recently proposed. (See e.g., References 83 and 92). The first, constraint based learning, explicitly tests for pairwise independence of variables conditioned on the power set of the rest of the variables in the network. The second, score based learning, constructs a network to maximize the likelihood of the observed data, with some regularization constraints to avoid overfitting. Because the data can be assumed to be independent and identically distributed (e.g., i.i.d), the likelihood of the data can be the product of the likelihood of each datum, which in turn can be defined by the factorized joint probability function described above. For numerical reasons, log likelihood ("LL") can usually be used instead of likelihood, and thus the likelihood product becomes the log likelihood sum.

The latter approach can be built on, specifically relying on the Bayesian Information Criterion ("BIC") as the regularized likelihood score. The score can be defined below as, for example:

$$score_{BIC}(D, G) = LL(D \mid G) - \frac{\log M}{2} \dim(G). \quad (21)$$

For example, G can denote the graph (e.g., including both the edges and CPDs), D can denote the data, M can denote the number of samples, and dim(G) can denote the number of parameters in the CPDs of G. The number of parameters in each CPD can grow exponentially with the number of parents of that node. For the exemplary networks over events, dim(G) for a single node X can be 2|Pa(X)|. Thus, the regularization term—dim(G) can favor nodes with fewer parents or equivalently, graphs with fewer edges. The coefficient log M/2 essentially weighs the regularization term, such that the higher the weight, the more sparsity will be favored over "explaining" the data through maximum likelihood. The likelihood can be implicitly weighted by the number of data points, since each point contributes to the score.

With sample size enlarging, both the weight of the regularization term and the "weight" of the likelihood can increase. However, the weight of the likelihood can increase faster than that of the regularization term. Mathematically, it can be said that the likelihood weight can increase linearly, while the weight of the regularization term can increase logarithmically. Thus, with more data, likelihood will contribute more to the score. Intuitively, with more data, the exemplary observations can be trusted more, and can have less need for regularization, although this term never completely vanishes.

Statistically speaking, BIC can be a consistent score. (See e.g., Reference 92). In terms of structure learning, this exemplary property can imply that for sufficiently large sample sizes, the network with the maximum BIC score can be I-equivalent to the true structure, G*. From the above, G can have the same skeleton and v-structures as G*, though nothing can be guaranteed regarding the orientation of the rest of the edges. For most graphs, therefore, BIC cannot distinguish among G* plus all other possible graphs, and thus may not be sufficient for exact structure learning. In the case of BNs with structured CPDs, such as MPNs, it can be possible to improve on the performance of BIC. For example, the BIC score has been modified below to drastically improve performance in learning the orientations of all edges.

Exemplary Observational VS. Biological Noise

The notion of probabilistic logical relations among variables to represent disease progression has been developed in two families of models. These two exemplary approaches diverge in the treatment of noise, or equivalently, in how the model produces negative, or non-monotonic, samples. The first approach encodes a notion of experimental, or observational, noise, in which negative samples can result from incorrect labeling of the events. (See e.g., References 89 and 96). In the exemplary system, method, and computer-accessible medium, according to an exemplary embodiment of the present disclosure, each generated sample can be initially positive in all variables, and then can have several event values inverted, with a certain probability. The second approach can encode biological or causal noise, in which negative samples result from the activation of events by some non-canonical causes, in the absence of canonical ones. (See e.g., Reference 86). In exemplary models like these, the level of noise corresponds to the probability that an event occurs despite the absence of its parents.

Observational noise and biological noise have different statistical properties that affect how the model can be learned. Namely, observational noise can often be assumed to be unbiased and have a Gaussian distribution and thus by the strong law of large numbers, converges to zero for a sufficiently large number of observations. In contrast, biological noise can be asymmetric, and can persist even with large sample sizes. One of the key consequences of these differences can be the following. While the asymptotic marginal probabilities of the variables can be the same for all levels of noise in the observational noise model, for biological noise, however, the marginal probabilities can be very sensitive to the level of noise, irrespective of how large the sample size can be.

Exemplary Development Of Causal Score

An exemplary score can be presented (e.g., the one used in Polaris), that can statistically be consistent, like BIC, and can correctly orient edges based on the monotonicity of the progression relation, like DiProg, but without knowing the parameter E a priori. The basic idea behind the score can be a heuristic for the likelihood of each sample such that the likelihood reflects both the probability of the sample being generated from its CPD, and the probability that the CPD obeys the monotonicity constraints of the true model. The latter may not be computed without knowledge of E, and thus relies on a nonparametric notion of monotonicity to estimate the underlying CPD. Below, is an explanation of the development of Polaris and with its philosophical foundations compared to its asymptotic convergence properties.

Exemplary Suppes Causality

The score can be modeled after the asymmetrical portion, a, of the causal score, presented above. (See e.g., Reference 93). This part of the score can be based on Suppes's theory of causality for distinguishing prima facie causes from non-causal correlations. Suppes stipulates two conditions for event C to cause event E. First, C must raise the probability of E. In the exemplary statistical model, this means that $P(E|C) > P(E|c^-)$. Second, C must precede E in time. Unfortunately, this model, may have no notion of time and may not directly infer temporal priority.

However, under the condition that C can be the unique cause of E, it can be beneficial that C must appear every time E appears but not vice versa. Therefore, the number of occurrences of C must be larger than that of E. From this, it can be easy to see that $P(C) > P(E)$. In fact, this property of temporal priority also holds for conjunctions over several parents, as E will only appear when all its parents can be present.

The α score for a causal relation can be defined as $$\alpha_{xi} = \begin{cases} 1, & \text{for a positive row;} \\ \frac{\hat{\theta}_x^+ - \hat{\theta}_{xi}^-}{\hat{\theta}_x^+ + \hat{\theta}_{xi}^-}, & \text{for a negative row} \end{cases}.$$

This definition can be proved to meet both the probability raising and temporal priority conditions explained above. However, only the tree structured graphs were considered, in which every node has at most 1 parent and at most 1 negative row in its CPD. (See e.g., Reference 93). Applied to an MPN, the true α value for each CPD can be strictly positive for each edge—a consequence of the constraint that $P(E|C) > P(E|c^-)$ for all MPNs. Thus, when several graphs can be considered to fit to observed data, an estimated α with a negative value (e.g., below a threshold) means that the corresponding CPD breaks the monotonicity constraint. However, an estimated α with a positive value (e.g., above a threshold) puts more faith in the legitimacy of that CPD. Otherwise, the interpretation of CPD can be ambiguous. Justified by these intuitive observations, α can serve as a faithful proxy for monotonicity in tree structured MPNs.

Exemplary Weighted Likelihood Without A Priori Knowledge Of Model Parameters

More general, DAG structured models can be considered in which CPDs can have more than one negative row. To handle this, a α score can be assigned to each row of the CPD, as defined below. A notation of αxi can be used to denote the α value corresponding to row i of the CPD of variable X. By the exemplary convention, θ− can denote the probability of negative row i and θ+ the probability of the one positive row of the CPD of X. This assumption may only be true for CMPNs. This notation can be extended to DMPNs and XMPNs later.

$$C \to E \text{ as } \frac{\mathcal{P}(E|C) - \mathcal{P}(E|C)}{\mathcal{P}(E|C) + \mathcal{P}(E|C)}.$$

Thus, as described above, a can now be a heuristic for the monotonicity of each row of a CPD rather than the CPD as a whole. It follows that each negative sample has a ⸱ corresponding α between −1 and 1. Thus, each negative sample can be weighed by its a value to reflect the exemplary belief that its CPD row conforms to the monotonicity constraints. This strategy leads to CPDs with high monotonicity to be favored through their samples, whereas CPDs with poor monotonicity can be penalized through their samples. Moreover, by handicapping the samples instead of the CPDs directly, rows whose conditional probabilities were estimated with more samples to have a larger effect on the score were used. The resulting α-weighted likelihood score (e.g., scoreαWL) for variable X given sample d can be defined below, where and $\hat{\theta}^+ + \hat{\theta}^-$ can be empirical estimates of their respective parameters. Note that because of the indicator function in the exponent of the α term in the score, only the α term of the row that corresponds to the sample can be used to weigh the likelihood. Specifically, if the sample can be positive, the likelihood may not be altered, whereas if the sample can be negative, the likelihood can be penalized in proportion to the α score for that sample's corresponding row.

$$score_{\alpha WL}(X:d) = Pr(X = d_x \mid Pa(X) = d_{Pa(X)}) \cdot \prod_{i \in |CPD_x|} \alpha_{xi}^{1(d_{Pa(X)} = CPD_x(i))}$$

The exemplary score used for structure learning can include the BIC regularization term, so the full combined score for a single variable X given a datum d is below. The last line defines the composed score for the all the variables, V, over all the data, D.

$$score_{\alpha WL,BIC}(X:d) =$$

$$\log\left[Pr(X = d_x \mid Pa(X) = d_{Pa(X)}) \cdot \prod_{i=1}^{|CPD_x|} \alpha_{xi}^{1(d_{Pa(X)} = CPD_x(i))}\right] -$$

$$\frac{\log M}{2} \dim(X \mid Pa(X)),$$

$$score_{\alpha WL,BIC}(X:d) =$$

$$\log\left[Pr(X = d_x \mid Pa(X) = d_{Pa(X)}) + \prod_{i=1}^{|CPD_x|} 1(d_{Pa(X)} = CPD_x(i))\log \alpha_{xi}\right] -$$

$$\frac{\log M}{2} \dim(X \mid Pa(X)),$$

$$score_{\alpha WL,BIC}(X:d) = LL(d_x, d_{Pa(X)} \mid G) +$$

$$\alpha(X \mid d) - \frac{\log M}{2} \dim(X \mid Pa(X)),$$

and, finally $$score_{\alpha WL,BIC}(G:D) = LL(D \mid G) + \sum_{d \in D}\sum_{X \in V} \alpha(X \mid d) - \frac{\log M}{2} \dim(G).$$

This can be further written as, for example:

$$\alpha(X \mid d) = \sum_{i \in |CPD_x|} 1(d_{Pa(x)} = CPD_x(i))\log \alpha_{xi}$$

Exemplary Multiplicative Factors

Asymptotically, the BIC can be known to reconstruct the correct skeleton and orient edges in immoralities correctly. Since a score to enhance this result further and orient the remaining edges correctly without disturbing the correct skeletal structure can be beneficial, a new weight can be introduced to the whole monotonicity term of the score. This exemplary weight can be structured to approach zero in the limit, as the sample size approaches infinity. Thus, for small sample sizes, the monotonicity component can play a larger role in the overall score. Then, as the BIC component converges to a more stable structure, the monotonicity component can choose the exact structure among several equally likely ones. For these asymptotic results, the simplest weight can be chosen that can be inversely proportional to the sample size: 1/M. The final score developed for structure learning of MPNs is below.

$$score_{Polaris}(G:D) = LL(D \mid G) + \frac{1}{M}\sum_{d \in D}\sum_{X \in V} \alpha(X \mid d) - \frac{\log M}{2} \dim(G).$$

It can be proved mathematically that this score asymptotically learns the correct exact structure of an MPN under certain conditions—especially, conditions enforcing the absence of transitive edges and a sufficiently low E parameter. In practice, however, it was found that the exemplary system, method, and computer-accessible medium according to an exemplary embodiment of the present disclosure, can converge on the correct structure for graphs with transitive edges and non-negligible E values. (See e.g., FIGS. 29A-29D).

Exemplary Definition 8 (e.g., Faithful Temporal Priority)

In a monotonic progression network G, if there exists a path from Xj to Xi, then the temporal priority between Xi and Xj can be faithful if P(Xj)>P(Xi).

Exemplary Theorem 6 (e.g., Convergence Conditions for Polaris)

For a sufficiently large sample size, M, under the assumptions of no transitive edges and faithful temporal priority relations (see e.g., Definition 8 above), between nodes and their parents, at least for nodes that have exactly 1 parent, optimizing Polaris can converge to the exact structure.

Exemplary Extension To DMPNs And XMPNs

The score stated above can work for all three classes of MPNs, with minor modifications to the definition of a, depending on the monotonicity constraints. A main difference between CMPNs and the other two types lies in the fact that each CPD corresponding to a CMPN can have exactly one positive row. In contrast, the CPDs in DMPNs can have exactly one negative row, and the CPDs in XMPNs can have multiple positive and negative rows. (See e.g., FIGS. 28A-28D). Specifically, the only negative row for DMPNs can be the case in which all parent nodes equal zero. For XMPNs, any row with exactly one parent event equal to one can be a positive row and all the rest can be negative rows. In order to extend the definition of a to DMPNs and XMPNs, all events that correspond to the positive rows of a CPD can be treated as one event. The probability of this large event can be called 0+, just as in the CMPN case, and it is defined below for both DMPNs and XMPNS.

$$\theta_{DMPN}^+(X) = \mathcal{P}(\Sigma(Pa(X) > 0),$$

$$\theta_{XMPN}^+(X) = \mathcal{P}(\Sigma Pa(X) = 1).$$

Exemplary Temporal Priority In The Presence Of Biological Noise

The α score for learning models can enforce both probability raising and, for conjunctive or singleton parent sets, temporal priority. (See e.g., References 93 and 96). The model of noise considered there has the property that, for sufficient large sample sizes, by the large of large numbers, the probability of a negative sample can approach zero. However, in the exemplary model of noise, θ−'s can be fixed parameters and may not approach zero. Thus, temporal priority cannot always be correctly imputed for all causal relations. That can be, C→E does not necessary mean that P(C)>P(E).

Instead, temporal priority can be decided by E, θ+ and the marginal probabilities, as specified in the equation below. Specifically, high E and correspondingly high θ−, low θ+ and close marginal probabilities can make it easier to reverse the observed temporal priority.

$$\mathcal{P}(X) = \mathcal{P}(Pa(X) = 1) \cdot \theta^+ + \sum_i (1 - \mathcal{P}(Pa(X) = CPDx(i))) \cdot \theta_i^-.$$

Exemplary MPN Structure Learning

Exemplary Filtering

Before optimizing the score, there can be certain parent sets may be eliminated as hypotheses. This pre-optimization filtering can be done for two reasons. First, it can prevent the optimization procedure from selecting a spurious parent set. Second, it can speed up computation significantly by not computing the full score for that hypothetical parent set. The α score can be used to filter hypotheses, rejecting those solutions that can create a negative α for at least one row of the CPD. This α-filter can be used for all types of MPNs, and can greatly improve efficiency without eliminating too many true hypotheses. In fact, it can be proven mathematically that asymptotically, the α filter will be free of any mistakes.

Exemplary Lemma 1 (Convergence of A-Filter)

For a sufficiently large sample size, M, the α-filter produces no false negatives for CMPNs, DMPNs and XMPNs.

Exemplary Optimizing the Score with GOBNILP

After pruning the hypothesis space with the α filter, an exemplary GOBNILP can be used, a free, publicly available BN structure learning package, to find the network with the highest Polaris score. (See e.g., References 80, 85 and 91). Given an upper bound on the maximum number of parents (e.g., by default 3), GOBNILP can expect as input the scores for each node given each possible combination of parents. For each node, the exemplary code produces this information with a depth first search through the power set of the rest of the nodes in the graph. Any hypothetical parent set that can be filtered may not simply be included as a possible solution for that node in the input to GOBNILP.

Further Exemplary Results

Exemplary Performance On Synthetic Data

Several experiments were conducted to test the performance of the exemplary Polaris on data generated from synthetic networks, all on ten variables. The network topologies were generated randomly, and the CPDs were generated according to the monotonic constraints imposed by the type of MPN and the value of E. These networks were sampled with different sample sizes. In all experiments, the performance metrics were measured over fifty synthetic topologies sampled ten times, for each value of E and sample size.

Figure 29A:
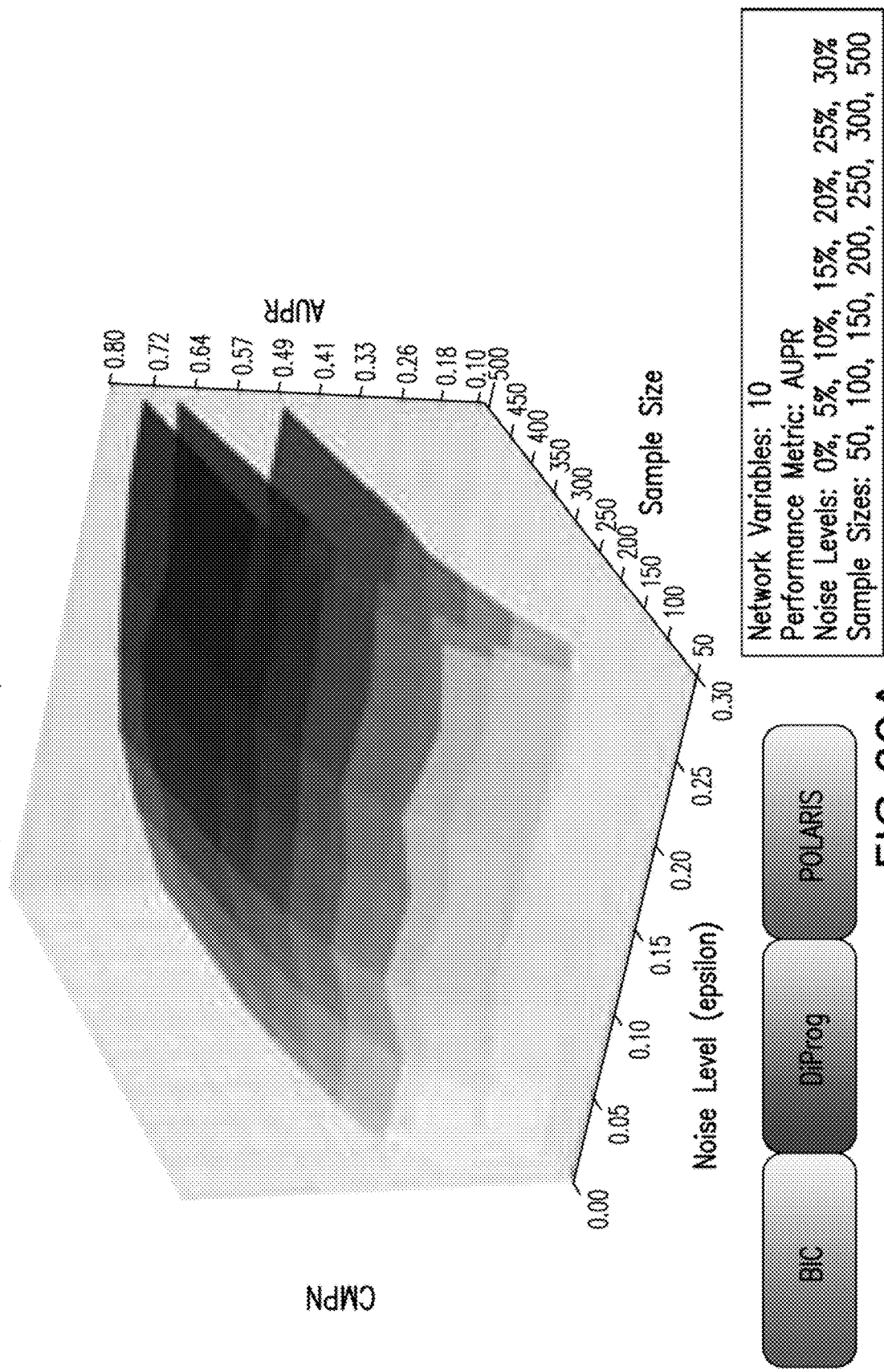
FIGS. 29A-29D are graphs illustrating exemplary tests of the exemplary Polaris procedure according to an exemplary embodiment of the present disclosure.
Figure 29B:
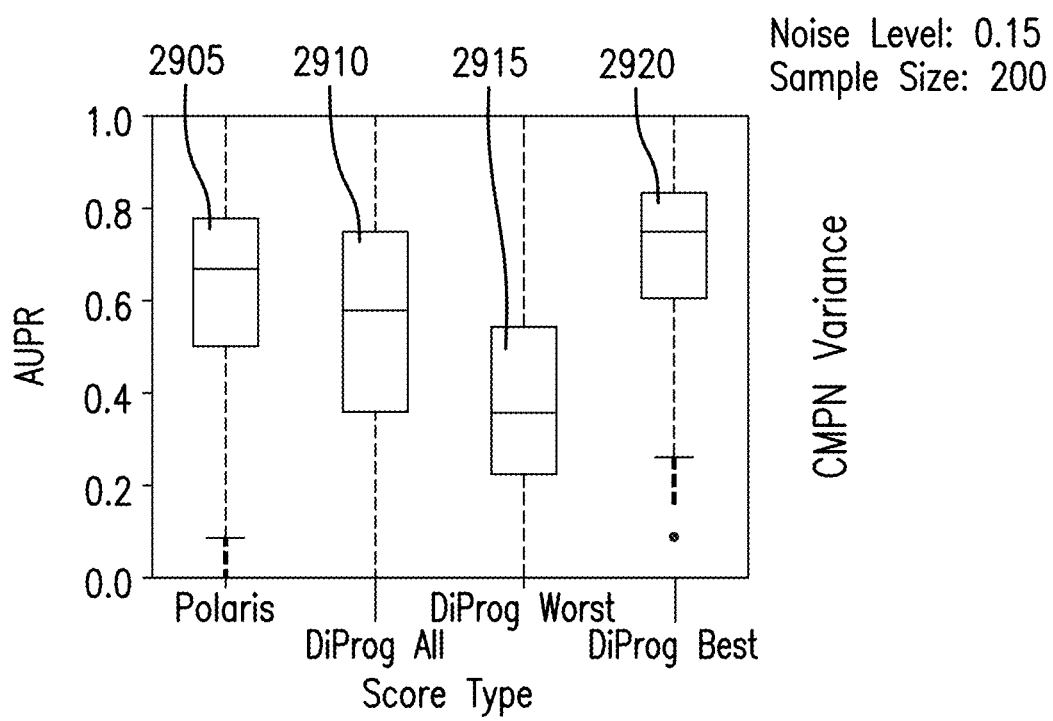
Figure 29C:
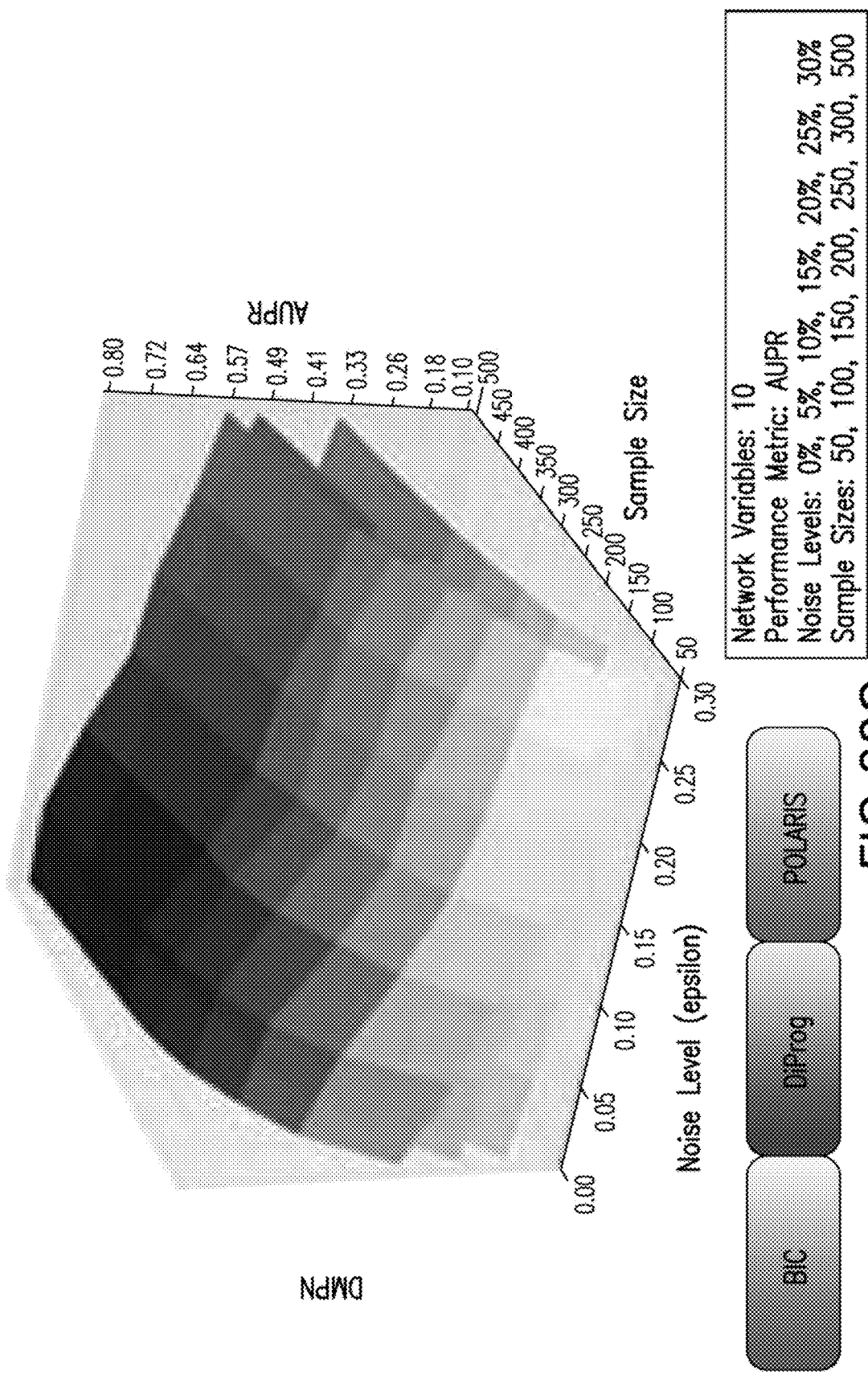

The performance of Polaris was compared against two standards, the optimization of the BIC score and the clairvoyant DiProg procedure, across a variety of biologically and clinically realistic E values and sample sizes. Clairvoyant can mean that the procedure has a priori knowledge of c. To evaluate the performance of each procedure, both the recall, the fraction of true edges recovered, and the precision were measured, and the fraction of recovered edges that can be true. FIGS. 29A-29D illustrate the exemplary results concisely for all three types of MPNs by using AUPR, or the area under the precision-recall curve, as the exemplary performance metric. It was expected that the exemplary Polaris performs significantly better than BIC, which can be nonspecific for monotonic relations and slightly worse than the clairvoyant DiProg algorithms, as Polaris does not have access to the correct value of E. The results showed this exact trend for recall, precision and AUPR. The gap between the clairvoyant DiProg and Polaris remained consistent across all parameter values and relatively low, as opposed to the gap between Polaris and BIC optimization The performance of Polaris against a non-clairvoyant DiProg can be considered by passing DiProg one of about fifty randomly sampled values of E. Because of the cost of running DiProg fifty times, the exemplary model can be limited to CMPN, E to about 0.15, and sample size to about 200. The box plot in FIG. 29B shows the variance of performance for Polaris (e.g., 2905), the average performance of the non-clairvoyant DiProg, the performance of the non-clairvoyant DiProg (e.g., 2910) with the most incorrect value of E (e.g., 2915), and finally, the performance of the clairvoyant DiProg (e.g., 2920). Again using AUPR as the performance metric, it was found that the average performance of the non-clairvoyant DiProg had a significantly lower mean and considerably larger variance than those of the exemplary Polaris. Moreover, the mean of the worst case performance of DiProg was almost twice as low as that of the exemplary Polaris, and the variance was slightly larger. From these analyses, it can be concluded that when E may not be known, more accurate and more consistent results can be expected from the exemplary Polaris than from DiProg.

The description below demonstrates the efficacy and accuracy of the α-filter for CMPNs, DMPNs, and XMPNs. On average, the filter can eliminate approximately half of all possible hypotheses and makes considerably less than one mistake per network. In fact, for sufficiently large sample sizes, the false negative rate can drop to almost zero.

Exemplary Biological Example

The use of the exemplary Polaris on prostate cancer ("PCA") data can be demonstrated. From the experimental observations, an exemplary progression model with 3 distinct sub-progressions can be posited. (See e.g., References 81, 82, 88, 90, 97, 99 and 101). To test this theory, a CMPN was learned based on the copy number alteration ("CAN"), mutation, and fusion event data on the genes discussed above. The TCGA prostate adenocarcinoma dataset of 246 sequenced tumors, available through MSKCC's cBioPortal interface, was used. (See e.g., References 84, 87 and 94).

Figure 30:
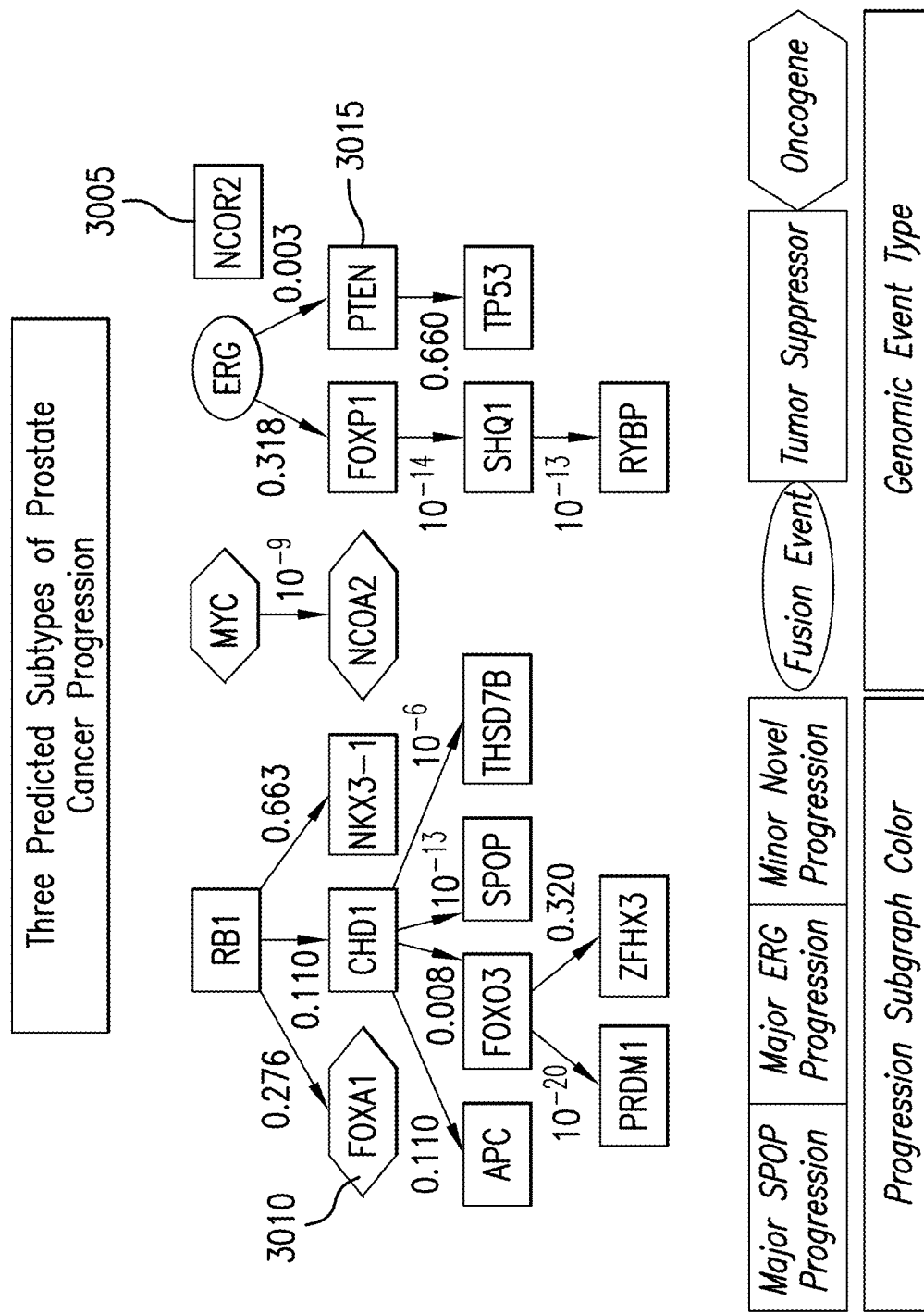
FIG. 30 is a diagram of an exemplary Polaris mode according to an exemplary embodiment of the present disclosure.

It was found that the exemplary learned model, shown in FIG. 30, validates and unifies the observations above in one tri-progression model. First, it was found that two major progressions, one centered on TMPRSS2-ERG fusion (e.g., below referred to as just "ERG") and another around CHD1 and SPOP. This confirms the theory of two distinct progressions defined by SPOP and ERG. (See e.g., Reference 82). Moreover, the exemplary model captures the associated genes predicted in each progression. Namely, CHD1, FOXO3 and PRDM1 can be involved in the SPOP progression and PTEN and TP53 in the ERG progression. Next, it was postulated that MYC, NCOA2 and NCOR2 can be all involved in a third progression, even though NCOR2 appears isolated from the other two in the graph. This decision can be justified by noting previously-known observations. (See e.g., Reference 88, 90 and 99), where it was predicted that there can be a third progression that includes neither CHD1 nor ERG. It has also been predicted that there can be a subtype with poor prognosis that involves the amplification of MYC and NCOA2. It was also predicted that early onset PCA involves the Androgen receptor ("AR") pathway and NCOR2 mutation but does not include ERG, CHD1, or PTEN. Other work has shown an experimental connection between MYC and AR expression, strengthening the MYC/NCOA2 involvement in the third path-way. Lastly, FIG. 30 shows several key driver genes (e.g., NKX3-1, APC, ZFH3, THSD7B, FOXP1, SHQL, RB, RYBP) in the progression of PCA that have not been assigned to either the SPOP or ERG progressions. The model proposes an assignment of these genes to their respective progressions that can be experimentally tested. It can be noted that FOXP1, SHQ1 and RYBP, all genes in the 3p14 region, can be closely related in the progression.

Further Exemplary Discussion

The exemplary Polaris accomplishes its intended tasks effectively and efficiently. To quantify its efficacy, a theoretical analysis is provided below, containing a proof of its asymptotic convergence under some mild conditions. Moreover, the exemplary procedure was empirically tested on a variety of noise levels and sample sizes. It was found that it outperforms the standard score for structure learning and closely trails behind the clairvoyant one. It can be the case, however, that the exemplary Polaris, by virtue of its machine learning abilities, can solely and completely solve all the underlying problems in cancer systems biology.

FIGS. 28A-28D illustrate an exemplary procedure according to an exemplary embodiment of the present disclosure. The Polaris exemplary procedure accepts raw cross sectional genomic data and computes a causal progression model with logical relations among the variables. Initially (e.g., FIG. 28A), each patient's tumor can be sampled during surgery and sequenced afterwards. From the sequencing, it can be found that each tumor has genomic aberrations in certain genes and not others. Most genes will be common among the tumors, although some may be outliers (e.g., gene 2805). This data can then be projected into a high dimensional space (FIG. 28B) and the genes' co-occurrence frequencies can be encoded as a joint distribution over the gene variables. The exemplary Polaris can mine this data for causal relations (FIG. 28C) and can encode the major causal progressions among the genes in a graphical model. The minor causes 2810 can account for the outliers in the data and often reflect a varying spectrum in cancer types among the patients. These minor causes 2810 can be averaged and collapsed into a causal or biological noise parameter in the model. Finally, many genomic events, for instance CDK 2815 mutation, seem to precipitate from the occurrence two or more events, for instance EGFR 2820 and MYC 2825 mutations. A language for expressing this dependence is shown in FIG. 28D. Using the examples in the FIGS. 28A-28D, CDK 2825 can be facilitated to occur only when both EGFR2820 and MYC 2825 occur CMPN, when either one occurs DMPN, or when only one but not both occur XMPN. The examples of conditional probability distributions CPDs reflect these logical relations.

As shown in exemplary graphs of FIGS. 29A-29D, the performance of the exemplary Polaris was tested against the optimization of a standard symmetric score, BIC and a clairvoyant procedure for learning MPNs, DiProg. Each procedure was tested across several different levels of noise (e.g. about 0% to about 30%) and across several realistic number of training samples (e.g. about 50 to about 500). In each case, the network contained ten variables, common for progression models, although each procedure can handle a great deal more.

Figure 29D:
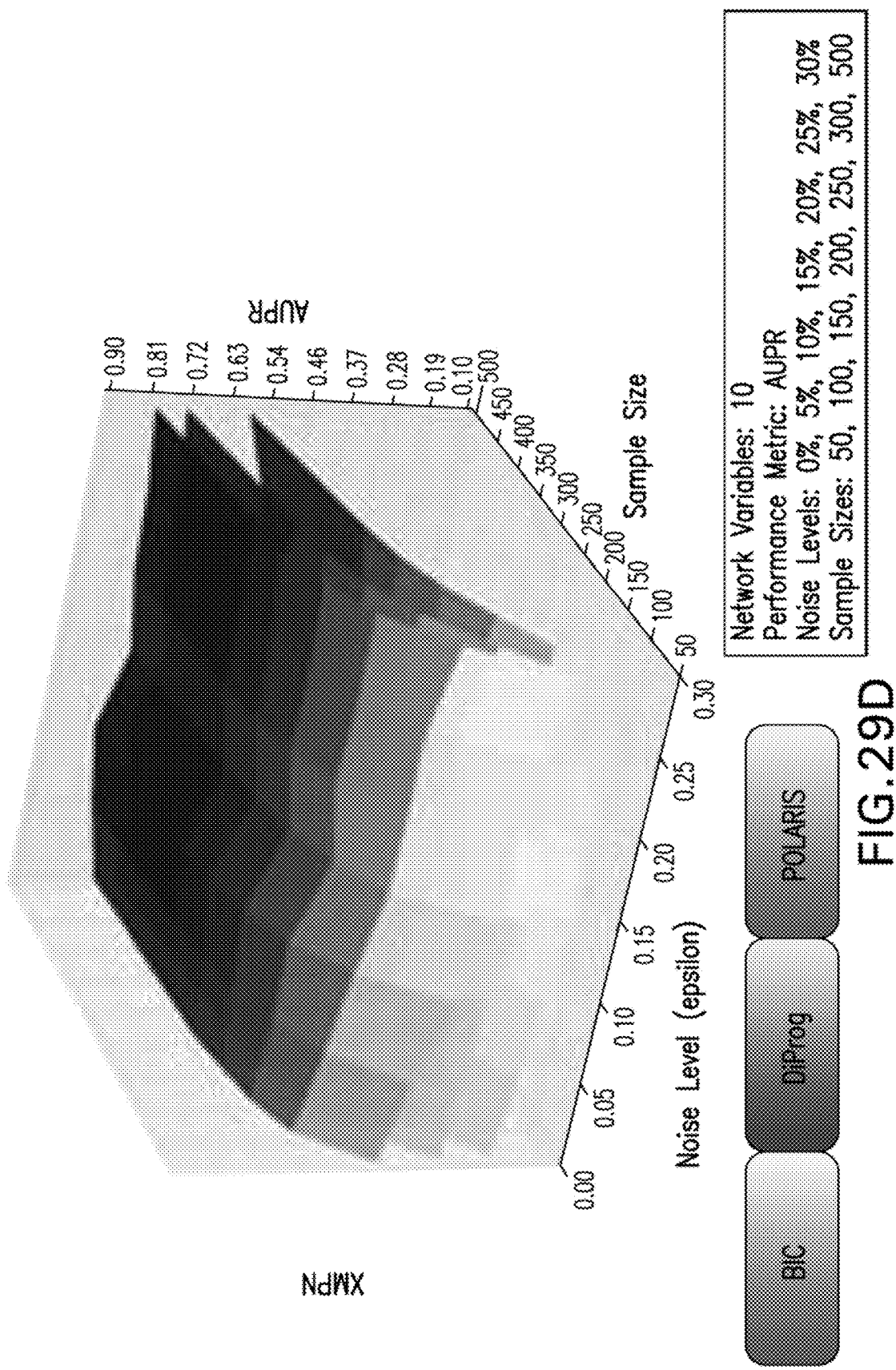

The exemplary surface plots (e.g., FIGS. 29A, 29C and 29D) show the performance of each procedure for different MPN types, CMPN (e.g., FIG. 29A), DMPN (e.g., FIG. 29C) and XMPN (e.g., FIG. 29D). The box plots on the top right demonstrate the dependence of DiProg performance on a priori knowledge of E. A network with ten variables was learned (e.g., about 15% noise and about 200 samples with Polaris, DiProg with the correct E, and DiProg with a random E). Element 2910 shows the average performance across the random E values. Element 2915 shows the worst performance with a random E value. Element 2920 shows the performance with knowledge of the correct E value. For all four plots, the rate of both true positives (e.g. recall) and true negatives (e.g. precision) can be measured by computing the area under the precision-recall curve, or the AUPR.

As shown in FIG. 30, the exemplary Polaris model was used to learn a CMPN model for prostate cancer. The most commonly implicated oncogenes, tumor suppressor genes, and gene fusion events were selected from the literature and used copy number variation and point mutation data from the TCGA database. Each edge is labeled with the fold change in the network score when the edge is left out. Based on the topology and the exemplary literature survey, three distinct progressions within the graph can be defined, and each is labeled 3005, 3010 and/or 3015.

Exemplary Detailed Comparison of Performance Results on Synthetic Data

Here, the performance results for the comparison of Polaris to the optimization BIC and the clairvoyant DiProg can be included. FIGS. 28A-30 show the comparison results using recall and precision as performance metrics and both small and asymptotic sample sizes, for CMPNs, DMPNs and XMPNs, respectively. The recall and precision can be separated in order to highlight the asymmetry in Polaris's performance. That can be, the exemplary Polaris performs considerably better in recall and consistently introduces a slightly higher number of false edges in the reconstructed graph. The asymptotic sample size can be included to experimentally verify the convergence of Polaris. Note that theorem 6 only guaranteed convergence on graphs without transitive edges, but even with transitive edges, the exemplary Polaris can converge almost completely at only about 2000 samples.

Figure 31A:
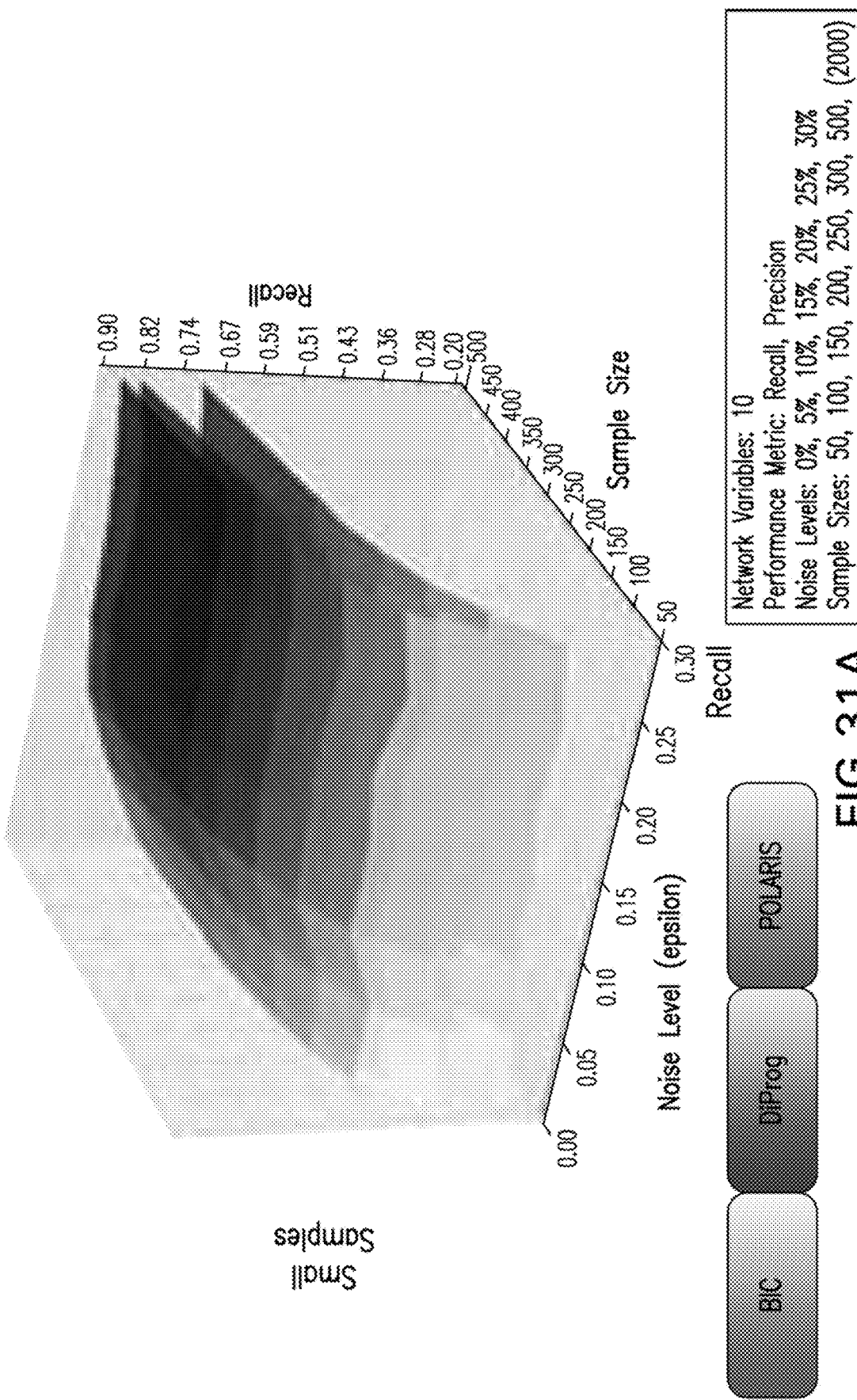
FIGS. 31A-31D are graphs illustrating exemplary performance results for Polaris, BIC, and clairvoyant DiProg on CMPNs.
Figure 31B:
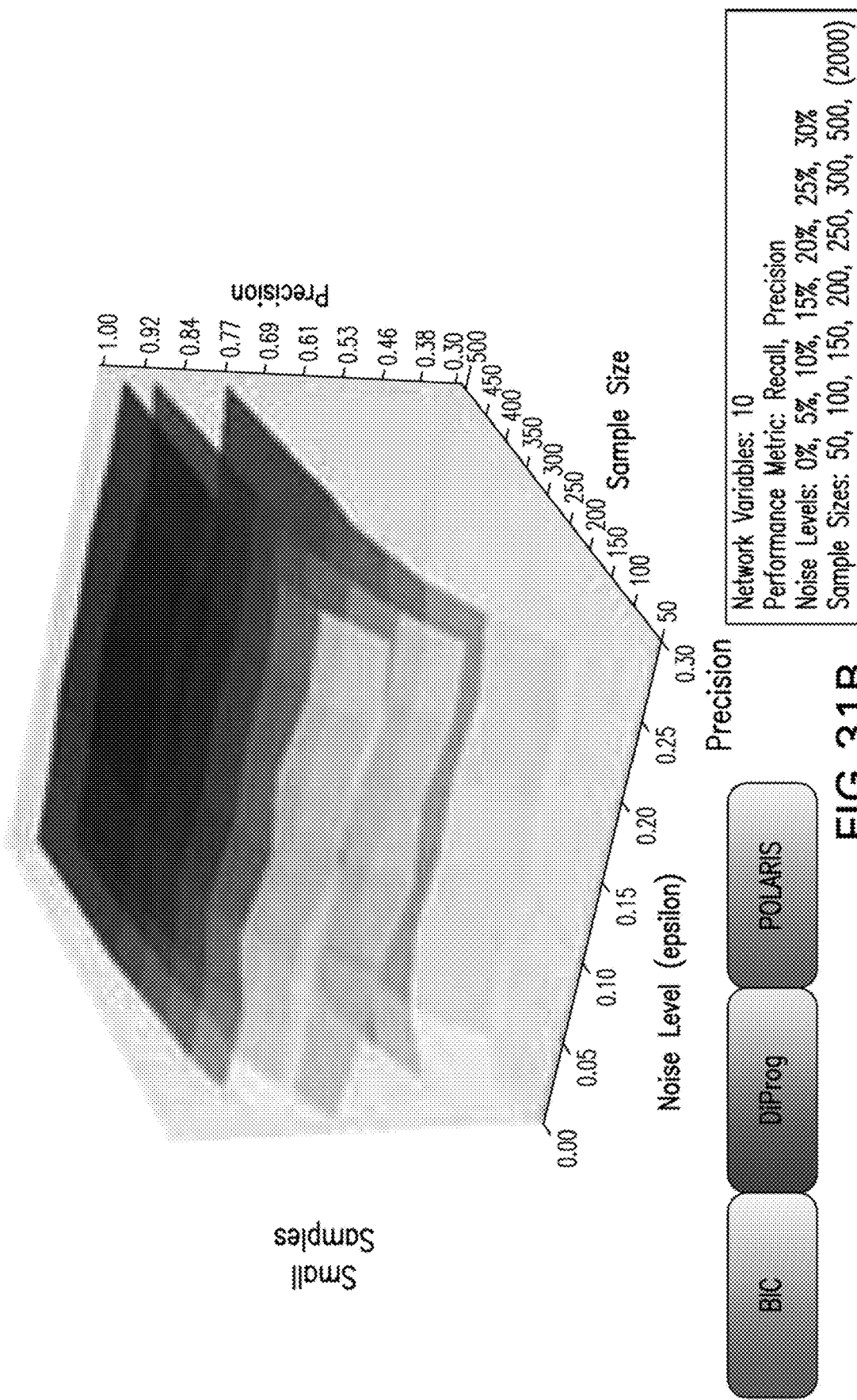
Figure 31C:
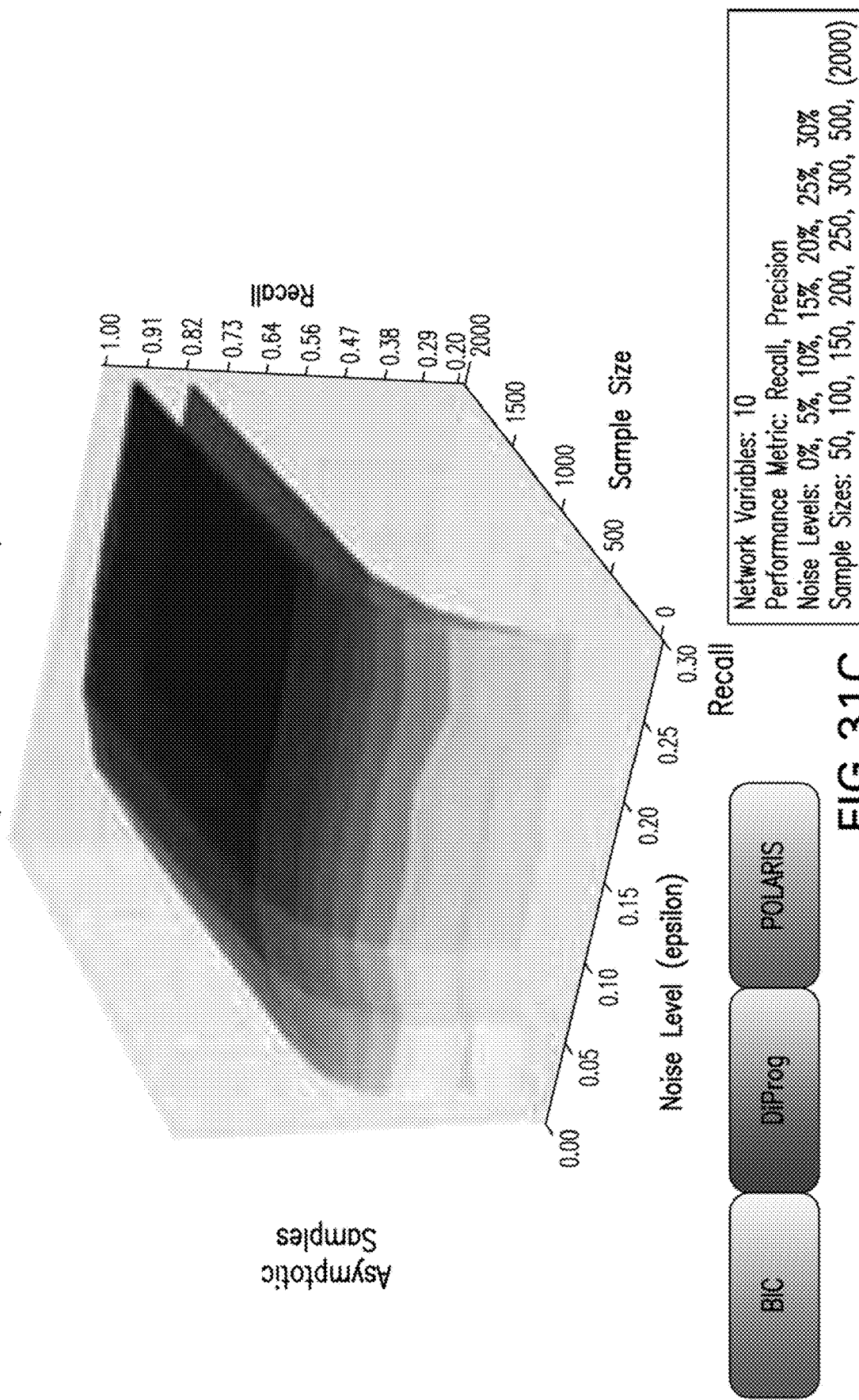
Figure 31D:
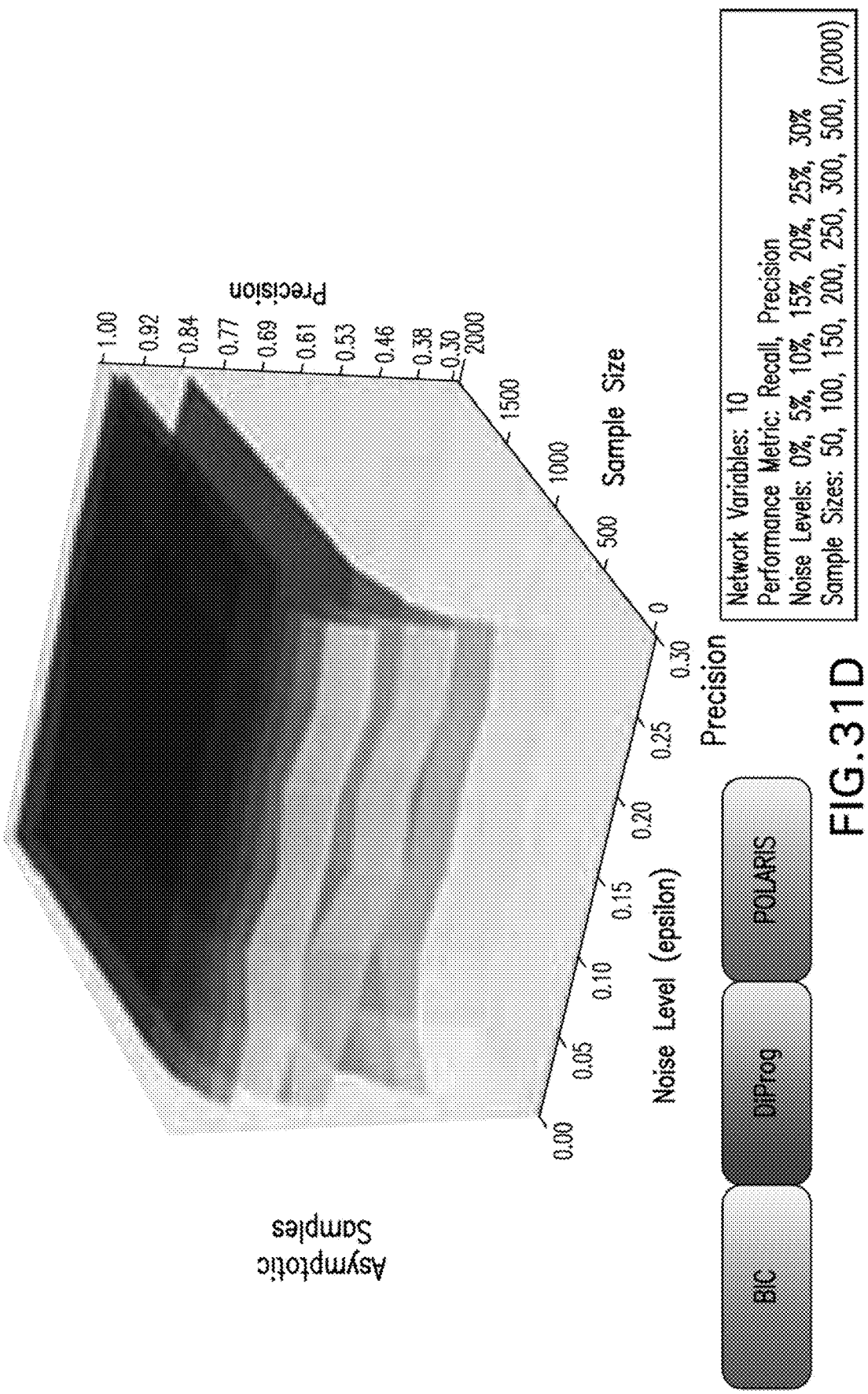

FIGS. 31A-31D illustrate exemplary graphs providing experimental performance results for Polaris, BIC, and clairvoyant DiProg on CMPNs, measured in terms of recall (e.g., FIGS. 31A and 31C) and precision (e.g., FIGS. 31B and 31D). To show the asymptotic behavior of the three algorithms, the performance can be plotted for sample sizes up to about 2000 (FIGS. 31C and 31D). For comparison, the performance on more realistic sample sizes was included (FIGS. 31A and 31B).

Figure 32A:
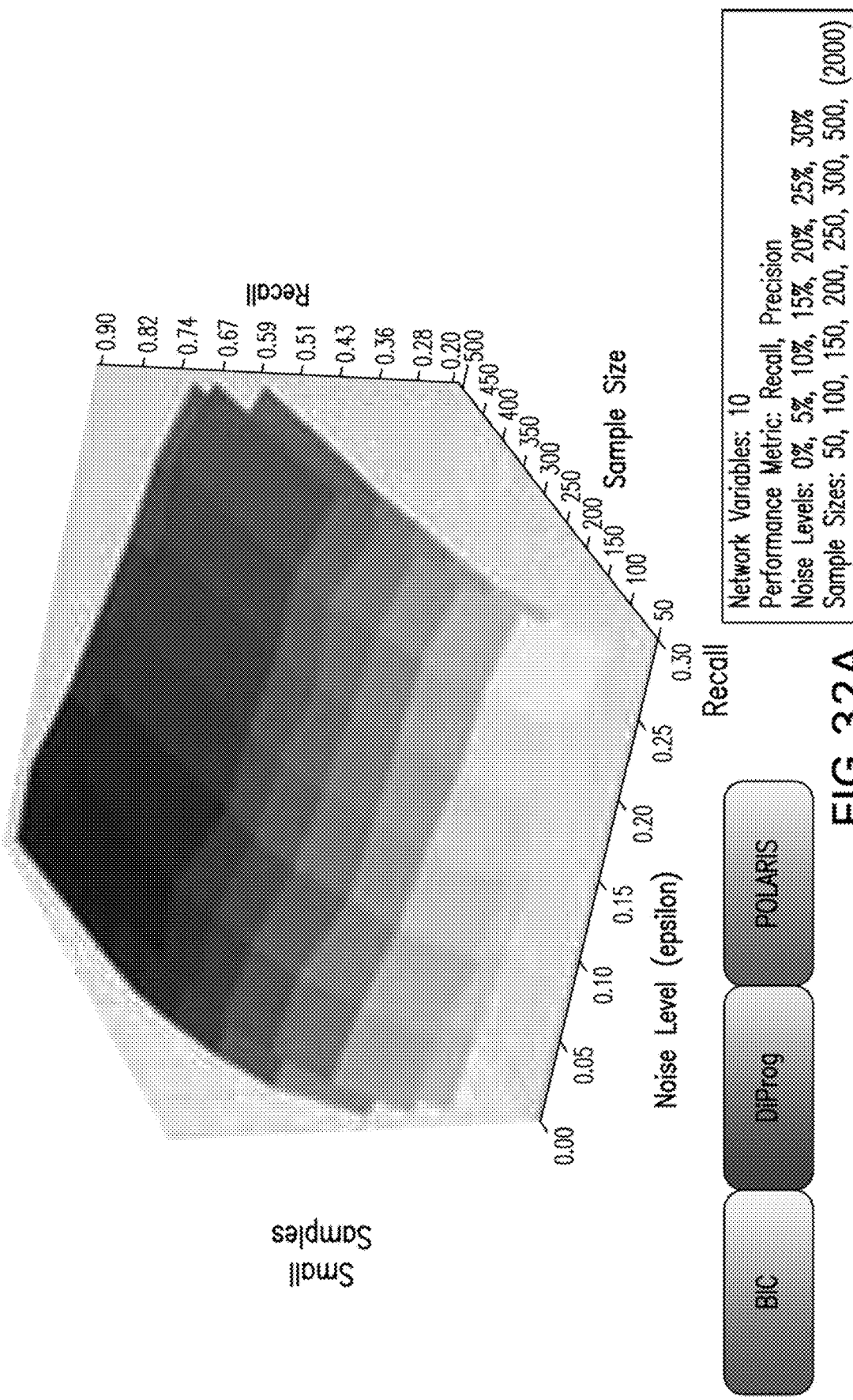
FIGS. 32A-32D are exemplary graphs illustrating further exemplary performance results for Polaris, BIC, and clairvoyant DiProg on DMPNs.
Figure 32B:
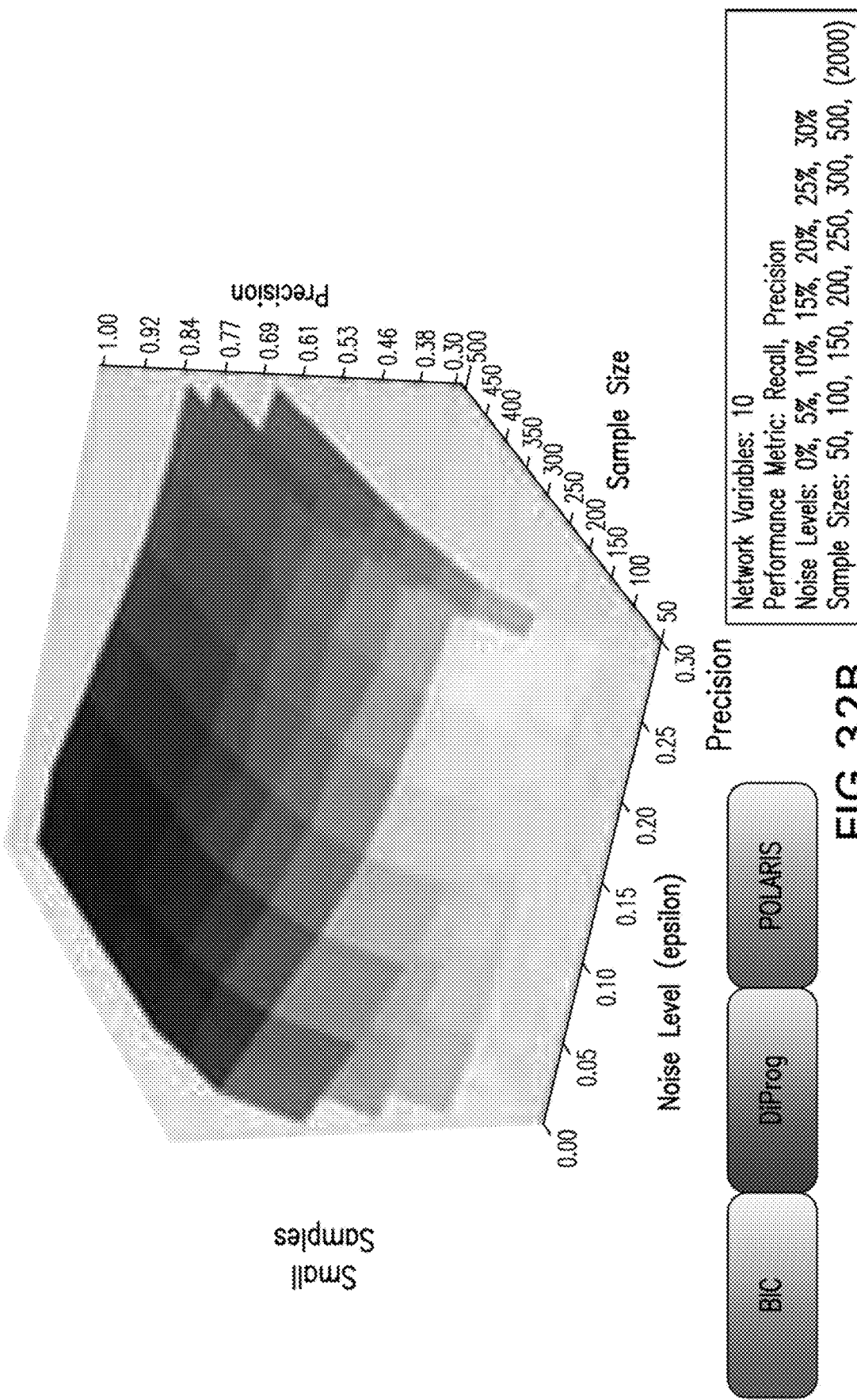
Figure 32C:
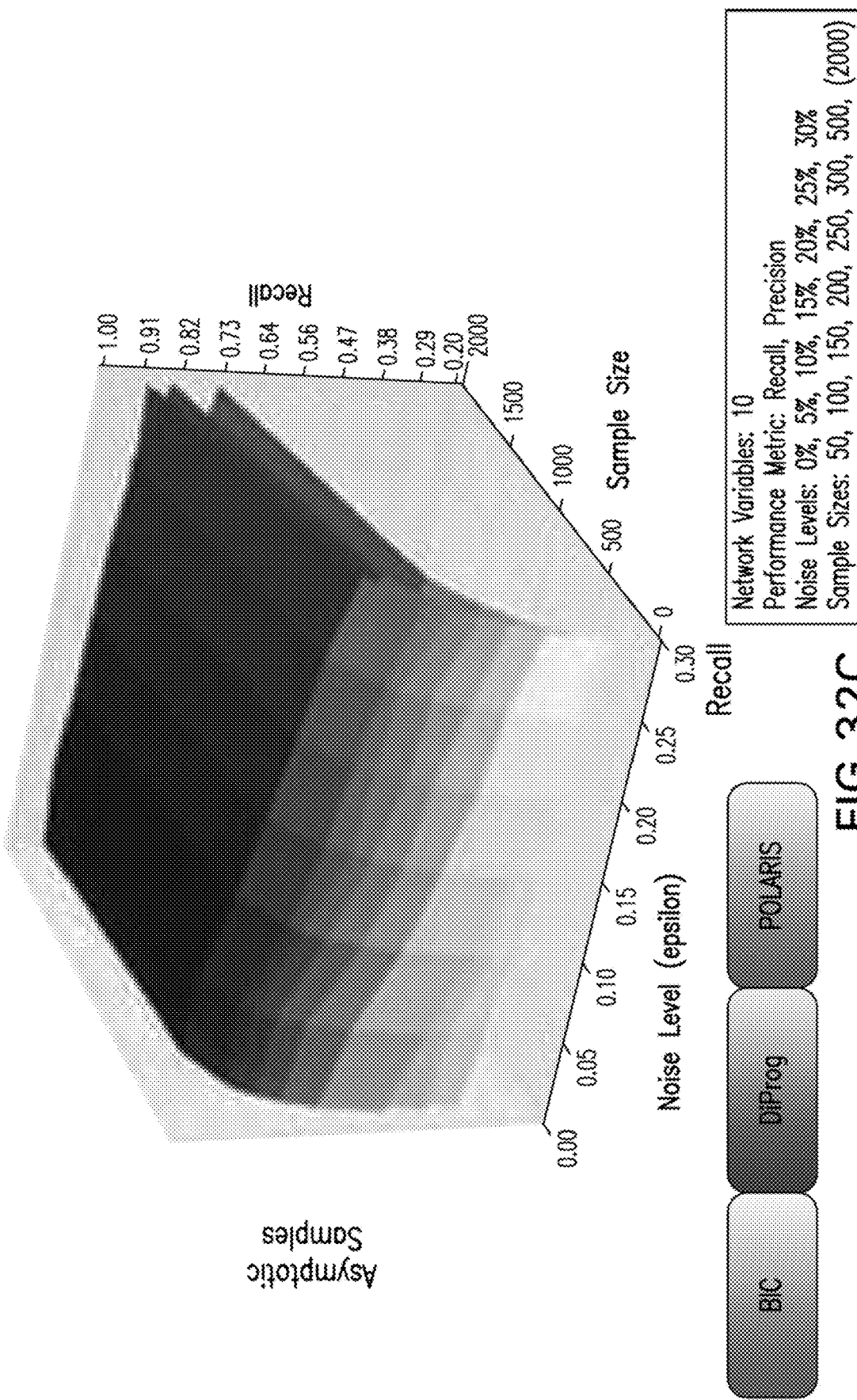
Figure 32D:
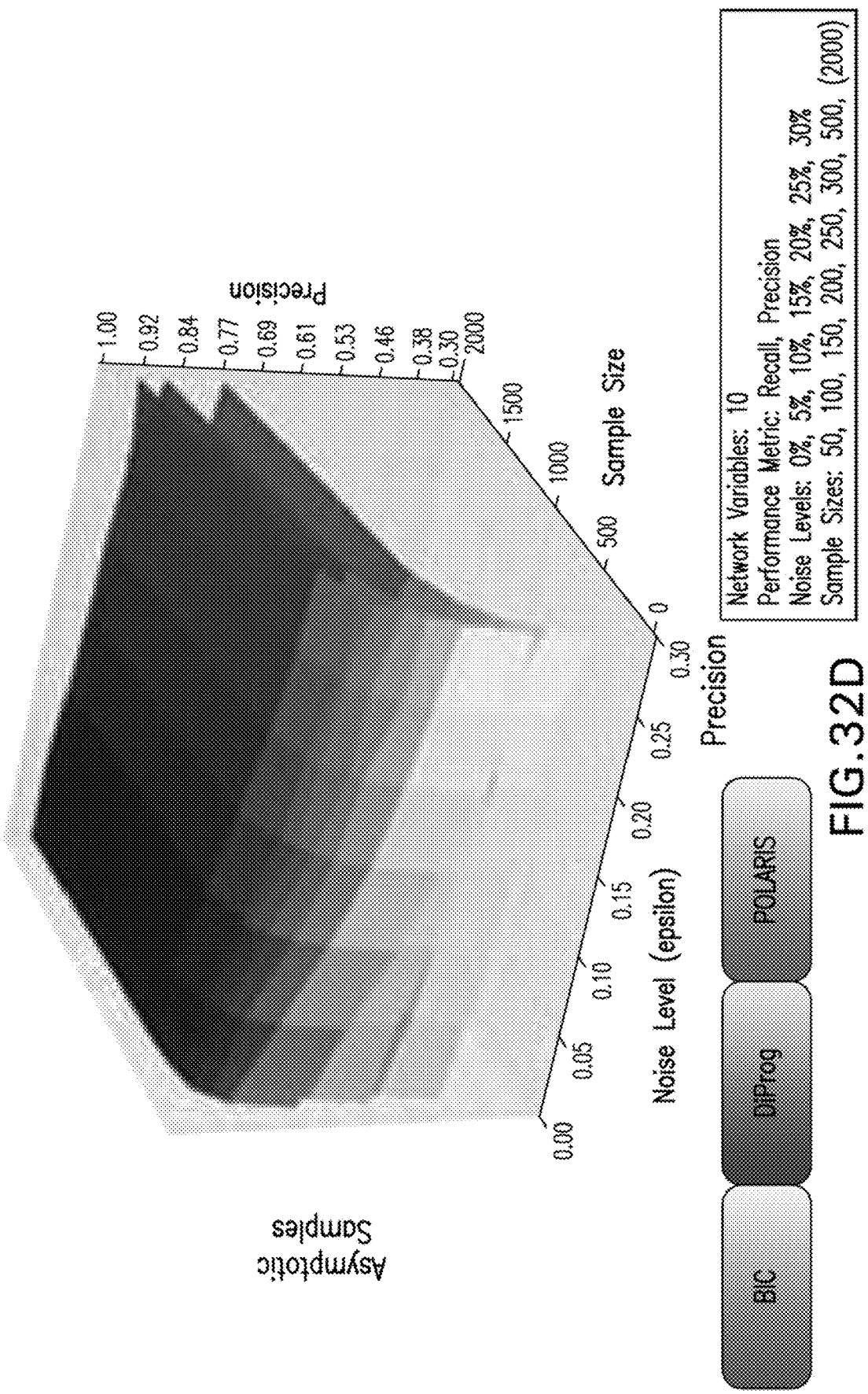

FIGS. 32A-32D show exemplary graphs providing experimental performance results for the Polaris, BIC, and clairvoyant DiProg on DMPNs, measured in terms of recall (FIGS. 32A and 32C) and precision (FIGS. 32B and 32D). To show the asymptotic behavior of the three algorithms, the performance for sample sizes up to about 2000 (FIGS. 32C and 32D) were plotted. For comparison, the performance on more realistic sample sizes was included (FIGS. 32A and 32B).

Figure 33A:
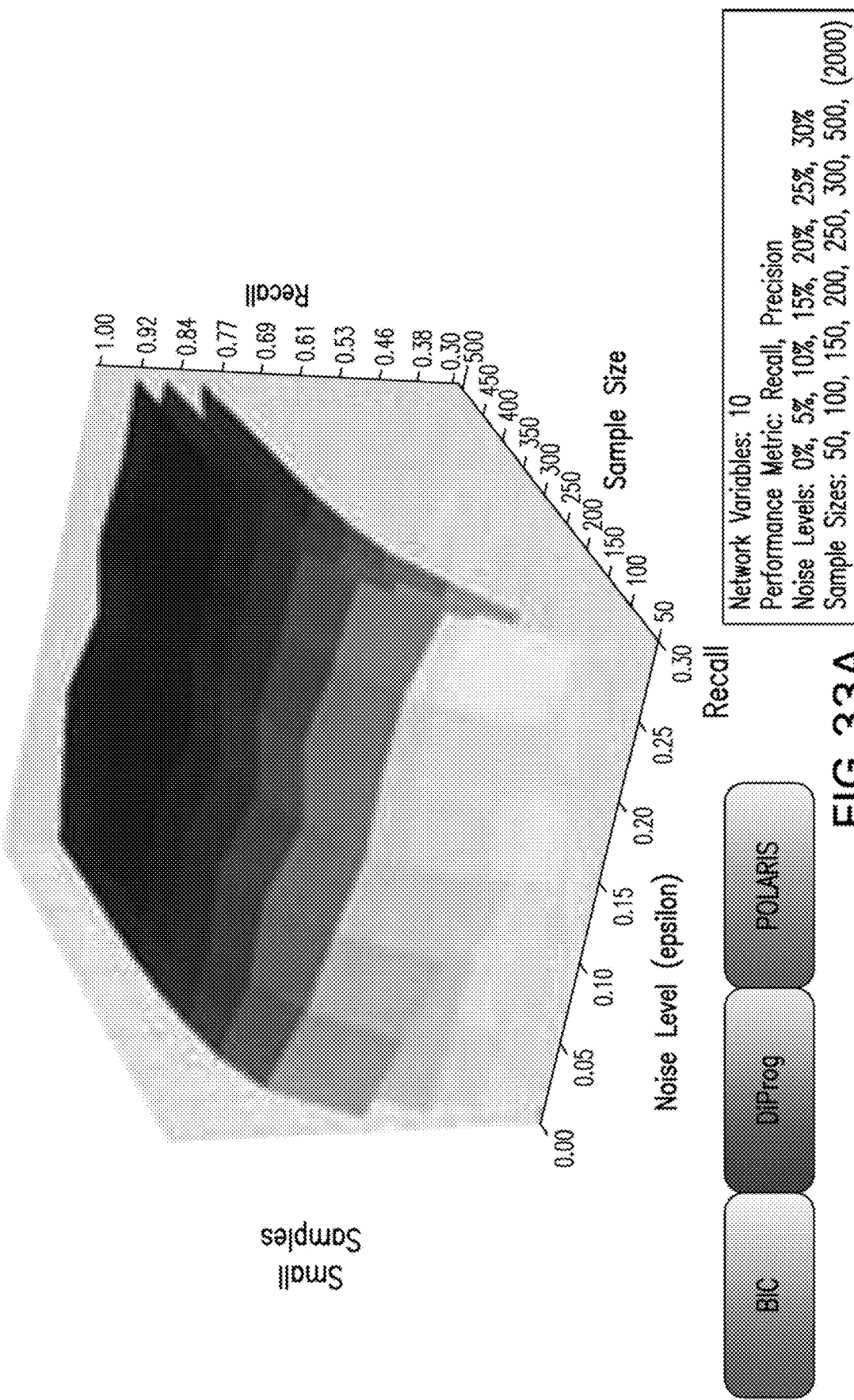
FIGS. 33A-33D are exemplary graphs illustrating yet further exemplary experimental performance results for Polaris, BIC, clairvoyant DiProg on XMPNs.
Figure 33B:
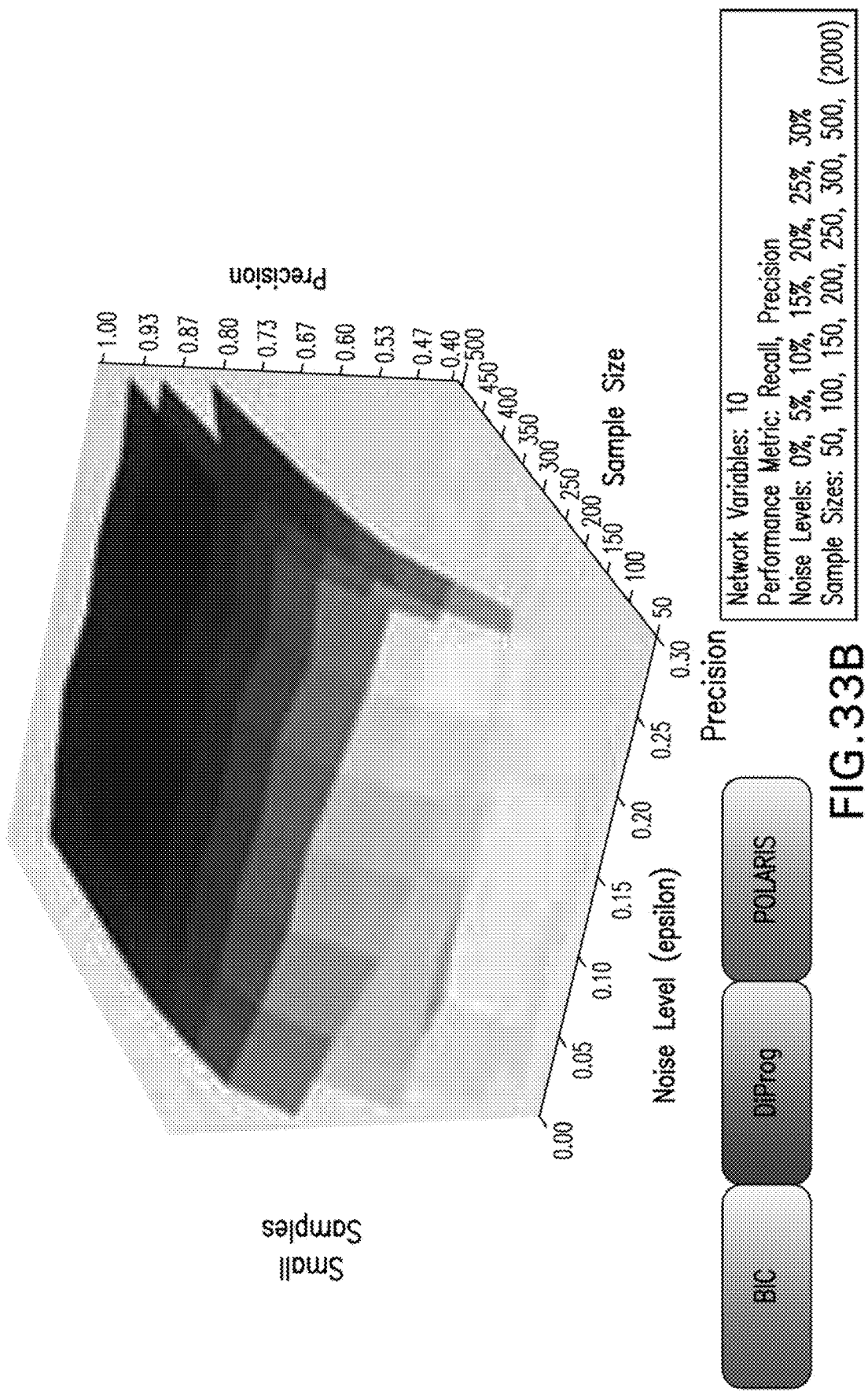
Figure 33C:
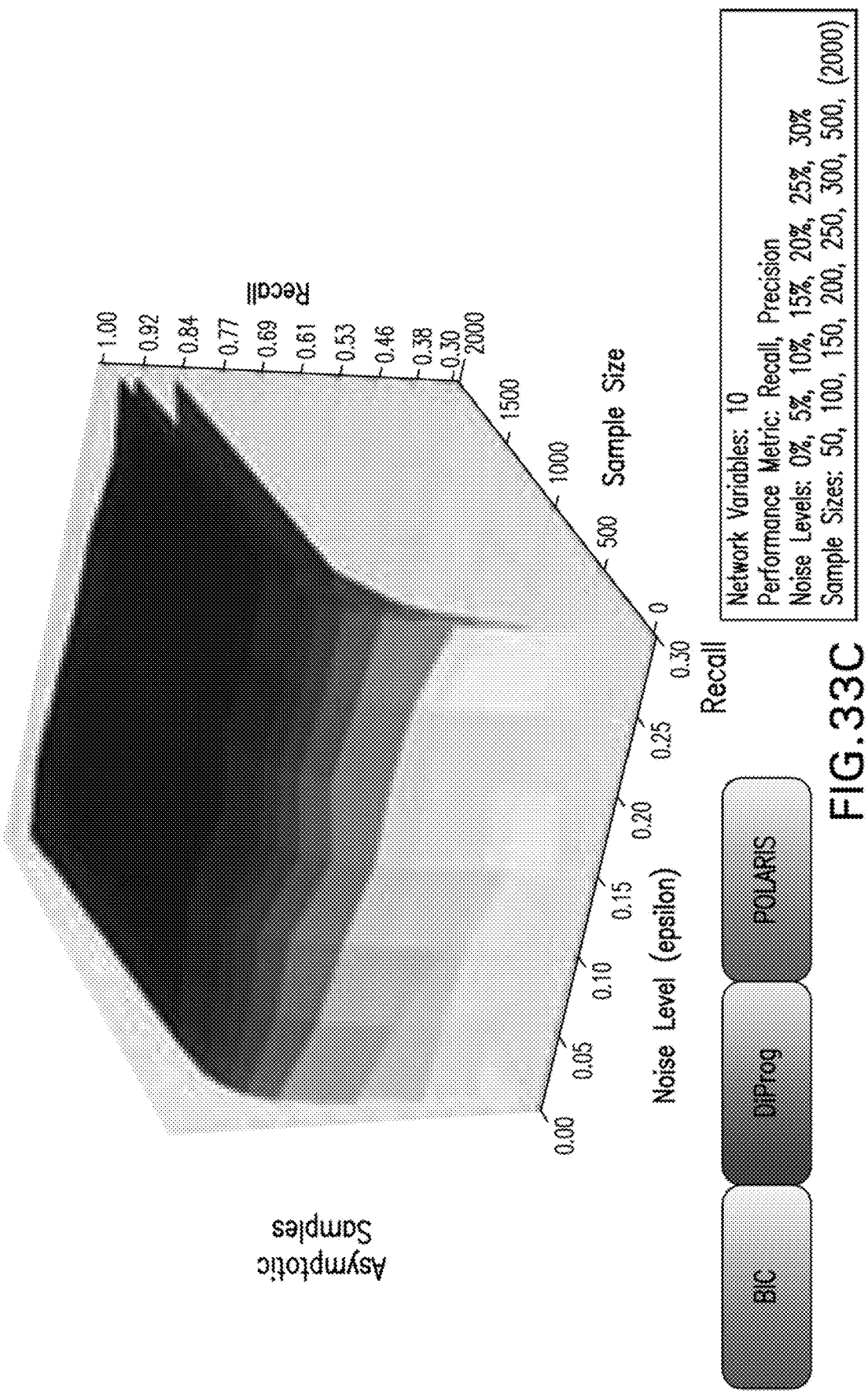
Figure 33D:
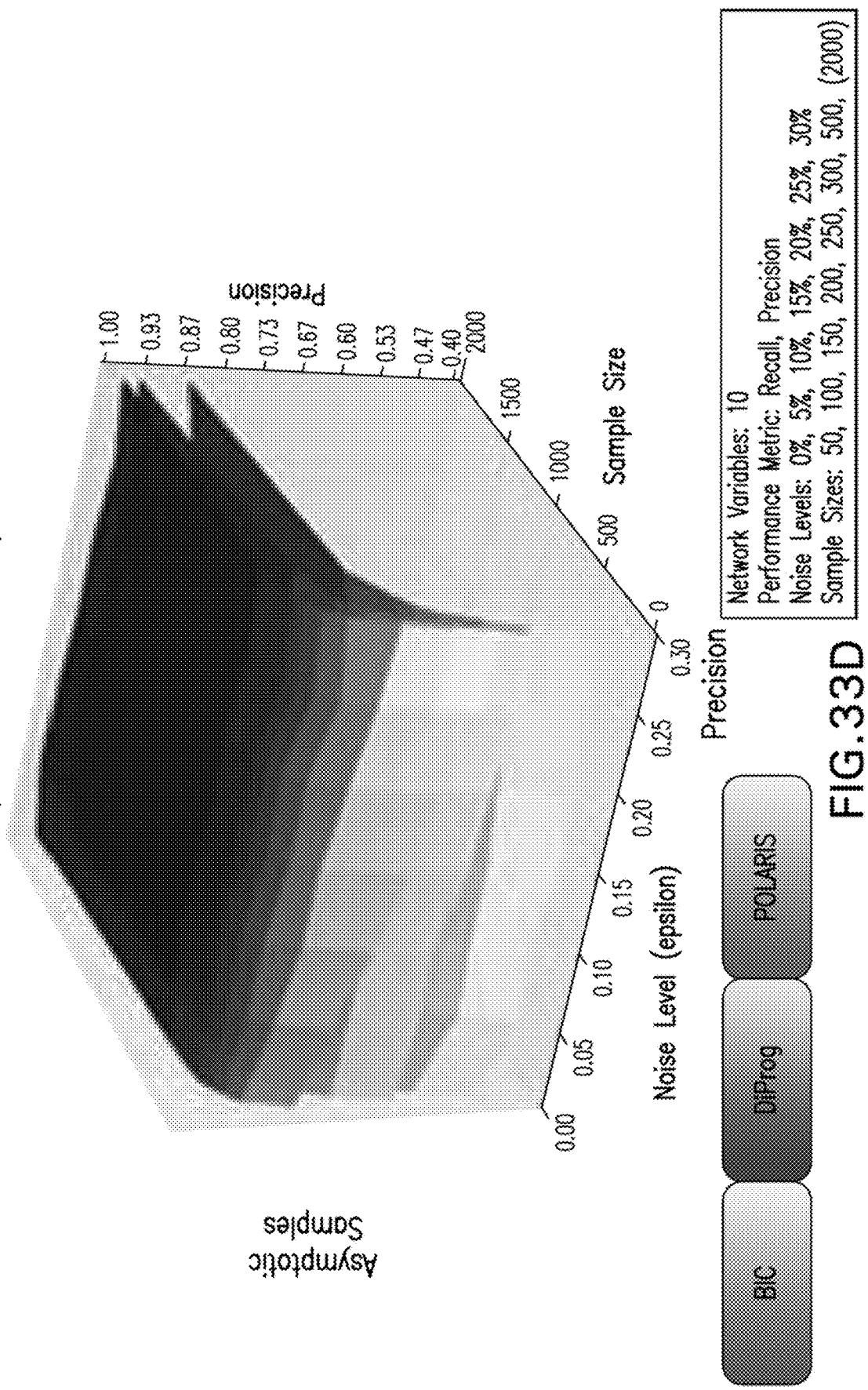

FIGS. 33A-33D illustrate exemplary graphs providing experimental performance results for Polaris, BIC, and clairvoyant DiProg on XMPNs, measured in terms of recall (FIGS. 33A and 33C) and precision (FIGS. 33B and 33D). To show the asymptotic behavior of the three algorithms, the performance for sample sizes up to about 2000 was plotted. (See FIGS. 33C and 33D). For comparison, the performances on more realistic sample sizes were included. (See FIGS. 33A and 33B). FIGS. 33A-33D demonstrates the efficacy and correctness of the α-filter in rejecting hypotheses prior to optimization of the score, in each of the three types of MPNs. For each type of MPN, the average number of rejected true hypotheses can be considerably smaller than one and converges to zero for medium sample sizes. The α-filter can be particularly effective at pruning the hypothesis space of XMPNs, rejecting approximately 1000 hypotheses on average, out of a possible 1300 hypotheses. It can be slightly less effective for CMPNs, rejecting between about 500 and about 1000 hypotheses. Finally, it can be least effective for DMPNs, rejecting between about 150 and about 350 hypotheses.

Figure 34A:
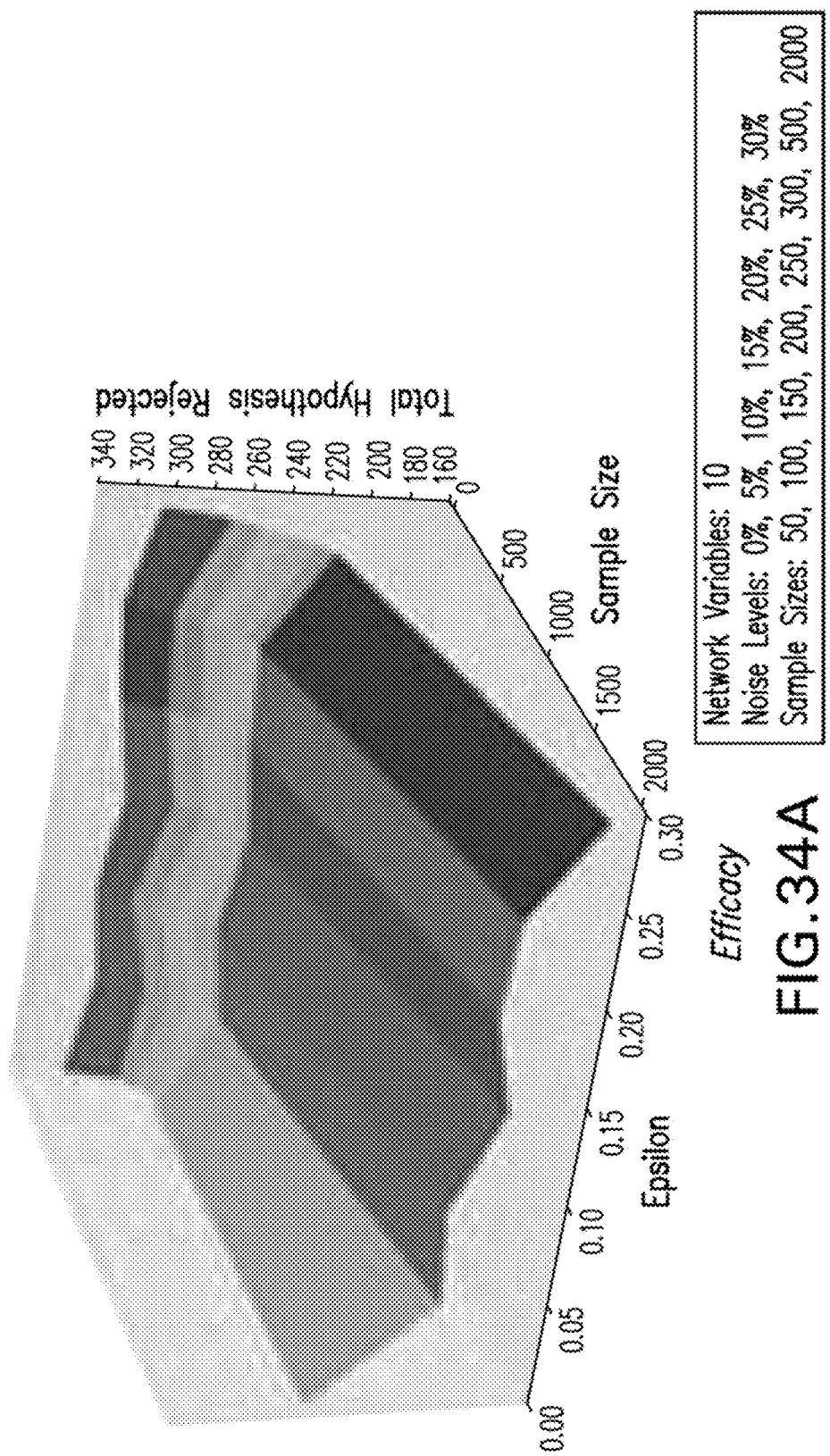
FIGS. 34A-34F are exemplary graphs illustrating an exemplary α-filter rejects hypotheses prior to optimization of the score according to an exemplary embodiment of the present disclosure.
Figure 34B:
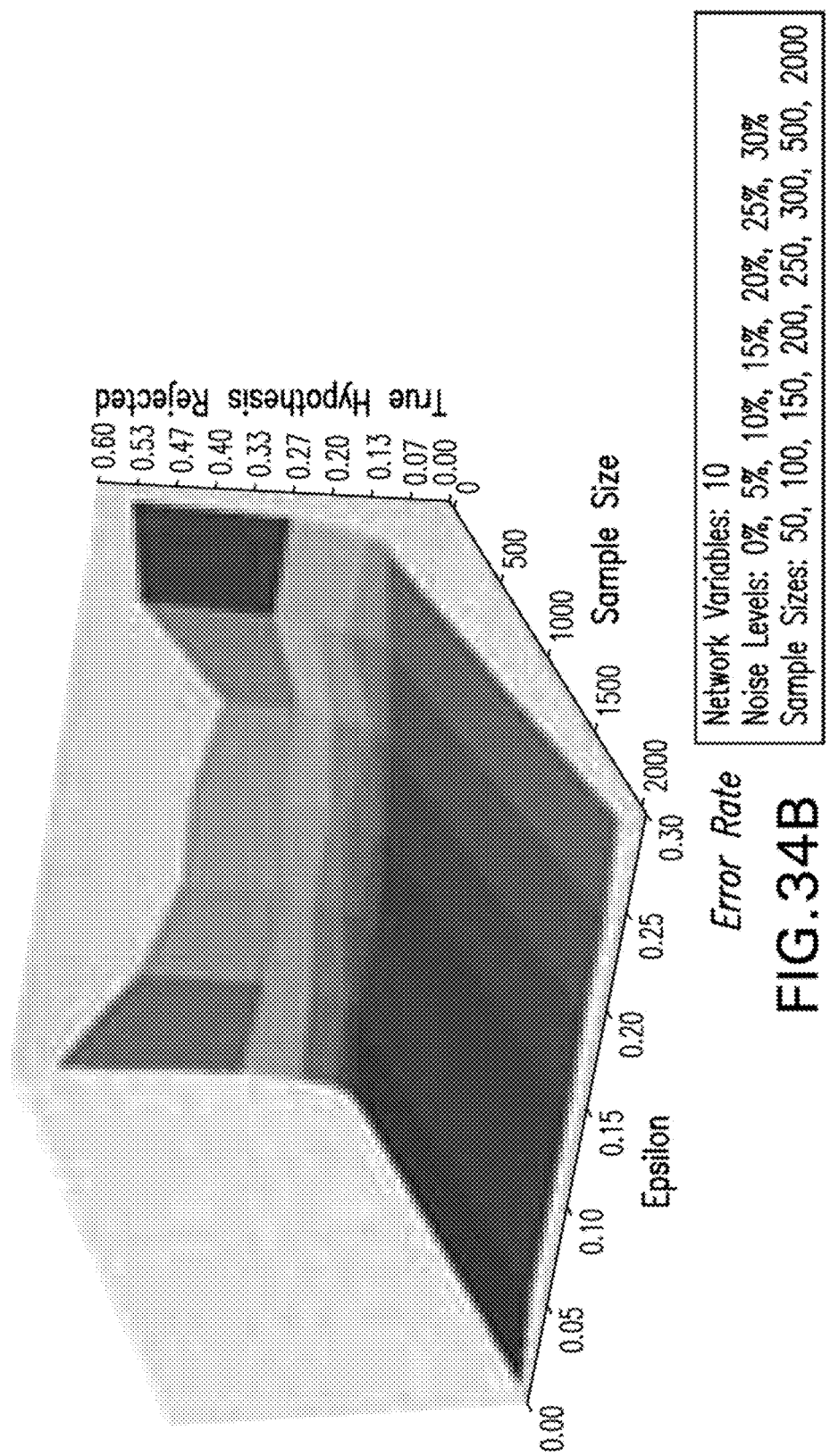
Figure 34C:
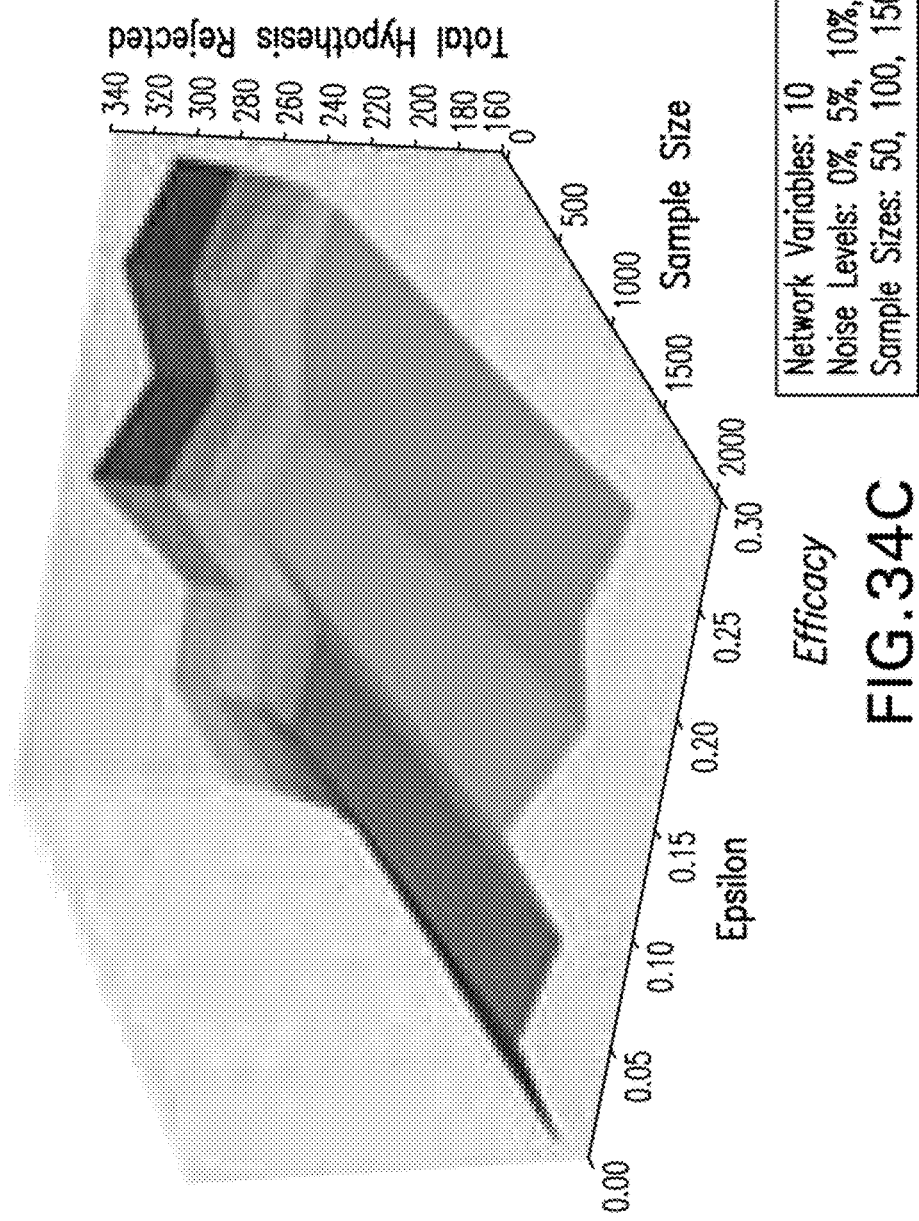
Figure 34D:
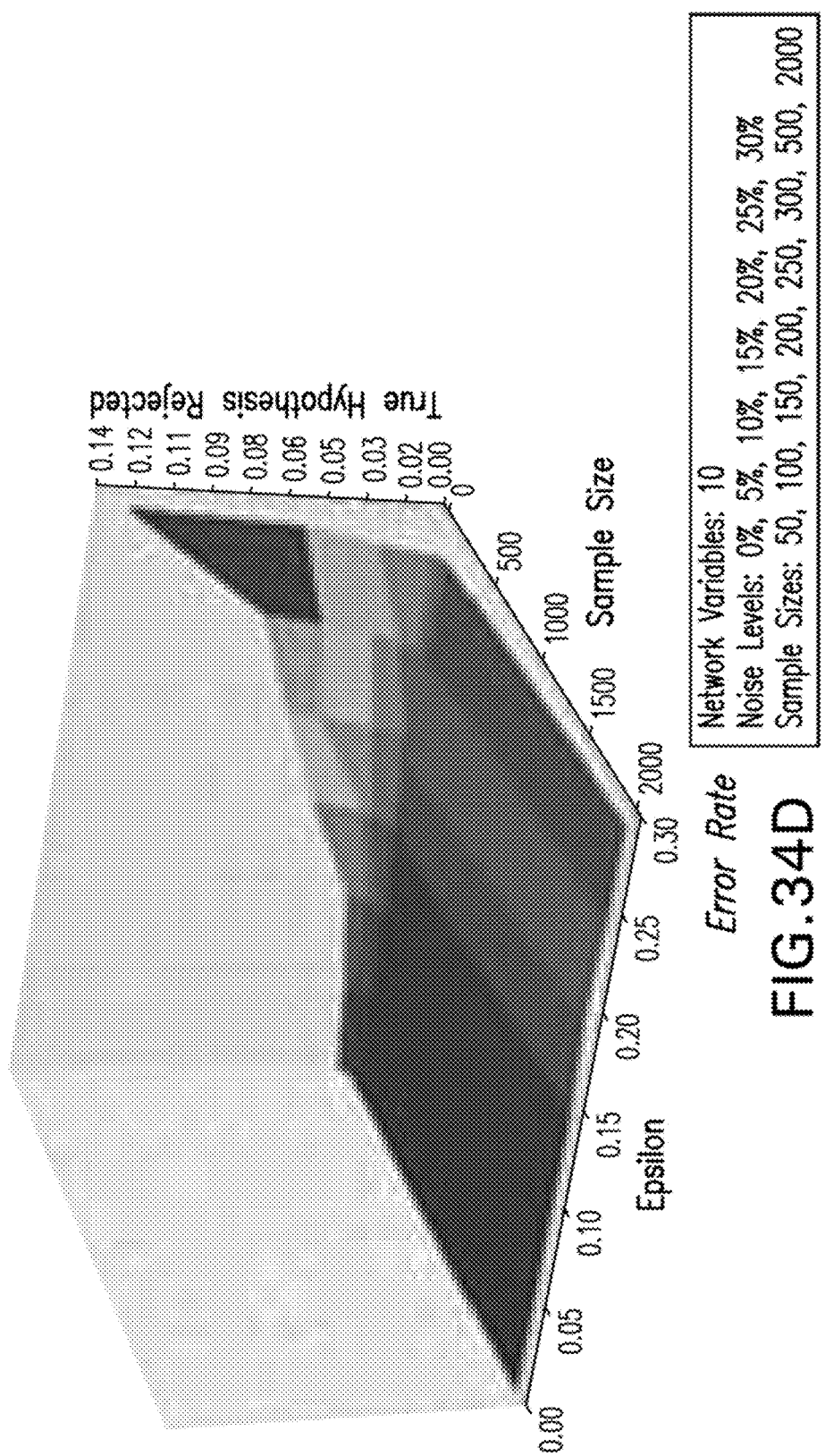
Figure 34E:
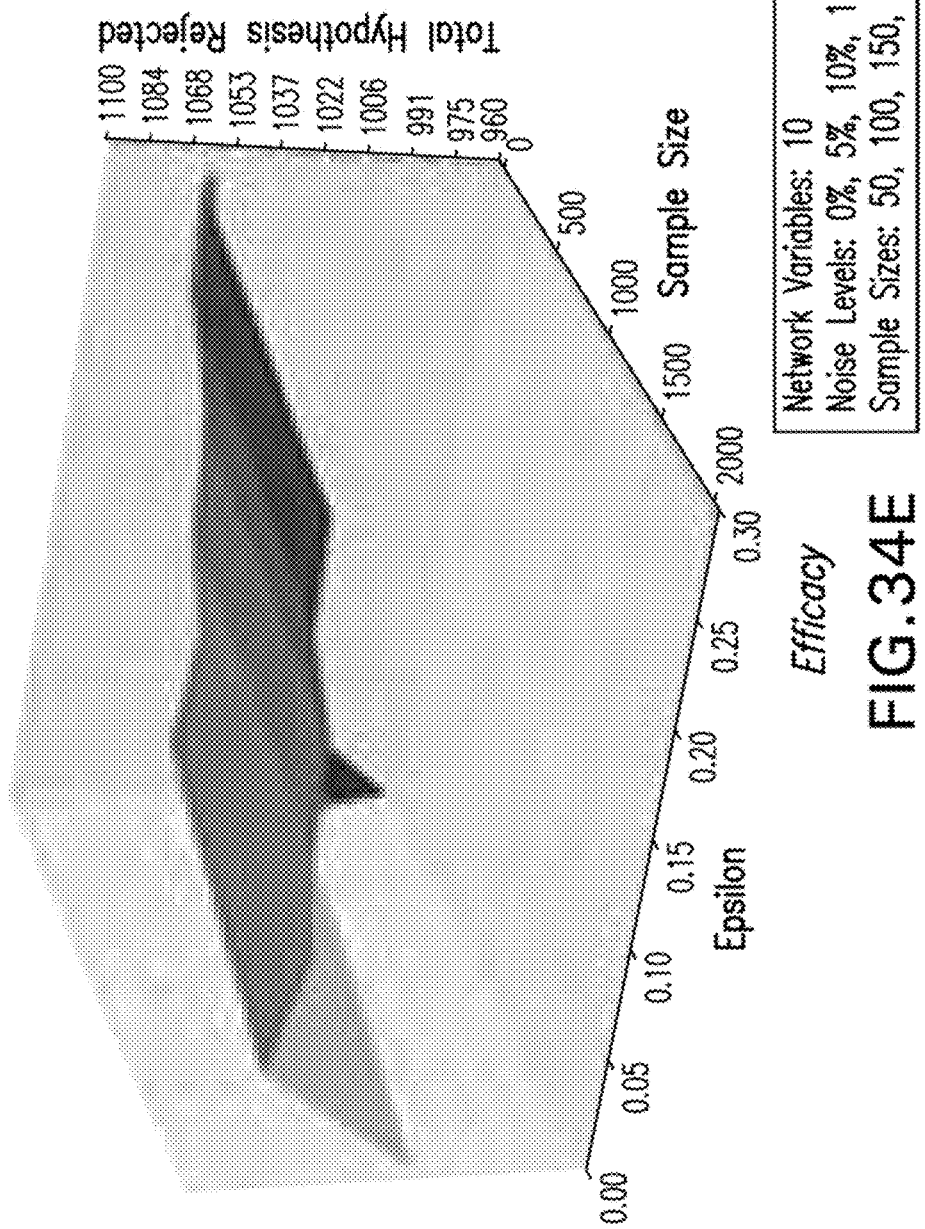
Figure 34F:
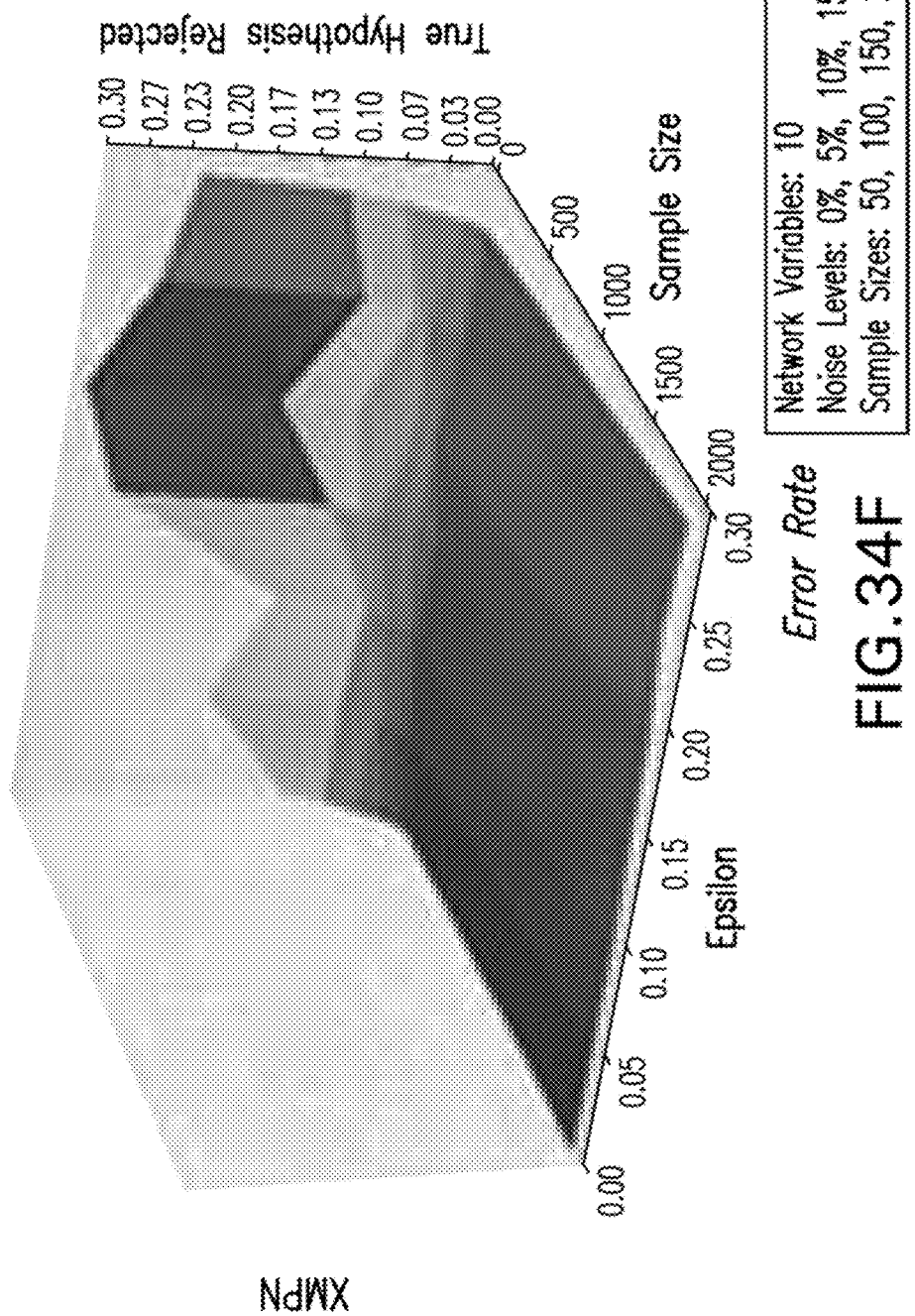

FIGS. 34A-34F illustrate exemplary graphs providing the α-filter rejects hypotheses prior to optimization of the score. FIGS. 34A, 34C and 34F show the efficacy, measured in terms of the number of hypotheses eliminated prior to optimization. FIGS. 34B, 34D, and 34F show the error rate, measured in terms of the average number of true hypotheses rejected.

Exemplary Time Complexity Of Polaris Optimization

The evaluation of the exemplary Polaris scores for all hypotheses can dominate the computational complexity of the exemplary procedure. The asymptotic complexity of this computation can be analyzed, and it can be shown that its parametric complexity can be exponential, where the exponent can be determined by the parameter. For a fixed (e.g., small) value of the parameter, Polaris can be polynomial and tractable. To estimate the complexity, the complexity of computing the score for any single hypothesis can be determined. Then, this function can be multiplied by the number of hypotheses to get the total cost, which can be $O(M \cdot N2 \cdot (N-1)k)$.

Here, the parameter k can be the maximum number of parents for any node (and can be safely bounded by 3, in practice), and the input size can be determined by M and N: respectively, the number of samples, and the number of variables. In practice, the α filter helps performance tremendously, as it avoids the log likelihood ("LL") computation for at least nearly half of the hypotheses. (See e.g., FIGS. 34A-34F).

Exemplary Computing The Score For A Single Hypothesis

A large part of the score computation effort can be expended in computing α and the LL. The α computation can be divided into computing $\theta+$'s and $\theta+$'s, which can be just the probabilities of each row in the matrix, encoding Conditional Probability Distributions, ("CPD"). Both computations can entail counting the number of samples that correspond to each row and thus in total, take $O(M \cdot N)$ time. The maximum likelihood ("ML") parameters in the LL score can be precisely the $\theta+$'s and $\theta-$'s computed for a. Actually computing the LL given the ML parameters can benefit from iterating through the samples one more time and matching each sample to its corresponding CPD row. Thus, LL computation also takes $O(M \cdot N)$ time. Combining all, the total local score computation for one node still takes $O(M \cdot N)$ time.

Exemplary Proofs of Theorems on Asymptotic Convergence

Provided below is a description of exemplary properties about the asymptotic performance of Polaris.

Lemma 2 (Convergence of α-Filter):

For a sufficiently large sample size, M, the α-filter produces no false negatives for Conjunctive, Disjunctive and Exclusive Disjunctive Monotonic Progressive Networks: CMPNs, DMPNs, and XMPNs, respectively.

Exemplary Proof:

By the law of large numbers, the empirical estimates for all rows of the CPDs will converge to their corresponding true parameter values. To show that the α filter will not create false negatives, it can be shown that a for all true parent sets must be strictly positive for all rows of the CPDs. The α values for positives rows can be always 1, and will thus never be negative. The α values for negative rows can be negative, if $\theta+<\theta-$, for negative row I of a CPD and $\theta+$ as appropriately defined for each of the MPN types. Thus, it can be shown that for all 3 types of MPNs, each negative row will have a strictly positive α. In all three cases, the fact that the conditional probability for all negative rows of all CPDs can be strictly below q and that for the positive rows can be strictly above ε can be used.

Exemplary Case I

Here, $\theta+$ refers to the conditional probability of 1 positive row, which can be by definition larger than $\varrho$, or restated, $\theta+-\varrho>0$. Combined with the fact that $\theta-<\varrho$, it follows that $\theta+>\theta-$ and thus, α will never be negative.

Exemplary Case II

The derivation below establishes that $\theta+$ can be always strictly larger than q for the true parents sets in a DMPN. The summation can be over all values of the parents that may not be all zeroes. Here, n refers to the number of parents in Pa(X). That can be, $n=|Pa(X)|$. The inequality can exploit the fact that each conditional probability corresponds to a positive row and can be thus strictly larger than ε.

Case III:

The derivation below shows, just like in the DMPN, that $\theta+>\varrho$ for all true parents sets in the XMPN. The reasoning behind this can be similar to that above, except for the summation can be over the rows in which exactly one parent takes value 1 and the rest take value 0. To denote this, the standard notation Pai(X) can be used to mean the ith parent of X and Pa-i(X) to mean all parents except for the ith parent of X.

Lemma 3 (Consistency of Polaris):

Polaris can be a statistically consistent score.

Exemplary Proof

Let M be the number of samples generated by the graph $G^*=(V, E^*)$. Let $G=(V, E)$ be the graph learned by maximizing the Polaris score, and GBIC be the graph learned by maximizing the BIC score, both for a sufficiently large M. The exemplary Polaris score can consist of three terms: (i) the log-likelihood (LL) term, (ii) the regularization term from BIC and (iii) the monotonicity term. Each of these terms can grow at different rates. The LL term can grow linearly (O(M)) with the number of samples. The regularization term can grow logarithmically (O(log M)). The monotonicity term does not grow (O(1)), since the sum of α scores can grow linearly with the number of samples, M, but it can be weighted by 1/M. Consequently, it can be subsumed by the other two terms. Thus, any perturbation to the graph G that would increase the monotonicity score but decrease the BIC score can also decrease the Polaris score.

From the consistence of BIC theorem, it can be known that any perturbation to the undirected skeleton or v-structures of GBIC can result in a lower BIC score. It follows that for sufficiently large M, the addition of the monotonicity term may not change the undirected skeleton or v-structures of GBIC. Therefore, G can be I-equivalent to GBIC and by transitivity, G can be I-equivalent to G*

Exemplary Theorem 6 (Convergence Conditions for Polaris)

For a sufficiently large sample size, M, under the assumptions of no transitive edges and faithful temporal priority relations between nodes and their parents at least for nodes that have exactly one parent, optimizing Polaris convergences to the exact structure for MPNs. Proof: Let $G^*=(V, E^*)$ be the graph that generates the data and G, the graph learned by optimizing the Polaris score. By the Polaris consistency Lemma, for sufficiently large M, the undirected skeleton and v-structures of G can be the same as those of G*. Below, it is shown that under assumptions of temporal priority for all parent-child relations, $G=G^*$.

Next, it can be shown that the parent set of each node can be learned correctly, by considering nodes that have zero parents, one parent or two or more parents. It then follows that all of the edges in the undirected skeleton of G* can be oriented correctly and thus $G=G^*$.

Exemplary Case IV $X_i$ has 0 parents. If $X_i$ has no parents, then the undirected skeleton around $X_i$ will only include the edges to the children of $X_i$. Thus, the empty parent set can be learned correctly.

Exemplary Case V $X_i$ has 1 parent. Let $X_j$ be the parent of $X_i$.

Exemplary Case V (a)

$X_j$ has 0 parents. By definition, $X_j$ has 0 parents and $X_i$ has exactly 1 parent, $X_j$. Reorienting the edge $X_j \rightarrow X_i$ to $X_j \leftarrow X_i$ results in an I-equivalent graph globally, because the edge may not be involved in a v-structure in either orientation. Thus, the BIC score for both orientations can be the same, and in order for Polaris to correctly choose $X_j \rightarrow X_i$ over $X_i \rightarrow X_j$, it must be the case that $\alpha X_i \rightarrow X_j < \alpha X_j \rightarrow X_i$. In the derivation below, it can be shown that this condition can be equivalent to the condition for temporal priority. Namely, $\alpha X_i \rightarrow X_j < \alpha X_j \rightarrow X_i$ can be equivalent to $P(X_i) < P(X_j)$. To conserve space, let $P(X_i|X_j)=\theta+$ and $P(X_i|X^-_j)=\theta-$. Also, the identity $P(X_i)=P(X_i|X_j)P(X_j)+P(X_i|X^-_j)P(X^-_j)=\theta+P(X_j)+\theta-P(X^-_j)$ can be used. The following statements can be all equivalent:

Exemplary Case V (b)

$X_j$ has 1 or more parents. Incorrectly reorienting the edge $X_j \rightarrow X_i$ to $X_j \leftarrow X_i$ makes $X_i$ a parent of $X_j$. Because G* can be acyclic and has no transitive edges, there can be no edges between $X_i$ and the true parents of $X_j$. Thus, making $X_i$ a new parent of $X_j$ creates a new v-structure (e.g., case VI proves that if $X_j$ has 2 or more parents, then they can be all unwed), consisting of $X_i$, $X_j$, and the true parents of $X_j$, that may not be in G*. This can contradict the consistency of Polaris, and thus the edge $X_j$-$X_i$ will never be reoriented.

Case VI $X_i$ has 2 or more parents. Because G* has no transitive edges, there cannot be any edge between any two parents of $X_i$. Thus, the parents of $X_i$ can be unwed and form a v-structure with $X_i$. Because Polaris can be consistent, this v-structure can be learned correctly.

Exemplary Corollary 1 (Convergence Conditions for Polaris with Filtering)

For a sufficiently large sample size, M, under the assumptions of no transitive edges and faithful temporal priority relations, filtering with the α-filter and then optimizing Polaris convergences to the exact structure for MPNs. Proof:

In Lemma 1, it was shown that α-filtering removes no true parent sets. In Theorem 6, it was shown that given a hypothesis space that includes the true parent sets, optimizing Polaris returns the true graph. Because the α-filter does not remove the true parent sets from the hypothesis space, optimizing Polaris will still return the correct structure on the filtered hypothesis space.

Figure 35:
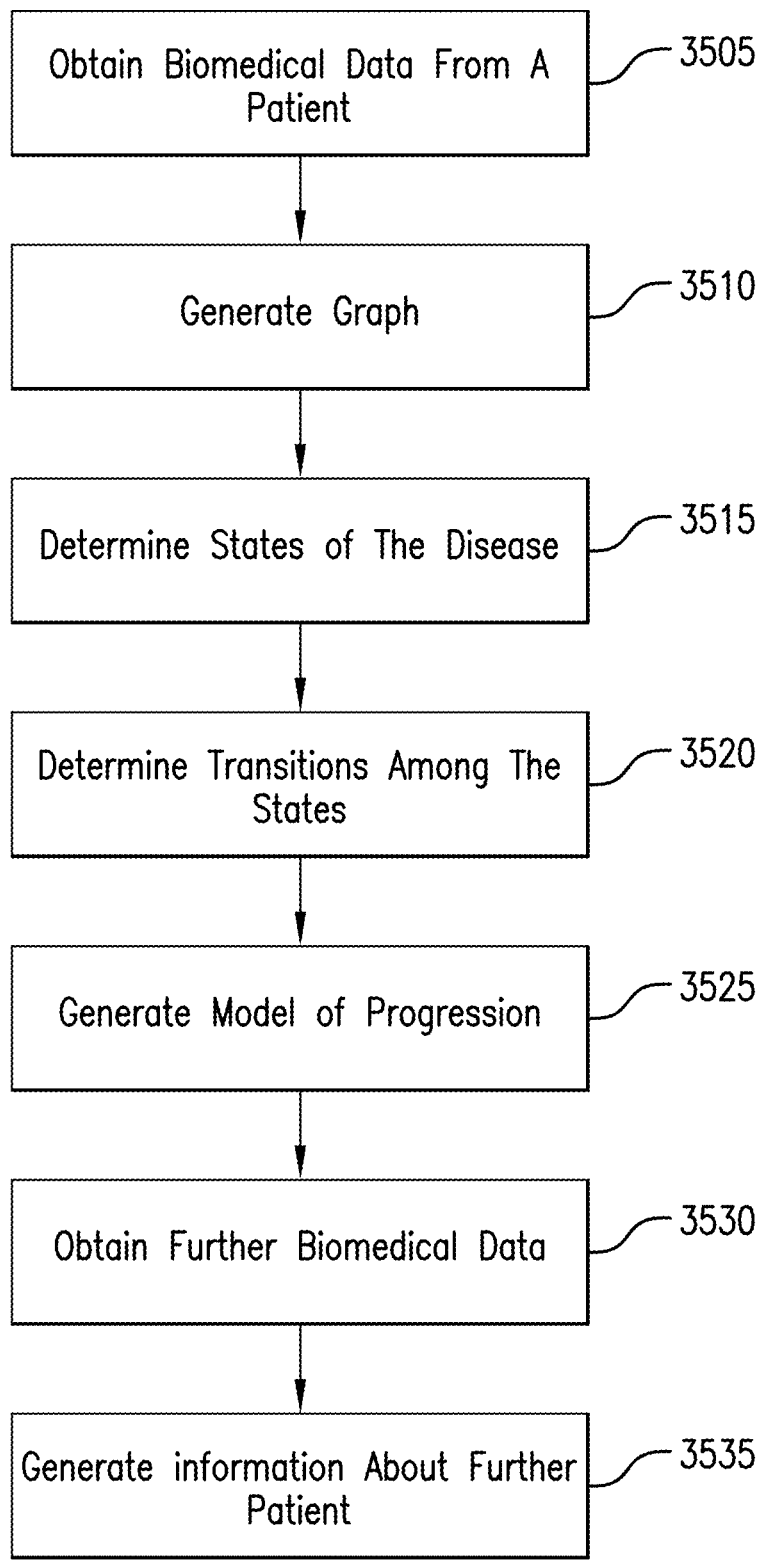
FIG. 35 is a flow diagram of an exemplary method for generating a model of progression of a disease according to an exemplary embodiment of the present disclosure.

FIG. 35 illustrates a flow diagram of an exemplary method for generating a model of progression about at disease. For example, at procedure 3505, biomedical data about one or more patients can be obtained. A graph can be generated from the biomedical data at procedure 3510. At procedure 3515, states of the disease can be determined, and at procedure 3520, transitions among the states can be determined. At procedure 3525, the model of progression can be generated. At procedure 3530, further biomedical data from a further patient can be obtained, and information about a disease that the further patient may have can be generated at procedure 3535.

Figure 9:
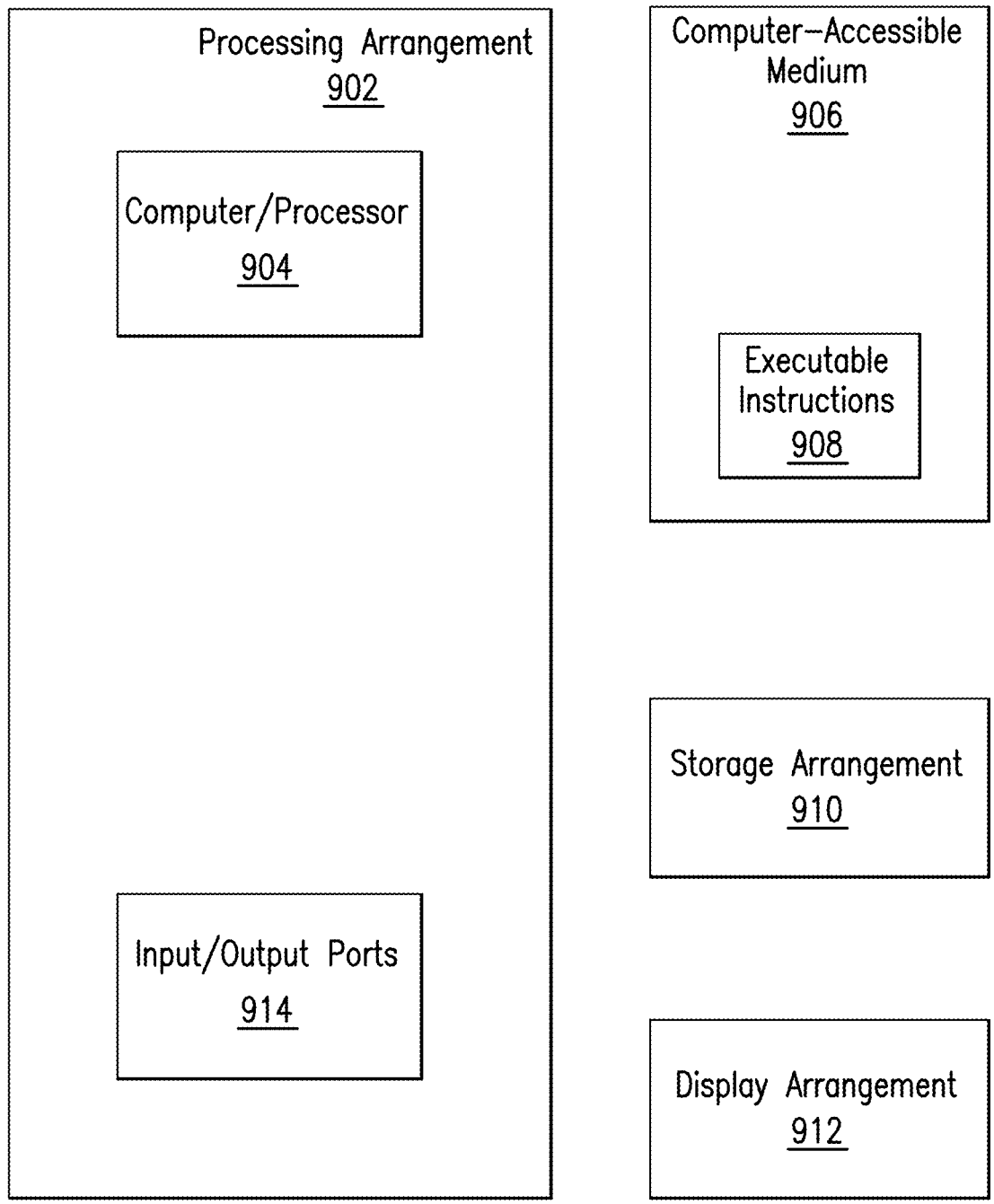
FIG. 9 is an illustration of an exemplary block diagram of an exemplary system in accordance with certain exemplary embodiments of the present disclosure.

FIG. 9 shows a block diagram of an exemplary embodiment of a system according to the present disclosure, which can implement the exemplary embodiments of the method and procedures described herein. For example, exemplary procedures in accordance with the present disclosure described herein can be performed by a processing arrangement and/or a computing arrangement 902. Such processing/computing arrangement 902 can be, for example, entirely or a part of, or include, but not limited to, a computer/processor 904 that can include, for example, one or more microprocessors, and use instructions stored on a computer-accessible medium (e.g., RAM, ROM, hard drive, or other storage device).

As shown in FIG. 9, for example, a computer-accessible medium 906 (e.g., as described herein above, a storage device such as a hard disk, floppy disk, memory stick, CD-ROM, RAM, ROM, etc., or a collection thereof) can be provided (e.g., in communication with the processing arrangement 902). The computer-accessible medium 906 can contain executable instructions 908 thereon. In addition or alternatively, a storage arrangement 910 can be provided separately from the computer-accessible medium 906, which can provide the instructions to the processing arrangement 902 so as to configure the processing arrangement to execute certain exemplary procedures, processes and methods, as described herein above, for example.

Further, the exemplary processing arrangement 902 can be provided with or include an input/output arrangement 914, which can include, for example, a wired network, a wireless network, the internet, an intranet, a data collection probe, a sensor, etc. For example, anatomical data 920 can be provided to the input/output arrangement 914. As shown in FIG. 9, the exemplary processing arrangement 902 can be in communication with an exemplary display arrangement 912, which, according to certain exemplary embodiments of the present disclosure, can be a touch-screen configured for inputting information to the processing arrangement in addition to outputting information from the processing arrangement, for example. Further, the exemplary display 912 and/or a storage arrangement 910 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] BEERENWINKEL, N.; ERIKSSON, N., AND STURMFELS, B. Conjunctive bayesian networks. Bernoulli (2007), 893-909.
[2] BEERENWINKEL, N., RAHNENFUHRER, J.; DAUMER, M., HOFFMANN, D., KAISER, R.; SELBIG, J., AND LENGAUER, T. Learning multiple evolutionary pathways from cross-sectional data. Journal of Computational Biology 12, 6 (2005), 584-598.
[3] BELL, D.; BERCHUCK, A.; BIRRER, M.; CHIEN, J.; CRAMER, D., DAO, F., DHIR, R.; DISAIA, P.; GABRA, H.; AND GLENN, P. Integrated genomic analyses of ovarian carcinoma.
[4] DESPER, R., JIANG, F.; KALLIONIEMI, O., MOCH, H., PAPADIMITRIOU, C., AND SCHAFFER, A. Inferring tree models for oncogenesis from comparative genome hybridization data. Journal of Computational Biology 6, 1 (1999), 37-51.
[5] DESPER, R., JIANG, F., KALLIONIEMI, O., MOCH, H., PAPADIMITRIOU, C., AND SCHAFFER, A. Distance-based reconstruction of tree models for oncogenesis. Journal of Computational Biology 7, 6 (2000), 789-803.
[6] EDMONDS, J. Optimum branchings. Journal of Research of the National Bureau of Standards B 71 (1967), 233-240.
[7] EFRON, B. Bootstrap methods: another look at the jackknife. The annals of Statistics (1979), 1-26.
[8] EFRON, B. The jackknife, the bootstrap and other resampliny plans, vol. 38. SIAM, 1982.
[9] EFRON, B. Large-Scale Inference: Empirical Bayes Methods for Estimation, Testing, and Prediction. Cambridge University Press, 2013.
[10] EFRON, B., AND MORRIS, C. Stein's estimation rule and its competitors—an empirical bayes approach. Journal of the American Statistical Association 68, 341 (1973), 117-130.
[11] GERSTUNG, M., BAUDIS, M., MOCH, H., AND BEERENWINKEL, N. Quantifying cancer progression with conjunctive bayesian networks. Bioinfor-matics 25, 21 (2009), 2809-2815.
[12] GERSTUNG, M., ERIKSSON, N., LIN, J., VOGELSTEIN, B., AND BEEREN-WINKEL, N. The temporal order of genetic and pathway alterations in tumorigenesis. PloS one 6, 11 (2011), e27136.
[13] GUNAWAN, B., AND ET AL. An oncogenetic tree model in gastrointestinal stromal tumours (gists) identifies different pathways of cytogenetic evolution with prognostic implications. The Journal of pathology 211, 4 (2007), 463-470.
[14] HANAHAN, D., AND WEINBERG, R. A. The hallmarks of cancer. Cell 100, 1 (2000), 57-70.
[15] HANAHAN, D., AND WEINBERG, R. A. Hallmarks of cancer: The next generation. Cell 144 (2011), 646-674.
[16] HITCHCOCK, C. Probabilistic causation. In The Stanford Encyclopedia of Philosophy, E. Zalta, Ed., winter 2012 ed. 2012.
[17] HJELM, M. New probabilistic network models and algorithms for oncoge-nesis. Journal of Computational Biology, 853-865 (13).
[18] HUANG, Q., Yu, G.; MCCORMICK, S., MO; J., DATTA, B., MAHIMKAR, M., LAZARUS, P., SCHAFFER, A. A., DESPER, R., AND SCHANTZ, S. Genetic differences detected by comparative genomic hybridization in head and neck squamous cell carcinomas from different tumor sites: construction of oncogenetic trees for tumor progression. Genes, Chromosomes and Cancer 34, 2 (2002), 224-233.
[19] Ki, M., AND ET AL. Mapping the hallmarks of lung adenocarcinoma with massively parallel sequencing. Cell 150, 6 (2012), 1107-1120.
[20] IONITA, I., DARUWALA, R., AND MISHRA, B. Mapping Tumor-Suppressor genes with multipoint statistics from Copy-Number—Variation data. American Journal of Human Genetics 79, 1 (July 2006), 13-22. PMID: 16773561 PMCID: 1474131.
[21] KAINU, T., AND ET AL. Somatic deletions in hereditary breast cancers implicate 13q21 as a putative novel breast cancer susceptibility locus. Proceedings of the National Academy of Sciences 97, 17 (2000), 9603-9608.
[22] KLEINBERG, S. Causality, Probability, and Time. Cambridge University Press, 2012.
[23] KNUTSEN, T., GOBU, V., KNAUS, R., PADILLA-NASH, H., AUGUSTUS, M., STRAUSBERG, R., KIRSCH, I., SIROTKIN, K., AND RIED, T. The interactive online sky/m-fish & database and the entrez cancer chromosomes search database: Linkage of chromosomal aberrations with the genome sequence. Genes, Chromosomes and Cancer 44, 1 (2005), 52-64.
[24] LONGERICH, T., MUELLER, M., BREUHAHN, K., SCHIRMACHER, P., BENNER, A., AND HEISS, C.

Oncogenetic tree modeling of human hepatocarcinogenesis. International Journal of Cancer 130, 3 (2012), 575-583.

[25] Luo, J., SOLIMINI, N. L., AND ELLEDGE, S. J. Principles of cancer therapy: Oncogene and non-oncogene addiction. Cell 136, 5 (March 2009), 823-837.

[26] PATHARE, S., SCHAFFER, A., BEERENWINKEL, N., AND MAHIMKAR, M. Construction of oncogenetic tree models reveals multiple pathways of oral cancer progression. International journal of cancer 124, 12 (2009), 2864-2871.

[27] RADMACHER, M., SIMON, R., DESPER, R., TAETLE, R., SCHAFFER, A., AND NELSON, M. Graph models of oncogenesis with an application to melanoma. Journal of theoretical biology 212, 4 (2001), 535-548.

[28] REICHENBACH, H. The Direction of Time. University of California Press, 1956.

[29] SAMUELSON, E.; KARLSSON; S., PARTHEEN, K., NILSSON, S., SZPIRER, C., AND BEHBOUDI, A. Baccgh-array identified specific small-scale genomic imbalances in diploid dmba-induced rat mammary tumors. BMC cancer 12, 1 (2012), 352.

[30] SUPPES, P. A probabilistic theory of causality. North Holland Publishing Company, 1970.

[31] TIBSHIRANI, R. Regression shrinkage and selection via the lasso. Journal of the Royal Statistical Society: Series B 58, 1 (1996), 267-288.

[32] VOGELSTEIN, B.; FEARON, E. R., HAMILTON, S. R., KERN, S. E., PREISINGER, A. C., LEPPERT, M., SMITS, A. M., AND Bos, J. L. Genetic alterations during colorectal-tumor development. New England Journal of Medicine 319, 9 (1988), 525-532.

[33] VOGELSTEIN, B., AND KINZLER, K. Cancer genes and the pathways they control. Nature medicine 10, 8 (2004), 789-799.

[34] XUE, W., AND ET AL. A cluster of cooperating tumor-suppressor gene candidates in chromosomal deletions. Proceedings of the National Academy of Sciences 109, 21 (2012), 8212-8217.

[35] ZHANG, K., AND SHASHA, D. Simple fast algorithms for the editing distance between trees and related problems. SIAM journal on computing 18, 6 (1989), 1245-1262.

[36] P. M. Illari, F. Russo, and J. Williamson, eds., Causality in the Sciences. Oxford University Press, 2011.

[37] C. Hitchcock, "Probabilistic causation," in The Stanford Encyclopedia of Philosophy (E. N. Zalta, ed.), winter 2012 ed., 2012.

[38] J. B. Haldane, The Causes of Evolution. Princeton University Press, 1990.

[39] D. Hume, An Enquiry Concerning Human Understanding. 1748.

[40] H. Kyburg, "Discussion: Salmon's paper," Philosophy of Science, 1965.

[41] P. Suppes, A Probabilistic Theory of Causality. North-Holland Publishing Company, 1970.

[42] H. Reichenbach, The Direction of Time. University of California Press, 1956.

[43] N. Cartwright, Causal Laws and Effective Strategies. Noes, 1979.

[44] B. Skyrms, Causal Necessity. Yale University Press, 1980.

[45] E. Fells, Probabilistic Causality. Cambridge University Press, 1991.

[46] J. Pearl, Causality: Models, Reasoning, and Inference. Cambridge University Press, 2000.

[47] P. Menzies, "Counterfactual theories of causation," in The Stanford Encyclopedia of Philos-ophy (E. N. Zalta, ed.), spring 2014 ed., 2014.

[48] D. Lewis, "Causation," Journal of Philosophy, 1973.

[49] J. Woodward, "Causation and manipulability," in The Stanford Encyclopedia of Philosophy (E. N. Zalta, ed.), winter 2013 ed., 2013.

[50] D. Koller and N. Friedman, Probabilistic Graphical Models: Principles and Techniques—Adaptive Computation and Machine Learning. The MIT Press, 2009.

[51] J. Pearl, Probabilistic reasoning in intelligent systems: networks of plausible inference. Mor¬gan Kaufmann, 1988.

[52] T. Verma and J. Pearl, "Equivalence and synthesis of causal models," in Uncertainty in Artifical Intelligence Proceedings of the Sixth Conference (M. Henrion, R. Shachter, L. Kanal, and J. Lemmer, eds.), (San Francisco, Calif., USA), pp. 220-227, Morgan Kaufmann, 1990.

[53] D. M. Chickering, "Learning bayesian networks is np-complete," in Learning from data, pp. 121-130, Springer, 1996.

[54] D. M. Chickering, D. Heckerman, and C. Meek, "Large-sample learning of bayesian networks is np-hard," The Journal of Machine Learning Research, vol. 5, pp. 1287-1330, 2004.

[55] P. Spirtes, C. N. Glymour, and R. Scheines, Causation, prediction, and search, vol. 81. MIT press, 2000.

[56] I. Tsamardinos, C. F. Aliferis, A. R. Statnikov, and E. Statnikov, "Algorithms for large scale markov blanket discovery.," in FLAIRS Conference, vol. 2003, pp. 376-381, 2003.

[57] A. M. Carvalho, "Scoring functions for learning bayesian networks," Inesc-id Tec. Rep, 2009.

[58] N. Beerenwinkel, N. Eriksson, and B. Sturmfels, "Conjunctive bayesian networks," Bernoulli, 2007.

[59] M. Gerstung, M. Baudis, H. Moch, and N. Beerenwinkel, "Quantifying cancer progression with conjunctive bayesian networks," Bioinformatics, vol. 25, no. 21, pp. 2809-2815, 2009.

[60] T. K. Moon, "The expectation-maximization algorithm," Signal processing magazine, IEEE, vol. 13, no. 6, pp. 47-60, 1996.

[61] S. Kirkpatrick, "Optimization by simulated annealing: Quantitative studies," Journal of statistical physics, vol. 34, no. 5-6, pp. 975-986, 1984.

[62] L. O. Loohuis, G. Caravagna, A. Graudenzi, D. Ramazzotti, G. Mauri, M. Antoniotti, and B. Mishra, "Inferring tree causal models of cancer progression with probability raising." Submitted for publication (available at arXiv.org)., 2013.

[63] R. Desper, F. Jiang, O.-P. Kallionierni, H. Moch, C. Papadimitriou, and A. Schaffer, "Inferring tree models for oncogenesis from comparative genome hybridization data," Journal of Computational Biology, 1999.

[64] N. Beerenwinkel, J. R. ahnenfiihrer, Ni. Daumer, D. Hoffmann, R. Kaiser, J. Selbig, and T. Lengauer, "Learning multiple evolutionary pathways from cross-sectional data," Journal of Computational Biology, 2005.

[65] A. Szabo and K. Boucher, "Estimating an oncogenetic tree when false negatives and positives are present," Mathematical biosciences, 2002.

[66] B. Efron, The Jackknife, the Bootstrap, and Other Resampling Plans. SIAM, 1982.

[67] B. Efron, Large-Scale Inference: Empirical Bayes Methods for Estimation, Testing, and Prediction. Cambridge University Press, 2013.

[68] H. B. Mann and D. R. Whitney, "On a test of whether one of two random variables is stochastically larger than the other," Annals of Mathematical Statistics, vol. 18, no. 1, pp. 50-60, 1947.

[69] G. Schwarz, "Estimating the dimension of a model," Annals of Statistics, 1978.

[70] D. Heckerman, D. Geiger, and D. Chickering, "Learning bayesian networks: The combina¬tion of knowledge and statistical data," Machine Learning, 1995.

[71] R. W. Hamming, "Error-detecting and error-correcting codes," Bell System Technical Jour¬nal, 1950.

[72] "The cancer genome atlas." http://cancergenome.nih.gov/, 2005.

[73] M. Scutari, "Learning bayesian networks with the bnlearn r package," Journal of Statistical Software, 2010.

[74] "The TRONCO package for translational oncology." Available at standard R repositories.

[↓] "Hidden conjunctive bayesian networks." http://www.silva.bsse.ethz.ch/cbg/software/ct-cbn.

[76] D. Margaritis, Learning Bayesian Network Model Structure from Data. PhD thesis, School of Computer Science, Carnegie-Mellon University, Pittsburgh, Pa., 2003.

[77] H. S. Farahani and J. Lagergren, "Learning oncogenetic networks by reducing to mixed integer linear programming," PLoS ONE, 2013.

[78] R. Piazza, S. Valletta, N. Winkelmann, S. Redaelli, R. Spinelli, A. Pirola, L. Antolini, L. Mologni, C. Donadoni, E. Papaemmanuil, S. Schnittger, D.-W. Kim, J. Boultwood, F. Rossi, G. Gaipa, G. P. D. Martini, P. F. di Celle, H. G. Jang, V. Fantin, C. R. Bignell, V. Magistroni, T. Haferlach, E. M. Pogliani, P. J. Campbell, A. J. Chase, W. J. Tap¬per, N. C. P. Cross, and C. Gambacorti-Passerini, "Recurrent setbp1 mutations in atypical chronic myeloid leukemia," Nature Genetics, 2013.

[79] M. Imielinski et al., "Mapping the hallmarks of lung adenocarcinoma with massively parallel sequencing," Cell, vol. 150, no. 6, pp. 1107-1120, 2012.

What is claimed is:

1. A non-transitory computer-accessible medium having stored thereon computer-executable instructions for generating a model of progression of cancer using biomedical data of at least one patient, wherein, when a computer arrangement executes the instructions, the computer arrangement is configured by the instruction to perform procedures comprising:

obtaining the biomedical data which includes at least one of genomics, transcriptomics, or epigenomics;

generating the model of progression which includes (i) states of the cancer and (ii) transitions among the states using a learning network, based on the obtained biomedical data, wherein:

transitions among the states are determined by a causality relationship information whose strength is estimated by probability-raising by at least one estimator which is part of the learning network;

the at least one estimator includes at least one shrinkage estimator which is a measure of causation among any pair of events atomic events; and the at least one shrinkage estimator is defined as $\theta=(1-\lambda)\alpha(x)+\lambda\beta(x)$, where $0\leq\lambda\leq 1$ can be a shrinkage coefficient, x is an input data, and $\theta$ is one or more estimates for an evaluation, wherein the learning network includes the transitions and the at least one shrinkage estimator;

receiving further biomedical data associated with a further patient;

classifying a particular state of cancer for the further patient using the model of progression and the further biomedical data, wherein a particular state of the states of cancer is classified by one or more mutational profiles of the at least one of the genomics, the transcriptomics or the epigenomics; and determining a genome-specific therapy design based on the classification of the particular state of cancer.

2. The computer-accessible medium of claim 1, wherein the model of progression further includes a progression graph.

3. The computer-accessible medium of claim 2, wherein the progression graph is based on a causal graph.

4. The computer-accessible medium of claim 2, wherein the model of progression further includes at least one of a directed acyclic graph (DAG), a disconnected DAG, a tree or a forest.

5. The computer-accessible medium of claim 1, wherein nodes of the model of progression are atomic events and edges that represent a progression between the atomic events.

6. The computer-accessible medium of claim 1, wherein the model of progression is further based on a noise model.

7. The computer-accessible medium of claim 6, wherein the noise model includes a biological noise model.

8. The computer-accessible medium of claim 7, wherein the computer arrangement is further configured to use the biological noise model to distinguish spurious causes from genuine causes.

9. The computer-accessible medium of claim 6, wherein the noise model includes an experimental noise model.

10. The computer-accessible medium of claim 6, wherein the noise model includes an experimental noise model and a biological noise model.

11. The computer-accessible medium of claim 1, wherein the biomedical data further includes imaging data.

12. The computer-accessible medium of claim 1, wherein the biomedical data includes information pertaining to at least one of at least one normal cell, at least one tumor cell, cell-free circulating DNA or at least one circulating tumor cell.

13. A method for modeling a progression of cancer using biomedical data for one or more patients, comprising:

(a) obtaining the biomedical data which includes at least one of genomics, transcriptomics, or epigenomics;

(b) using a computer hardware arrangement, generating the model of progression which includes (i) states of the cancer and (ii) transitions among the states using a learning network, based on the obtained biomedical data, wherein:

transitions among the states are determined by a causality relationship information whose strength is estimated by probability-raising by at least one estimator which is part of the learning network;

the at least one estimator includes at least one shrinkage estimator, which is a measure of causation among any pair of events atomic events; and the at least one shrinkage estimator is defined as $\theta=(1-\lambda)\alpha(x)+\lambda\beta(x)$, where $0\leq\lambda\leq 1$ can be a shrinkage coefficient, x is an input data, and $\theta$ is one or more estimates for an evaluation, wherein the learning network includes the transitions and the at least one shrinkage estimator;

(c) receiving further biomedical data associated with a further patient;

(d) classifying a particular state of cancer for the further patient using the model of progression and the further biomedical data, wherein a particular state of the states of cancer is classified by one or more mutational profiles of the at least one of the genomics, the transcriptomics or the epigenomics; and (e) determining a genome-specific therapy design based on the classification of the particular state of cancer.

14. A system for modeling a progression of cancer using biomedical data for one or more patients, comprising:

a computer hardware arrangement configured to:
(a) obtain the biomedical data which includes at least one of genomics, transcriptomics, or epigenomics;
(b) using a computer hardware arrangement, generate the model of progression which includes (i) states of the cancer and (ii) transitions among the states using a learning network, based on the obtained biomedical data, wherein:
transitions among the states are determined by a causality relationship whose strength is estimated by probability-raising by at least one estimator which is part of the learning network;
the at least one estimator includes at least one shrinkage estimator, which is a measure of causation among any pair of events atomic events; and
the at least one shrinkage estimator is defined as $\theta=(1-\lambda)\alpha(x)+\lambda\beta(x)$, where $0\leq\lambda\leq1$ can be a shrinkage coefficient, x is an input data, and $\theta$ is one or more estimates for an evaluation, wherein the learning network includes the transitions and the at least one shrinkage estimator;
(c) receive further biomedical data associated with a further patient;
(d) classify a particular state of cancer for the further patient using the model of progression and the further biomedical data, wherein a particular state of the states of cancer is classified by one or more mutational profiles of the at least one of the genomics, the transcriptomics or the epigenomics; and
(e) determine a genome-specific therapy design based on the classification of the particular state of cancer.

* * * * *